US012257348B2

(12) United States Patent
Toledano et al.

(10) Patent No.: US 12,257,348 B2
(45) Date of Patent: *Mar. 25, 2025

(54) STABILIZED MICROCAPSULES, METHOD OF THEIR PREPARATION AND USES THEREOF

(71) Applicant: Sol-Gel Technologies Ltd., Ness Ziona (IL)

(72) Inventors: Ofer Toledano, Kfar Saba (IL); Karine Neimann, Ness Ziona (IL); Danil Finkel-Moiseev, Rehovot (IL); Maya Erlich, Ness Ziona (IL); Dorit Marco, Rehovot (IL)

(73) Assignee: Sol-Gel Technologies Ltd., Ness Ziona (IL)

( * ) Notice: Subject to any disclaimer, the term of this patent is extended or adjusted under 35 U.S.C. 154(b) by 223 days.

This patent is subject to a terminal disclaimer.

(21) Appl. No.: 17/327,724

(22) Filed: May 23, 2021

(65) Prior Publication Data

US 2021/0361586 A1   Nov. 25, 2021

Related U.S. Application Data

(60) Provisional application No. 63/028,599, filed on May 22, 2020.

(51) Int. Cl.
| | | |
|---|---|---|
| *A61K 9/48* | (2006.01) | |
| *A61K 9/00* | (2006.01) | |
| *A61K 9/50* | (2006.01) | |
| *A61K 31/202* | (2006.01) | |
| *A61K 31/203* | (2006.01) | |
| *A61K 31/235* | (2006.01) | |
| *A61K 31/327* | (2006.01) | |
| *A61K 31/336* | (2006.01) | |

(52) U.S. Cl.
CPC .......... *A61K 9/4808* (2013.01); *A61K 9/0014* (2013.01); *A61K 9/4841* (2013.01); *A61K 9/4858* (2013.01); *A61K 9/4875* (2013.01); *A61K 9/501* (2013.01); *A61K 9/5084* (2013.01); *A61K 9/5089* (2013.01); *A61K 31/202* (2013.01); *A61K 31/203* (2013.01); *A61K 31/235* (2013.01); *A61K 31/327* (2013.01); *A61K 31/336* (2013.01)

(58) Field of Classification Search
CPC .......... A61K 31/327; A61K 9/50; A61K 9/501
See application file for complete search history.

(56) References Cited

U.S. PATENT DOCUMENTS

| | | |
|---|---|---|
| 4,235,872 A | 11/1980 | Tocker |
| 4,670,250 A | 6/1987 | Baker |
| 4,970,031 A | 11/1990 | Gotoh |
| 5,238,714 A | 8/1993 | Wallace et al. |
| 5,575,987 A | 11/1996 | Kamei et al. |
| 6,913,825 B2 | 7/2005 | Ostafin et al. |
| 7,629,394 B2 | 12/2009 | Yan |
| 8,617,580 B2 | 12/2013 | Toledano et al. |
| 9,107,844 B2 | 8/2015 | Clark et al. |
| 9,205,395 B2 | 12/2015 | Yan |
| 9,682,031 B2 | 6/2017 | Goldstein et al. |
| 9,687,465 B2* | 6/2017 | Sertchook .......... A61K 31/7056 |
| 9,868,103 B2 | 1/2018 | Toledano et al. |
| 10,420,743 B2 | 9/2019 | Toledano et al. |
| 10,512,796 B2 | 12/2019 | Toledano et al. |
| 10,525,433 B2 | 1/2020 | Toledano et al. |
| 10,653,899 B2 | 6/2020 | Toledano et al. |
| 10,688,462 B2 | 6/2020 | Toledano et al. |
| 10,945,987 B2* | 3/2021 | Toledano ................. A61K 9/06 |
| 11,541,026 B2* | 1/2023 | Arkin .................... A61K 31/327 |
| 2002/0064541 A1* | 5/2002 | Lapidot .................. A61Q 19/00 |
| | | 424/490 |
| 2004/0137031 A1 | 7/2004 | Seitz et al. |
| 2006/0003014 A1 | 1/2006 | Jadhav et al. |
| 2010/0016443 A1 | 1/2010 | Toledano et al. |
| 2010/0047357 A1 | 2/2010 | Toledano et al. |
| 2010/0180464 A1 | 7/2010 | Laakso et al. |
| 2013/0095185 A1* | 4/2013 | Toledano .............. A61K 9/0014 |
| | | 424/490 |
| 2014/0186630 A1 | 7/2014 | Schwantes |
| 2015/0190372 A1 | 7/2015 | Djedour |
| 2015/0328615 A1 | 11/2015 | Dihora et al. |
| 2017/0281571 A1 | 10/2017 | Sertchook et al. |
| 2018/0117369 A1 | 5/2018 | Toledano et al. |
| 2018/0147165 A1 | 5/2018 | Sertchook et al. |
| 2018/0207451 A1 | 7/2018 | Toledano et al. |
| 2018/0235924 A1* | 8/2018 | Toledano ................. A61K 9/16 |

(Continued)

FOREIGN PATENT DOCUMENTS

| | | |
|---|---|---|
| EP | 0248531 A2 | 12/1987 |
| IN | 1958/CHE/2007 | 9/2009 |

(Continued)

OTHER PUBLICATIONS

Spectrum (Material Safety Data Sheet, Hydrous benzoyl peroxide, USP, 2012, pp. 1-7) (Year: 2012).*
Akpoveta (Egyptian Journal of Petroleum, online Jan. 23, 2020, vol. 29, pp. 113-119) (Year: 2020).*
Zakharova et al (International Journal of Molecular Sciences, Nov. 2019, vol. 20, pp. 1-31) (Year: 2019).*
Falls, A. H. et al. (1983). A transmission electron microscopy study of hexagonal ice. *Journal of Materials Science*, 18(9), 2752-2764.
Gollnick, H. et al. (2003). Management of acne: a report from a Global Alliance to Improve Outcomes in Acne. *Journal of the American Academy of Dermatology*, 49(1), S1-S37.

(Continued)

*Primary Examiner* — Mark V Stevens
(74) *Attorney, Agent, or Firm* — Mark S. Cohen; PEARL COHEN ZEDEK LATZER BARATZ LLP

(57) ABSTRACT

The present application is directed to stabilized core-shell microcapsules comprising a core of benzoyl peroxide (BPO) or all trans retinoic acid (ATRA) and a metal-oxide shell; and to pharmaceutical compositions and methods of use thereof.

32 Claims, 25 Drawing Sheets

(56) References Cited

U.S. PATENT DOCUMENTS

| | | |
|---|---|---|
| 2019/0015366 A1 | 1/2019 | Toledano et al. |
| 2019/0015368 A1 | 1/2019 | Arkin et al. |
| 2019/0015369 A1 | 1/2019 | Arkin et al. |
| 2019/0336464 A1 | 11/2019 | Toledano et al. |
| 2020/0114327 A1 | 4/2020 | Toledano et al. |
| 2020/0316005 A1 | 10/2020 | Toledano et al. |
| 2020/0383927 A1 | 12/2020 | Toledano et al. |
| 2021/0007996 A1 | 1/2021 | Toledano et al. |
| 2021/0113511 A1 | 4/2021 | Toledano et al. |

FOREIGN PATENT DOCUMENTS

| | | |
|---|---|---|
| IN | 2080/CHE/2007 | 9/2009 |
| WO | WO-1993021764 A1 | 11/1993 |
| WO | WO-1994020075 A1 | 9/1994 |
| WO | WO-2005009604 A1 | 2/2005 |
| WO | WO-2007015243 A2 | 2/2007 |
| WO | WO-2008093346 A2 | 8/2008 |
| WO | WO-2008093347 A2 | 8/2008 |
| WO | WO-2009051839 A1 | 4/2009 |
| WO | WO-2010013250 A2 | 2/2010 |
| WO | WO-2011080741 A2 | 7/2011 |
| WO | WO-2013001536 A1 | 1/2013 |
| WO | WO-2015092602 A1 | 6/2015 |
| WO | WO-2019012536 A1 | 1/2019 |
| WO | WO-2019012537 A1 | 1/2019 |

OTHER PUBLICATIONS

Koifman, N. A. et al. (2017). A direct-imaging cryo-EM study of shedding extracellular vesicles from leukemic monocytes. *Journal of Structural Biology*, 198(3), 177-185.

Talmon, Y. et al. (1986). Electron beam radiation damage to organic inclusions in vitreous, cubic, and hexagonal ice. *Journal of Microscopy*, 141(3), 375-384.

Tanghetti, E. (2008). The evolution of benzoyl peroxide therapy. *Cutis*, 82(5 Suppl), 5-11.

Yan, A. C. (2006). Current concepts in acne management. *Adolescent Medicine Clinics*, 17(3), 613-37—Abstract.

Yue, P. F. et al. (2009). The study on the entrapment efficiency and in vitro release of puerarin submicron emulsion. *AAPS PharmSciTech*, 10(2), 376-383.

Del Rosso, J. Q. et al. (2010). Absence of degradation of tretinoin when benzoyl peroxide is combined with an optimized formulation of tretinoin gel (0.05%). *The Journal of Clinical and Aesthetic Dermatology*, 3(10), 26.

He, J. et al. (2003). Preparation of porous and nonporous silica nanofilms from aqueous sodium silicate. *Chemistry of Materials*, 15(17), 3308-3313.

Patel, V. B. et al. (2001). Clinical assessment of the combination therapy with liposomal gels of tretinoin and benzoyl peroxide in acne. *AAPS PharmSciTech*, 2(3), 1-5.

Rapini R. P., et al. (2007). Dermatology: 2-Volume Set. St. Louis: Mosby. Section 6, Adnexal Diseases, Webster G. F. Rosacea and Related Disorders, pp. 509-5016.

Skapin, S. D. et al. (2004). Preparation and coating of finely dispersed drugs: 4. Loratadine and danazol. *Journal of Colloid and Interface Science*, 272(1), 90-98.

Tjandra, W. et al. (2006). Interaction between silicates and ionic surfactants in dilute solution. *Langmuir*, 22(4), 1493-1499.

William D. J. et al. (2011). Andrew's Diseases of the Skin, 11th ed., Chapter 13, Rosacea, pp. 241-244.

Bartlett, P. D. et al. (1947). The decomposition of benzoyl peroxide in solvents. II. Ethers, alcohols, phenols and amines. *Journal of the American Chemical Society*, 69(10), 2299-2306.

Binks, B. P. et al. (2005). Nanoparticle silica-stabilised oil-in-water emulsions: improving emulsion stability. *Colloids and Surfaces A: Physicochemical and Engineering Aspects*, 253(1-3), 105-115.

Shen, S. L. et al. (Jun. 2007). A novel process to synthesize magnetic hollow silica microspheres. *Colloids and Surfaces A: Physicochemical and Engineering Aspects*, 311(1-3), 99-105.

\* cited by examiner

STABILIZED MICROCAPSULES, METHOD OF THEIR PREPARATION AND USES THEREOF

CROSS REFERENCE TO RELATED APPLICATIONS

This application claims the benefit of U.S. Provisional Application No. 63/028,599, filed May 22, 2020, the entire contents of which is hereby incorporated by reference herein.

FIELD OF THE INVENTION

The present application is directed to stabilized core-shell microcapsules comprising a core of benzoyl peroxide (BPO) or all trans retinoic acid (ATRA) and a metal-oxide shell; and to pharmaceutical compositions and methods of use thereof.

BACKGROUND OF THE INVENTION

Topical retinoids are keratinization inhibitors. They work by decreasing the cohesiveness of follicular epithelial cells. This results in an inhibition in the formation of microcomedones, preventing the formation of mature comedones and inflammatory lesions (Gollnick and Cunliffe, *J. Am. Acad. Dermatol* 2003; 49: S1-38). Use of retinoids promotes the normal desquamation of follicular epithelium. The action of the retinoid may enhance the penetration of other topical compounds used to treat acne.

Benzoyl peroxide (BPO) is a commonly used topical antibacterial agent for acne available either by prescription in combinations or over the counter (OTC). BPO has been found to be lethal to *P. acnes* as well as other bacteria that may reside on the skin. So far there has been no indication of any bacteria developing a resistance to BPO. It has also been demonstrated that BPO has keratolytic activity contributing to its efficacy in treating comedonal acne (Tanghetti, *Cutis*, 2008, 82(5S), 3-11). BPO reduces the cohesiveness of the cells of the stratum corneum, thus improving topical drug delivery through the epidermal barrier.

Silica microcapsule systems have been developed to overcome many of the limitations (such as degradation and irritation) of standard pharmaceutical formulations involving multiple active ingredients. The encapsulation of active ingredients in silica microcapsules serves to protect components in the formulation from interacting with one another and, as a consequence, increases overall formulation stability. Silica is chemically inert, photochemically and physically stable, and safe for topical use.

Clinicians have been reluctant to prescribe topical retinoids and BPO concurrently due to a belief that the BPO may result in oxidation and degradation of the tretinoin molecule, thereby reducing its effectiveness, and prefer to recommend the BPO or an antibiotic/BPO combination to be applied in the morning and tretinoin at night (Yan A C. *Adolesc. Med. Clin.* 2006; 17(3):613-637).

Another publication (Emmy Graber, Treatment of Acne Vulgaris, UpToDate.com, July 2016) states "topical tretinoin should NOT be applied at the same time as benzoyl peroxide", despite the known fact that newer retinoid compositions like Retin A microspheres (MICROSPONGE® System) have less interaction or no short-term interaction with BPO. Obviously, concomitant administration of tretinoin and BPO is taught away by this publication.

BPO is known to oxidize tretinoin and hence it was feared that their interaction on the skin when administered together will diminish the therapeutic effect of tretinoin. Thus, while there are some reports in the literature on the value of both compounds being administered one in the morning and the other in the evening, the verdict up to now was that the two products should not be administered concomitantly. Combinations of BPO and tretinoin were also published in U.S. Pat. Nos. 8,617,580, 10,420,743, US 2019/0336464, US 2013/0095185, and US-2019/0015366.

This belief of the medical profession explains why all previous attempts to solve the stability problem of tretinoin/BPO, such as microencapsulation technology, did not yield a commercial product so far.

Since topical conditions such as acne has multiple pathogenic factors, such as abnormal follicular keratinization, *P. acnes* proliferation and inflammation, combining separate active agents that target these multiple factors would provide the patient with an effective and convenient treatment improving treatment outcomes.

Rosacea is a chronic disease of inflammatory dermatitis that mainly affects the median part of the face and the eyelids of certain adults. It is characterized by telangiectatic erythema, dryness of the skin, papules and pustules. Conventionally, rosacea develops in adults from the ages of 30 to 50; it more frequently affects women, although the condition is generally more severe in men. Rosacea is a primitively vascular condition whose inflammatory stage lacks the cysts and comedones characteristic of common acne.

Factors that have been described as possibly contributing towards the development of rosacea include for example: the presence of parasites such as the *Demodex folliculorum*, the presence of bacteria such as *Helicobacter pylori* (a bacterium associated with gastrointestinal disorders), hormonal factors (such as endocrine factors), climatic and immunological factors, and so forth.

Rosacea develops in four stages over several years, in spasms aggravated by variations in temperature, alcohol, spices, exposure to sunlight and stress.

The various stages of the disease are the following:

Stage 1: stage of erythema episodes. The patients have erythrosis spasms due to the sudden dilation of the arterioles of the face, which then take on a congestive, red appearance. These spasms are caused by the emotions, meals and temperature changes.

Stage 2: stage of couperosis, i.e., of permanent erythema with telangiectasia. Certain patients also have oedema on the cheeks and the forehead.

Stage 3: inflammatory stage (papularpostular rosacea) with appearance of inflammatory papules and pustules, but without affecting the sebaceous follicles and thus with absence of cysts and comedones.

Stage 4: rhinophyma stage. This late phase essentially affects men. The patients have a bumpy, voluminous red nose with sebaceous hyperplasia and fibrous reordering of the connective tissue.

BPO for treating Rosacea was published in U.S. Pat. No. 9,687,465, US 20170281571 and US 20180147165. Typical treatments of rosacea include oral or topical administration of antibiotics such as tetracyclines, salicylic acid, anti-fungal agents, steroids, metronidazole (an anti-bacterial agent) or with isotretinoin in severe cases, or even with anti-infectious agents such as azelaic acid.

SUMMARY OF THE INVENTION

In some embodiments, this invention provides a microcapsule comprising a core encapsulated by a metal oxide shell, wherein said core comprises solid benzoyl peroxide, wherein said microcapsule prepared by a process comprising:

(a) contacting solid benzoyl peroxide particulate matter, with a first cationic additive being a cationic surfactant, to obtain a dispersion in an aqueous medium, said particulate matter having positive charges on its surface;

(b) adding an aqueous solution comprising metal oxide salt to said dispersion of said particulate matter, under conditions wherein said metal oxide salt precipitates onto the surface of the particulate matter, and acidifying to thereby form a solid, water-insoluble particulate matter that has a metal oxide layer coated thereon;

(c) contacting, in a medium consisting of an aqueous medium, the particulate matter coated with a metal oxide layer of the preceding step with a surface adhering additive being one or both of (i) a second cationic additive being a cationic polymer and (ii) a non-ionic additive, to obtain a dispersion of said coated particulate matter having an adhering additive on the surface thereof in said aqueous medium;

(d) bringing the dispersion obtained in step (c) into contact with an aqueous solution of a sodium silicate, under conditions wherein said metal oxide salt precipitates onto the surface of said coated particulate matter, and acidifying to thereby form a solid, water-insoluble particulate matter that has a further metal oxide layer coated thereon;

(e) repeating steps (c) and (d) between 3-50 times at a temperature of between 28° C. to 40° C.; and (f) optionally, after completion of step (e), aging the dispersion to obtain said encapsulated benzoyl peroxide.

In some embodiments this invention provides a suspension comprising microcapsules comprising a core encapsulated by a metal oxide shell, wherein said core comprises solid benzoyl peroxide, wherein said microcapsules are prepared by a process described above (steps a-f), wherein the dissolution rate of the BPO is less than 60% weight/h as measured in a medium of a 55%:45% mixture of water and acetonitrile at ambient temperature.

In some embodiments, this invention provides a pharmaceutical composition comprising microcapsules comprising a core encapsulated by a metal oxide shell, wherein said core comprises solid benzoyl peroxide, wherein said microcapsules are prepared by a process described above (steps a-f), and a pharmaceutically acceptable carrier or excipient.

In some embodiments, this invention provides a pharmaceutical composition comprising microcapsules comprising a core encapsulated by a metal oxide shell, wherein said core comprises solid benzoyl peroxide, wherein said microcapsules are prepared by a process described above (steps a-f), and a pharmaceutically acceptable carrier or excipient wherein the microcapsules have microencapsulation efficiency of at least 75%, preferably at least 85%, more preferably at least 90%.

In some embodiments this invention provides a pharmaceutical composition comprising a suspension comprising microcapsules comprising a core encapsulated by a metal oxide shell, wherein said core comprises solid benzoyl peroxide, wherein said microcapsules are prepared by a process described above (steps a-f), wherein the dissolution rate of the BPO is less than 60% weight/h as measured in a medium of a 55%:45% mixture of water and acetonitrile at ambient temperature.

In some embodiments, this invention provides a pharmaceutical composition comprising microcapsules comprising tretinoin or a pharmaceutically acceptable salt thereof in an amount of about 0.1% by weight of said composition and microcapsules comprising benzoyl peroxide in an amount of between 3% by weight of said composition; and a pharmaceutically acceptable carrier or excipient, wherein the microcapsules comprising tretinoin comprise a core encapsulated by a shell, wherein said core comprises tretinoin in a solid form; wherein the microencapsulation efficiency of the tretinoin is at least 90%; and wherein the microcapsules comprising benzoyl peroxide are prepared according to the process described above (steps a-f). In other embodiments, the tretinoin is at a concentration of above 14% w/w within the core of its microcapsule.

In some embodiments, this invention provides a pharmaceutical composition comprising microcapsules comprising benzoyl peroxide in an amount of between 3% by weight of said composition and wherein the microcapsules comprising benzoyl peroxide are prepared according to the process described above (steps a-f); and the composition further comprises microcapsules comprising tretinoin or a pharmaceutically acceptable salt thereof in an amount of about 0.1% by weight of said composition; and a pharmaceutically acceptable carrier or excipient, wherein the microcapsules comprising tretinoin or a pharmaceutically acceptable salt thereof comprise a core encapsulated by a shell, wherein said core comprises a dispersion, wherein said dispersion comprises:

an oil phase comprising tretinoin in a solid form at a concentration of above 14% w/w in said oil phase; and optionally at least one phase changing material;

wherein said at least one phase changing material is added to said dispersion, wherein said at least one phase changing material is not liquid at room temperature.

In other embodiments, the tretinoin dissolution rate is between 5% to 35% weight/h as measured in a medium of 30%:70% V/V mixture of water:isopropyl alcohol at 32° C. and wherein the BPO dissolution rate is between 10% to 60% weight/h as measured in a medium of 55%:45% mixture of water:acetonitrile at ambient temperature.

In other embodiments, the microcapsules of the benzoyl peroxide have microencapsulation efficiency of at least 75%, preferably at least 85%, more preferably at least 90%; and the microcapsules of the tretinoin have microencapsulation efficiency of at least 90%.

In some embodiments, this invention provides a pharmaceutical composition comprising the microcapsules of this invention and a pharmaceutically acceptable carrier or excipient.

In some embodiments, this invention provides a method for treating a skin disease, disorder or condition in a subject in need thereof, said method comprising topically administering to said subject the pharmaceutical compositions of this invention.

In other embodiments, the skin disease, disorder or condition is selected from acne, psoriasis, seborrhea, contact dermatitis, rosacea, and any combination thereof. In some embodiments, this invention provides a method for treating a skin disease, disorder or condition in a subject in need thereof, said method comprising topically administering to said subject a pharmaceutical composition comprising a core encapsulated by a metal oxide shell, wherein said core comprises solid benzoyl peroxide, wherein said microcapsule is prepared by a process described above (steps (a-f), wherein said skin disease, disorder or condition is selected from acne, psoriasis, seborrhea, contact dermatitis, rosacea, and any combination thereof. In other embodiments, the skin disease is rosacea. In other embodiments, the microcapsules have microencapsulation efficiency of at least 75%, preferably at least 85%, more preferably at least 90%.

In some embodiments, this invention provides a method for treating a skin disease, disorder or condition in a subject in need thereof, said method comprising topically administering to said subject a pharmaceutical composition comprising a suspension comprising microcapsules, wherein the microcapsule comprises a core encapsulated by a metal oxide shell, wherein said core comprises solid benzoyl peroxide, wherein said microcapsule is prepared by a process described above (steps (a-f), wherein said skin disease, disorder or condition is selected from acne, psoriasis, seborrhea, contact dermatitis, rosacea, and any combination thereof. In other embodiments, the skin disease is rosacea. In other embodiments, the microcapsules have microencapsulation efficiency of at least 75%, preferably at least 85%, more preferably at least 90%.

In some embodiments, this invention provides a method for treating a skin disease, disorder or condition in a subject in need thereof, said method comprising topically administering to said subject a composition comprising microcapsules comprising tretinoin or a pharmaceutically acceptable salt thereof in an amount of about 0.1% by weight of said composition and microcapsules comprising benzoyl peroxide in an amount of between 3% by weight of said composition; and a pharmaceutically acceptable carrier or excipient, wherein the microcapsules comprising tretinoin comprise a core encapsulated by a shell, wherein said core comprises tretinoin in a solid form; wherein the microencapsulation efficiency of the tretinoin is at least 90%; and wherein the microcapsules comprising benzoyl peroxide are prepared according to the process described above (steps a-f); wherein said skin disease, disorder or condition is selected from acne, psoriasis, seborrhea, contact dermatitis, rosacea, and any combination thereof. In other embodiments, the microcapsules have microencapsulation efficiency of at least 75%, preferably at least 85%, more preferably at least 90%.

In some embodiments, this invention provides a method for treating a skin disease, disorder or condition in a subject in need thereof, said method comprising topically administering to said subject a composition comprising a pharmaceutical composition comprising microcapsules comprising benzoyl peroxide in an amount of between 3% by weight of said composition and wherein the microcapsules comprising benzoyl peroxide are prepared according to the process described above (steps a-f); and the composition further comprises microcapsules comprising tretinoin or a pharmaceutically acceptable salt thereof in an amount of about 0.1% by weight of said composition; and a pharmaceutically acceptable carrier or excipient,
wherein the microcapsules comprising tretinoin or a pharmaceutically acceptable salt thereof comprise a core encapsulated by a shell, wherein said core comprises a dispersion, wherein said dispersion comprises:
an oil phase comprising tretinoin in a solid form at a concentration of above 14% w/w in said oil phase; and
optionally at least one phase changing material;
wherein said at least one phase changing material is added to said dispersion, wherein said at least one phase changing material is not liquid at room temperature; wherein said skin disease, disorder or condition is selected from acne, psoriasis, seborrhea, contact dermatitis, rosacea, and any combination thereof.

In some embodiments, this invention provides a method for treating rosacea in a subject in need thereof, said method comprising topically administering to said subject a pharmaceutical composition comprising benzoyl peroxide (BPO) microcapsules of this invention, wherein the microcapsules have microencapsulation efficiency of at least 75%, preferably at least 85%, more preferably at least 90%.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3A is a secondary electron detector (ET) micrograph showing the topography of the different regions of the capsule: The aqueous matrix (asterisk), the capsule (arrow) and the silica shell around it (arrowhead). FIG. 3B is an EsB electron detector micrograph showing oil-rich domains (arrow), the silica shell (arrowhead) and aqueous matrix (asterisk). Lighter domains seen on the organic phase of the capsule could be silica or ice debris.

FIG. 4A is a secondary electron-detector (ET) micrograph showing the topography of the different regions in the capsule. The silica-rich shell (arrowhead) appears thin, uniform and granular. Faceting in the BPO phase (thick arrow) and in the aqueous phase (thin arrow) indicates crystallinity. FIG. 4B is an EsB-detector micrograph of the same area.

FIG. 5A is an SE2 micrograph showing the topography of the fractured capsule, including the granular silica-rich shell (double-arrow), and a fractured BPO crystal in its core (arrow).

FIG. 5B is The ESB signal shows clearly the silica domains. FIG. 5C is The EDS spectrum from the area shown in the micrographs in A and B. The main peaks are labeled and color-coded. The small peak at 1.04 kV corresponds to Na. FIG. 5D is EDS mapping of the elements composing the capsule shown in FIG. 5A and FIG. 5B, based on the spectrum shown in FIG. 5C. The colors correspond to those of the spectrum; the background is an SE2 picture. The core is rich in carbon, the aqueous continuous phase is rich in oxygen, and the capsule shell is rich in silica.

FIG. 7B—EsB detector) of an E-ATRA microcapsule, is a specimen that was over-etched. The ATRA crystals are nicely visible, but since the water in the aqueous phase has completely sublimated, it is difficult to differentiate between free silica and the silica in the capsule shell.

FIG. 9A—An image produced by the ET secondary electron detector of one microcapsule; FIG. 9B—An image produced by the EsB detector displaying the shell thickness of the microcapsule, about 250 nm to about 410 nm.

FIG. 10A—An image produced by the ET secondary electron detector of two microcapsules; FIG. 10B—An image produced by the EsB detector displaying the shell thickness of the microcapsule, about 145 nm to 300 nm and a diameter of about 6 μm for each microcapsule.

FIG. 11A—displays two microcapsules with a diameter of about 5 μm each. FIG. 11B—is a closeup image of the left microcapsule shown in FIG. 11A, displaying the shell thickness of the microcapsule, about 76 nm to about 130 nm.

FIG. 12A—secondary electron image; FIG. 12B—a silicon map; FIG. 12C—an oxygen map; FIG. 12D—a carbon map; FIG. 12E—a full map; FIG. 12F—EDS spectrum from the area shown in the micrographs; the main peaks are labeled and color-coded. Additionally, there is a very small pick around 1.05 keV that designates the position of sodium which corresponds to the existence of sodium in the suspension that is originated from the sodium silicate solution.

FIG. 15A—An image produced by the ET secondary electron showing microcapsule diameter of about 16 μm; FIG. 15B—An image produced by the EsB detector displaying the shell thickness of the microcapsule, about 1.7 μm.

FIG. 16A—displays a microcapsule with a diameter of about 17.5 μm. FIG. 16B—is a closeup image of the microcapsule shown in FIG. 16A, displaying the shell thickness of the microcapsule, about 185 nm to about 1.2 μm.

FIG. 17B—is a closeup image of the microcapsule shown in FIG. 17A, displaying the shell thickness of the microcapsule, about 56 nm to about 97 nm.

FIG. 18A-secondary electron image; FIG. 18B—a silicon map; FIG. 18C—an oxygen map; FIG. 18D—a carbon map; FIG. 18E—a full map; FIG. 18F—EDS spectrum from the area shown in the micrographs; the main peaks are labeled and color-coded.

DETAILED DESCRIPTION OF THE INVENTION

Encapsulated ATRA (E-ATRA) Microcapsules

Figure 1:
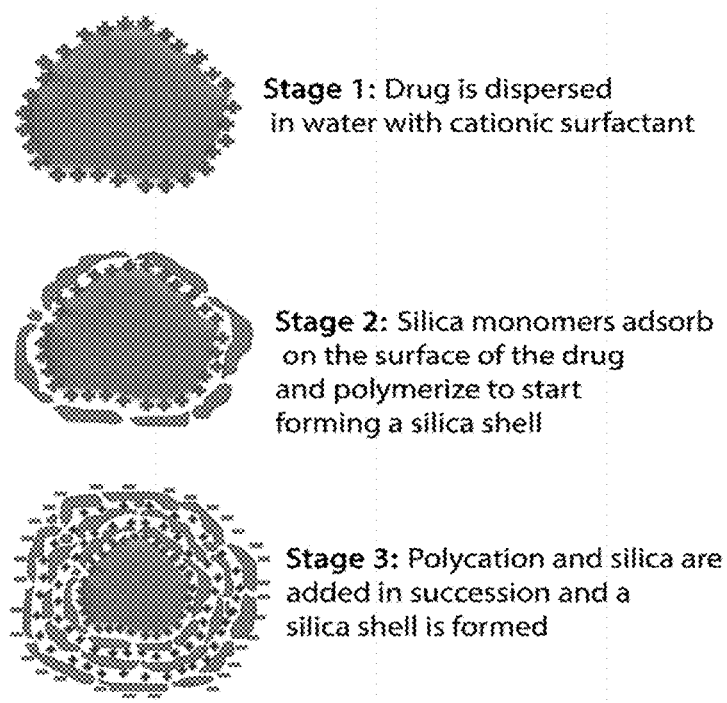
FIG. 1 Illustration of the BPO microencapsulation process.

In one embodiment, this invention provides a microcapsule comprising a core encapsulated by a shell, wherein said core comprises a dispersion, wherein said dispersion comprises:
  an oil phase comprising tretinoin in a solid form at a concentration of above 14% w/w in said oil phase; and optionally at least one phase changing material;
  wherein said at least one phase changing material is added to said dispersion, wherein said at least one phase changing material is not liquid at room temperature.

In some embodiments, this invention provides a microcapsule comprising a core encapsulated by a shell, wherein said core comprises a dispersion, wherein said dispersion comprises:
  an oil phase comprising tretinoin in a solid form at a concentration of above 14% w/w in said oil phase; and optionally at least one phase changing material;
  wherein said at least one phase changing material is added to said dispersion, wherein said at least one phase changing material is not liquid at room temperature, and wherein the tretinoin dissolution rate is between 5% to 35% weight/h as measured in a medium of 30%:70% V/V mixture of water: isopropyl alcohol at about 32° C.

In some embodiments, this invention provides a microcapsule comprising a core encapsulated by a shell, wherein said core comprises a dispersion, wherein said dispersion comprises:
  an oil phase comprising tretinoin in a solid form at a concentration of above 14% w/w in said oil phase; and optionally at least one phase changing material;
  wherein said at least one phase changing material is added to said dispersion, wherein said at least one phase changing material is not liquid at room temperature; and wherein said microcapsule is stable for a period of between about 2 weeks to about 2 years at room temperature.

In some embodiments, this invention provides a microcapsule comprising encapsulated ATRA of this invention, wherein the shell is a silicon dioxide shell, and said microcapsule is prepared by a process comprising:
  a. preparing an oil phase comprising:
    mixing an oil medium with at least one antioxidant, a silica precursor and tretinoin to form an oil phase, wherein the concentration of the tretinoin in the oil phase is at least 14% w/w;
    optionally, milling said oil phase;
    optionally adding a phase changing material to said oil phase;
  b. preparing an aqueous phase comprising mixing a surfactant and water;
  c. preparing a sodium silicate solution comprising dissolving silicon dioxide and an inorganic base in water;
  d. adding said oil phase to said aqueous phase to form an emulsion;
  e. adding said sodium silicate solution to said emulsion;
  f. adding acidic solution to said emulsion; and adjusting the pH to between 3.9 to 4.2;

forming a core comprising a dispersion of tretinoin encapsulated by a silicon dioxide shell.

In some embodiments, the thickness of said metal oxide shell of the microcapsules of this invention comprising encapsulated ATRA is ranging between 50 nm and 5000 nm. In other embodiments, the thickness of metal oxide shell is ranging between 50 nm and 4000 nm. In other embodiments, the thickness of metal oxide shell is ranging between 50 nm and 3000 nm. In other embodiments, the thickness of metal oxide shell is ranging between 50 nm and 2000 nm. In other embodiments, the thickness of metal oxide shell is ranging between 50 nm and 1000 nm. In other embodiments, the thickness of metal oxide shell is ranging between 100 nm and 1000 nm. In other embodiments, the thickness of metal oxide shell is ranging between 200 nm and 5000 nm. In other embodiments, the thickness of metal oxide shell is ranging between 500 nm and 5000 nm. In other embodiments, the thickness of metal oxide shell is ranging between 1000 nm and 5000 nm.

In some embodiments, the diameter of the microcapsule comprising encapsulated ATRA of this invention includes the diameter size of both the core and the shell. In other embodiments, the average diameter of said microcapsule is in the range of between 5 micrometers and 50 micrometers. In other embodiments, the average diameter of said microcapsule is in the range of between 5 micrometers and 40 micrometers. In other embodiments, the average diameter of said microcapsule is in the range of between 5 micrometers and 30 micrometers. In other embodiments, the average diameter of said microcapsule is in the range of between 5 micrometers and 20 micrometers. In other embodiments, the average diameter of said microcapsule is in the range of between 5 micrometers and 10 micrometers.

In some embodiments, the concentration of the tretinoin in an oil phase used in the microcapsules comprising encapsulated ATRA and used in the process of preparation of said microcapsules is above 14% by weight. In another embodiments, the concentration of the tretinoin in said oil phase is between 15% to 25% by weight. In other embodiments, the concentration of the tretinoin in said oil phase is between 17% to 25% by weight. In other embodiments, the concentration of the tretinoin in said oil phase is between 18% to 25% by weight. In other embodiments, the concentration of the tretinoin in said oil phase is between 19% to 25% by weight. In other embodiments, the concentration of the tretinoin in said oil phase is between 20% to 25% by weight.

In some embodiments, the microcapsules of this invention and process of preparation thereof comprise encapsulated tretinoin (ATRA) and optionally at least one phase changing material (PCM). In other embodiments, the at least one phase changing material is selected from the group consisting of natural or synthetic paraffin (e.g. having a molecular formula of $C_nH_{2n+2}$, wherein n=10-100), $C_{10}$-$C_{100}$ alkane, $C_{10}$-$C_{100}$ alkene (having at least one double bond), $C_{10}$-$C_{100}$ alkyne (having at least one triple bond), waxes, aliphatic alcohols (e.g. having a molecular formula of $CH_3(CH_2)_nOH$, wherein n=10-100), fatty acids (e.g. having a molecular formula of $CH_3(CH_2)_nCOOH$, wherein n-10-100), and any combination thereof.

In some embodiments, said at least one phase changing material is at least one natural or synthetic paraffin. In some embodiments, said at least one phase changing material is a $C_{10}$-$C_{100}$ aliphatic alcohol (in other embodiments $C_{10}$, $C_{20}$, $C_{30}$, $C_{40}$, $C_{50}$, $C_{60}$, $C_{70}$, $C_{80}$, $C_{90}$ to $C_{100}$ aliphatic alcohol). In further embodiments, said at least one phase changing material is a $C_{10}$-$C_{100}$ aliphatic fatty acid (in other embodiments $C_{10}$, $C_{20}$, $C_{30}$, $C_{40}$, $C_{50}$, $C_{60}$, $C_{70}$, $C_{80}$, $C_{90}$ to $C_{100}$ aliphatic fatty acid).

In one embodiment said PCMs are liquified (or at least become substantially or partially liquified, pliable or semi-solid, and capable of being handled by a process of the invention) at a temperature range of between about 35° C. to about 60° C., more preferably in a temperature range of between about 35° C. to about 45° C.

Examples of phase changing materials for use in the microcapsules of this invention and being used by the processes of the invention include, but are not limited to: Carnauba wax (m.p. 82-86° C.), Beeswax pure (m.p. 61-65° C.), Beeswax white pure, (m.p. 61-65° C.), Beeswax bleached technical (m.p. 61-65° C.), Montan wax bleached (m.p. 80-86° C.), Montan wax bleached, partially saponified (m.p. 99-105° C.), Montanic acid (m.p. 81-87° C.), Hydrocarbon wax synthetic (m.p. 106-114° C.), Microcrystalline wax (m.p. 89-95° C.), Microcrystalline wax (m.p. 76-82° C.), Hardwax partially saponified (m.p. 104-109° C.), Beeswax yellow (m.p. 61-66° C.), Polishing Wax (m.p. 78-84° C.), Castor wax (m.p. 83-89° C.), Microwax (m.p. 89-95° C.), Microwax (m.p. 80-86° C.), Microwax (m.p. 76-82° C.), Ozokerite (m.p. 72-79° C.), Microcrystalline wax, plastic (m.p. 76-82° C.), Microcrystalline wax, soft (m.p. 74-80° C.), Wax blend (m.p. 62-68° C.), Polyolefin wax (m.p. 65-75° C.), Lanolin, Shellac, Bayberry wax (m.p. 45° C.), Candelilla wax (m.p. 67-79° C.), Ouricury wax, Rice bran wax (m.p. 77-86° C.), Soy candle (wax), Paraffin (m.p. 47-64° C.), Chinese wax, and any combinations thereof.

In some embodiments the viscosity of said core/core material of said microcapsule (at room temperature) may be about 300 cP, 350 cP, 400 cP, 450 cP, 500 cP, 550 cP, 600 cP, 650 cP, 700 cP, 750 cP, 800 cP, 900 cP, 1000 cP, 2000 cP, 3000 cP, 4000 cP, 5000 cP, 6000 cP, 7000 cP, 8000 cP, 9000 cP, 10,000 cP, 20,000 cP, 30,000 cP, 40,000 cP, 50,000 cP, 60,000 cP, 70,000 cP, 80,000 cP, 90,000 cP, 100,000 cP, 200,000 cP, 300,000 cP, 400,000 cP, 500,000 cP, 600,000 cP, 700,000 cP, 800,000 cP, 900,000 cP or 1,000,000 cP (when measured under various conditions). In some embodiments, the viscosity of said core at room temperature is between about 300 to 600 cP. In other embodiments, the viscosity of said core at room temperature is between about 400 to 500 cP. In further embodiments, the viscosity of said core at room temperature is between about 300 to 10,000 cP. In other embodiments the viscosity of said core at room temperature is between about 5,000 to 1,000,000 cP. In some further embodiments the viscosity of said core at room temperature is between about 20,000 to 1,000,000 cP.

In one embodiment of a process for the preparation of a microcapsule, said at least one phase changing material is in a liquid state. Thus, prior to the addition of said at least one PCM, its temperature is raised until it is substantially homogenously liquified. In a further embodiment of the present invention, a process of the invention is carried out under a temperature wherein said at least one phase changing material is in a liquid state, throughout the entire emulsification and encapsulation process disclosed herein above and below. It is noted that said at least one PCM utilized by a process of the present invention, is selected such that its heat of fusion allows for processes of the invention to be carried out substantially without compromising the active agents used, the emulsion formed and the metal oxide shell produced for the microcapsules of the invention.

In some embodiment, the microcapsules comprising encapsulated ATRA (tretinoin), comprise a dissolution rate of the tretinoin is between 5% to 35% weight/h as measured in a medium of 30%:70% V/V mixture of water:isopropyl alcohol at 32° C. In other embodiment, the dissolution rate of the tretinoin is between 5% to 20% weight/h as measured in a medium of 30%:70% V/V mixture of water:isopropyl alcohol at 32° C. In other embodiment, the dissolution rate of the tretinoin is between 10% to 35% weight/h as measured in a medium of 30%:70% V/V mixture of water:isopropyl alcohol at 32° C. In other embodiment, the dissolution rate of the tretinoin is between 15% to 35% weight/h as measured in a medium of 30%:70% V/V mixture of water:isopropyl alcohol at 32° C.

In some embodiment, the microcapsules comprising encapsulated ATRA (tretinoin), are stable for a period of between about 2 weeks to about 2 years at room temperature. In other embodiments, the microcapsules are stable for a period of between 2 weeks to 6 months. In other embodiments, the microcapsules are stable for a period of between 3 months to 2 years. In another embodiment, the microcapsules are stable for a period of between 3 months to 1 year.

Pharmaceutical Compositions Comprising Encapsulated ATRA (E-ATRA) Microcapsules

In some embodiments, this invention provides a pharmaceutical composition comprising a microcapsule of this invention and a pharmaceutically acceptable carrier or excipient. In some embodiments, this invention provides a pharmaceutical composition comprising a microcapsule comprising encapsulated ATRA and a pharmaceutically acceptable carrier or excipient. In some embodiments, this invention provides a pharmaceutical composition comprising a microcapsule comprising encapsulated ATRA, prepared by the process of this invention and a pharmaceutically acceptable carrier or excipient.

In other embodiments, this invention provides a pharmaceutical composition a microcapsule comprising a core encapsulated by a shell, wherein said core comprises a dispersion, wherein said dispersion comprises:
 an oil phase comprising tretinoin in a solid form at a concentration of above 14% w/w in said oil phase; and
 optionally at least one phase changing material;
wherein said at least one phase changing material is added to said dispersion, wherein said at least one phase changing material is not liquid at room temperature; and wherein said pharmaceutical composition comprises a pharmaceutically acceptable carrier or excipient.

In some embodiments, this invention provides a pharmaceutical composition comprising a microcapsule comprising a core encapsulated by a shell, wherein said core comprises tretinoin in a solid form and wherein the microencapsulation efficiency of the tretinoin is at least 90%. In other embodiments, the core comprises a dispersion, wherein said dispersion comprises:
 an oil phase comprising tretinoin in a solid form at a concentration of above 14% w/w in said oil phase; and
 optionally at least one phase changing material;
wherein said at least one phase changing material is added to said dispersion, wherein said at least one phase changing material is not liquid at room temperature.

In some embodiments, the compositions of this invention comprising a microcapsule comprising a core encapsulated by a shell, wherein said core comprises tretinoin in a solid form and wherein the microencapsulation efficiency of the tretinoin is at least 90%; and/or the core comprises a dispersion, wherein said dispersion comprises:
 an oil phase comprising tretinoin in a solid form at a concentration of above 14% w/w in said oil phase; and
 optionally at least one phase changing material;
wherein said at least one phase changing material is added to said dispersion, wherein said at least one phase changing material is not liquid at room temperature; and/or wherein after two weeks storage at 40° C. and 75% relative humidity a concentration of all-trans 5,6-epoxy retinoic acid is less than 1% by weight of the initial tretinoin amount prior to storage.

In some embodiment, the pharmaceutical composition comprising microcapsules comprising encapsulated ATRA of this invention comprises a microencapsulation efficiency of the tretinoin of at least 90%. In other embodiment, the microencapsulation efficiency of the tretinoin is between 90% to 100%. In other embodiment, the microencapsulation efficiency of the tretinoin is between 90% to 99%. In other embodiment, the microencapsulation efficiency of the tretinoin is between 90% to 98%. In other embodiment, the microencapsulation efficiency of the tretinoin is between 95% to 100%. In other embodiment, the microencapsulation efficiency of the tretinoin is between 96% to 100%. In other embodiment, the microencapsulation efficiency of the tretinoin is between 97% to 100%. In other embodiment, the microencapsulation efficiency of the tretinoin is between 98% to 100%.

In other embodiments, the tretinoin is at a concentration of above 14% w/w within the core.

In other embodiments, encapsulated tretinoin having microencapsulation efficiency of at least 90% may be prepared as described herein or by an encapsulation materials/general disclosure disclosed in the following publications (incorporated herein by reference): U.S. Pat. Nos. 9,682,031, 7,629,394, 9,205,395, US 2015/0328615, US 2014/0186630. Controlled release microcapsules: IN01958CH2007, IN02080CH2007, U.S. Pat. Nos. 4,235,872, 4,670,250, EP 0248531, U.S. Pat. Nos. 4,970,031, 5,238,714, WO9321764, U.S. Pat. No. 5,575,987, WO9420075, US 2004/137031, US 2006/003014, US 2010/180464.

In some embodiments, after two weeks storage at 40° C. and 75% relative humidity of the composition comprising E-ARTA of this invention, a concentration of all-trans 5,6-epoxy retinoic acid is less than 1% by weight of the initial tretinoin amount prior to storage. In other embodiments, a concentration of all-trans 5,6-epoxy retinoic acid is less than 0.7%. In some embodiments the degradation of the tretinoin from the composition of this invention is less than 2.5% after two weeks storage at 40° C. and 75% relative humidity. In another embodiment, the degradation of said tretinoin is less than 2% after two weeks storage at 40° C. and 75% relative humidity.

Process for the Preparation of Encapsulated ATRA (E-ATRA) Microcapsules

In some embodiments, this invention provides a process for the preparation of a microcapsule comprising encapsulated ATRA, the process comprises:
 a. preparing an oil phase comprising:
  mixing an oil medium with at least one antioxidant, a silica precursor and tretinoin to form an oil phase, wherein the concentration of the tretinoin in the oil phase is at least 14% w/w;
  optionally, milling said oil phase;
  optionally adding a phase changing material to said oil phase;

b. preparing an aqueous phase comprising mixing a surfactant and water;
c. preparing a sodium silicate solution comprising dissolving silicon dioxide and an inorganic base in water;
d. adding said oil phase to said aqueous phase to form an emulsion;
e. adding said sodium silicate solution to said emulsion;
f. adding acidic solution to said emulsion; and adjusting the pH to between 3.9 to 4.2;
    forming a core comprising a dispersion of tretinoin encapsulated by a silicon dioxide shell.

In some embodiments, the silica precursor (sol-gel precursor) used in the process for the preparation of the microcapsule comprising encapsulated ATRA is selected from tetramethoxysilane (also known as tetramethyl orthosilicate or TMOS), tetraethoxysilane (also known as tetraethyl orthosilicate or TEOS), dimethyldimethoxysilane, methyltrimethoxysilane, diethyldimethoxysilane, and sodium silicate.

In some embodiments, the sol-gel precursor can be selected from a silicon alkoxide monomer; a silicon ester monomer; a monomer of the formula $Si(R)_n(P)_m$, wherein R can be a hydrolyzable substituent, n can be an integer from 2 to 4, P can be a non polymerizable substituent, and m can be an integer from 0 to 4; a partially hydrolyzed and partially condensed polymer of any of the above, and mixtures of any of the above. Non-limiting examples of silicon alkoxide monomer include tetramethoxy silane, tetraethoxy silane, and combinations thereof. Non-limiting examples of monomers of the formula $Si(R)_n(P)_m$ include methyl trimethoxysilane, dimethyl dimethoxysilane, and combinations thereof.

In some embodiments, the antioxidant used in the process for the preparation of the microcapsule comprising encapsulated ATRA is butylated hydroxyanisole (BHA), butylated hydroxytoluene (BHT) and tert-butyl hydroquinone (TBHQ) or combination thereof. In some embodiments, the antioxidant used in the process for the preparation of the microcapsule comprising encapsulated ATRA is butylated hydroxytoluene (BHT).

In some embodiments, the oil-medium used in the process for the preparation of the microcapsule comprising encapsulated ATRA is squalene oil, polydimethylsiloxane, mineral oil, castor oil, aromatic 200, and mixtures thereof.

In some embodiments, the surfactant used in the process for the preparation of the microcapsule comprising encapsulated ATRA is selected from a cationic surfactant, an anionic surfactant, a non-ionic surfactant and mixtures thereof. In one embodiment the at least one surfactant is a cationic surfactant. In a further embodiment said at least one cationic surfactant is cetyltrimethyl ammonium chloride (CTAC).

In another embodiment the surfactant may comprise a hydrophobic surfactant, hydrophobic polymeric surfactant, or mixtures thereof. In one embodiment the hydrophobic surfactant or hydrophobic polymeric surfactant is a non-ionic surfactant. The hydrophilic surfactant may be for example an anionic, a cationic, a non-ionic surfactant, or mixtures thereof.

In some embodiments the concentration of the cationic surfactant in the aqueous phase may be from 0.1 to 5% (w/w), in other embodiments from 1 to 5% (w/w). It is appreciated that the concentration of the surfactant will also depend on the percentage of the oily phase and aqueous phase. In some embodiments the concentration of the surfactant may be 5-10% (w/w) from the weight of the oily phase.

In some embodiments, the at least one phase changing material used in the process for the preparation of the microcapsule comprising encapsulated ATRA is selected from the group consisting of natural or synthetic paraffin (e.g. having a molecular formula of $C_nH_{2n+2}$, wherein n=10-100), $C_{10}$-$C_{100}$ alkane, $C_{10}$-$C_{100}$ alkene (having at least one double bond), $C_{10}$-$C_{100}$ alkyne (having at least one triple bond), waxes, aliphatic alcohols (e.g. having a molecular formula of $CH_3(CH_2)_nOH$, wherein n=10-100), fatty acids (e.g. having a molecular formula of $CH_3(CH_2)_nCOOH$, wherein n-10-100), and any combination thereof. In some embodiments, the at least one phase changing material used in the process for the preparation of the microcapsule comprising encapsulated ATRA white beeswax In some embodiment, the process for the preparation of microcapsules comprising encapsulated ATRA, and the microcapsules prepared by said process, comprise a silica precursor comprising TEOS, or an antioxidant comprising butylated hydroxytoluene, or a oil medium comprising squalene oil, or a phase changing material comprising a white beeswax, or a surfactant comprising cetrimonium chloride, or any combination thereof.

In some embodiments, the microcapsules prepared by the process for the preparation of microcapsules comprising encapsulated ATRA have microencapsulation efficiency of at least 90%. In other embodiment, the microencapsulation efficiency of the tretinoin is between 90% to 100%. In other embodiment, the microencapsulation efficiency of the tretinoin is between 90% to 99%. In other embodiment, the microencapsulation efficiency of the tretinoin is between 90% to 98%. In other embodiment, the microencapsulation efficiency of the tretinoin is between 95% to 100%. In other embodiment, the microencapsulation efficiency of the tretinoin is between 96% to 100%. In other embodiment, the microencapsulation efficiency of the tretinoin is between 97% to 100%. In other embodiment, the microencapsulation efficiency of the tretinoin is between 98% to 100%.

In some embodiments, the metal oxide shell thickness of the microcapsules prepared by the process for the preparation of microcapsules comprising encapsulated ATRA is ranging between 50 nm and 5000 nm.

In some embodiments, the average diameter of the microcapsules prepared by the process for the preparation of microcapsules comprising encapsulated ATRA, is ranging between 5 micrometers and 50 micrometers.

In some embodiment, the microcapsules comprising encapsulated ATRA (tretinoin), prepared by the process described herein have a tretinoin dissolution rate of between 5% to 35% weight/h as measured in a medium of 30%:70% V/V mixture of water:isopropyl alcohol at 32° C. In other embodiment, the dissolution rate of the tretinoin is between 5% to 20% weight/h as measured in a medium of 30%:70% V/V mixture of water:isopropyl alcohol at 32° C. In other embodiment, the dissolution rate of the tretinoin is between 10% to 35% weight/h as measured in a medium of 30%:70% V/V mixture of water:isopropyl alcohol at 32° C. In other embodiment, the dissolution rate of the tretinoin is between 15% to 35% weight/h as measured in a medium of 30%:70% V/V mixture of water:isopropyl alcohol at 32° C.

In some embodiment, the microcapsules comprising encapsulated ATRA (tretinoin), prepared by the process described herein are stable for a period of between about 2 weeks to about 2 years at room temperature. In other embodiments, the microcapsules are stable for a period of between 2 weeks to 6 months at room temperature. In other embodiments, the microcapsules are stable for a period of between 3 months to 2 years at room temperature. In another embodiment, the microcapsules are stable for a period of between 3 months to 1 year at room temperature.

Encapsulated Benzoyl Peroxide (E-BPO) Microcapsules

In some embodiments, this invention provides a microcapsule comprising a core encapsulated by a metal oxide shell, wherein said core comprises solid benzoyl peroxide, wherein said microcapsule prepared by a process comprising:
 (a) contacting solid benzoyl peroxide particulate matter, with a first cationic additive being a cationic surfactant, to obtain a dispersion in an aqueous medium, said particulate matter having positive charges on its surface;
 (b) adding an aqueous solution comprising metal oxide salt to said dispersion of said particulate matter, under conditions wherein said metal oxide salt precipitates onto the surface of the particulate matter, and acidifying to thereby form a solid, water-insoluble particulate matter that has a metal oxide layer coated thereon;
 (c) contacting, in a medium consisting of an aqueous medium, the particulate matter coated with a metal oxide layer of the preceding step with a surface adhering additive being one or both of (i) a second cationic additive being a cationic polymer and (ii) a non-ionic additive, to obtain a dispersion of said coated particulate matter having an adhering additive on the surface thereof in said aqueous medium;
 (d) bringing the dispersion obtained in step (c) into contact with an aqueous solution of a sodium silicate, under conditions wherein said metal oxide salt precipitates onto the surface of said coated particulate matter, and acidifying to thereby form a solid, water-insoluble particulate matter that has a further metal oxide layer coated thereon;
 (e) repeating steps (c) and (d) between 3-50 times at a temperature of between 28° C. to 40° C.; and
 (f) optionally, after completion of step (e), aging the dispersion to obtain said encapsulated benzoyl peroxide.

In other embodiments, the microcapsule according the cationic surfactant used in the process for the preparation of E-BPO microcapsules is CTAC or wherein said cationic polymer is PDAC, or a combination thereof. In some embodiments, the cationic polymer (of the first cationic additive or second cationic additive) is selected from poly (ethyleneimine) (PEI), poly(dimethyldiallylannnonium chloride) (PDAC), poly(acrylamide-co-diallyl-di methyl ammonium chloride) (polyquaternium-7), poly(allylamine hydrochloride) (PAH), chitosan, polylysine, and mixtures thereof. In some embodiments, the second cationic polymer may also be a copoly-mer of non-ionic and ionic monomers such as pyrrolidone/dimethylaminoethyl methacylate copolymer.

In some embodiments, the non-ionic additive used in the process is preferably a non-ionic polymer. The non-ionic polymer may be for example polyvinylalcohol, polyvinylpyrrolidone, and mixtures thereof.

In other embodiments, the process for the preparation of E-BPO microcapsules comprises repeating steps (c) and (d) between 3-50 times at a temperature of between 28° C. to 40° C. [step (e)]. In other embodiments, repeating steps (c) and (d) between 5-7 times. In other embodiments, repeating steps (c) and (d) between 5-10 times. In other embodiments, repeating steps (c) and (d) between 10-20 times. In other embodiments, repeating steps (c) and (d) between 10-30 times. In other embodiments, repeating steps (c) and (d) between 20-50 times.

In other embodiments, the acidifying step, in step (b) in the process for the preparation of E-BPO microcapsules, comprises addition of an acidic solution comprising at least one weak acid and said metal oxide salt is a silicate salt. In other embodiments, the weak acid comprises citric acid, lactic acid or mixture thereof.

The ionic additives (such as a first cationic additive) used in step (a) of the process have a dual effect: to form positive charges on the surface of the particulate matter as will be described below, and also to serve as a wetting agent, thus allowing dispersion of the particulate matter as discrete core particles, where each core particle is individually suspended in the aqueous medium.

Step (a) of the process may be conducted for example by (i) contacting the particulate matter with dry ionic additives and then suspending both in an aqueous medium to obtain a dispersion of said particulate matter having positive charges on its surface, or alternatively by (ii) suspending the solid BPO particulate in an aqueous medium comprising ionic additives to obtain a dispersion of said particulate matter having positive charges on its surface.

The concentration of the cationic additives in the dispersion can be about 0.001% to about 30%, in some embodiments about 0.01% to about 10% w/w and in some other embodiments about 0.1% up to about 5% w/w.

The solid content of the water dispersion can be about 0.1% to about 80% w/w, in some embodiments about 1% to about 60% w/w, in some further embodiments about 3% to about 50% w/w.

The purpose of step (a) is to modify the electrical charge of the particulate matter by using ionic additives such that it will be made reactive to the attachment of the metal oxide layer.

For preparing the core material of the particles, the particulate matter ought to be suitably coated with the cationic additive, such that it can be attached to the precipitated metal oxide salt.

The particulate matter is contacted with a cationic additive, for example by mixing it with a solution of a cationic surfactant. The coating need not be continuous. It is sufficient that there is at least a monolayer of the cationic additive. This monolayer will then serve as an anchor for the attachment of the metal oxide layer. In some embodiments, there is a uniform distribution of the monolayer on the core surface so that as the metal oxide layer builds up it will bridge over and be firmly attached to the core.

According to some embodiments said first and said second cationic additive are the same.

According to another embodiment said first and said second cationic additive are different.

In some other embodiments, the first cationic additive is cationic surfactant and the second cationic additive is a cationic polymer.

According to further embodiments, the first cationic additive is a cationic surfactant and the additive in step (c) is a non-ionic additive (e.g. a non-ionic polymer).

In some further embodiments, the coated particulate matter and the second cationic additive are mixed, and most preferable said mixing is under vigorous stirring (e.g. mixer speed above 1000 rpm).

According to a preferred embodiment of the present invention the process further comprising following step (d):
(e) separating the coated particulate matter from the aqueous medium and optionally rinsing and re-dispersing the coated particulate matter in an aqueous medium.

In some embodiments, the separation of the coated particulate matter is conducted by a method such as filtration, centrifugation, decantation, dialysis, or by evaporation of the aqueous medium.

The purpose of the pH adjustment of the dispersion to a value higher than the isoelectric point of the metal oxide is to form negatively charged metal oxide on the particulate matter surface that will be bound to the positive charges of the second cationic additive thus enabling the attachment of the second cationic additive to the surface of the particulate matter.

The non-ionic additive is of a kind that adheres to the surface ("surface-adherent"). An example is a non-ionic polymer. The non-ionic additive may be used alone or in addition to the second cationic surfactant. Without wishing to be bound by theory, the surface-adherent property may be through hydrogen-binding groups such as hydroxyl or amine groups. This allows adhesion of a further layer of metal oxide on the preceding precipitated metal oxide layer.

In some embodiments, the particulate matter/metal oxide salt weight ratio, is about 5,000/1 to about 20/1, in some embodiments about 5,000/1 to about 30/1, or about 5,000/1 to about 40/1, in some further embodiments about 1,000/1 to about 40/1, and in yet some further embodiments about 500/1 to about 80/1.

In some embodiments, the particulate matter/second cationic additive ratio, in step (c) is about 25,000/1 to about 50/1, preferably about 5,000/1 to about 100/1, and most preferably about 2000/1 to about 200/1.

The purpose of aging in step (f) is to obtain a strengthened and denser layer of metal oxide. The aging step is optionally conducted at the end of the process. Most preferably aging is not conducted between repeated coating steps, but only at the end of the process. Upon completion of aging, the separation (e.g. filtration, centrifugation or decantation) will be easy to perform (due to the hard metal oxide layer formed) and the obtained cake or concentrated dispersion will be easily re-dispersed in an aqueous medium to form a dispersion of particles. The aging may be conducted at a temp of 4-90° C., in another embodiment at a temperature of 15-60° C. In another embodiment, at a temperature 20° C.-40° C. for a period of between 2-96 h. In another embodiment, the aging is 2 h, 8 h, 12 h, 24 h, 36 h, 48 h or 96 h each represents a separate embodiment of this invention, or ranges between thereof.

In some embodiments, the average diameter of the E-BPO microcapsules prepared by the process described herein is less than 50 micrometers. In other embodiments between 10-30 micrometers. In other embodiments between 5-25 micrometers. In other embodiments between 10-40 micrometers. In other embodiments between 20-50 micrometers. In other embodiments between 3-50 micrometers. In other embodiments between 10-50 micrometers.

In some embodiments, the thickness of the metal oxide shell of the E-BPO microcapsules prepared by the process described herein ranges between 25-3000 nm. In other embodiments, the thickness of the metal oxide shell of the E-BPO microcapsules is between 25-1000 nm. In other embodiments, the thickness of the metal oxide shell of the E-BPO microcapsules is between 25-2000 nm. In other embodiments, the thickness of the metal oxide shell of the E-BPO microcapsules is between 100-1000 nm. In other embodiments, the thickness of the metal oxide shell of the E-BPO microcapsules is between 500-2000 nm. In other embodiments, the thickness of the metal oxide shell of the E-BPO microcapsules is between 1000-4000 nm.

In some embodiments, the E-BPO microcapsules prepared by the process described herein are stable for a period of between about 2 weeks to about 3 years at room temperature. In other embodiments, the microcapsules are stable for a period of between 2 weeks to 6 months at room temperature. In other embodiments, the microcapsules are stable for a period of between 3 months to 2 years at room temperature. In another embodiment, the microcapsules are stable for a period of between 3 months to 1 year at room temperature.

In some embodiments, this invention provides a suspension comprising the E-BPO microcapsules of this invention. In other embodiments, this invention provides a suspension comprising the E-BPO microcapsules of this invention, wherein the benzoyl peroxide dissolution rate is less than 60% weight/h as measured in a medium of a 55%:45% mixture of water and acetonitrile at ambient temperature.

Pharmaceutical Composition Comprising Encapsulated Benzoyl Peroxide (E-BPO) Microcapsules In some embodiment, this invention provides a pharmaceutical composition comprising E-BPO microcapsules according to this invention, and a pharmaceutically acceptable carrier or excipient. In other embodiments the microcapsules have microencapsulation efficiency of at least 75%, preferably at least 85%, more preferably at least 90%.

In some embodiment, this invention provides a pharmaceutical composition comprising a suspension comprising E-BPO microcapsules of this invention, and a pharmaceutically acceptable carrier or excipient. In other embodiments the microcapsules have microencapsulation efficiency of at least 75%, preferably at least 85%, more preferably at least 90%.

In other embodiments, encapsulated benzoyl peroxide having microencapsulation efficiency of at least 75% may be prepared as described herein or by an encapsulation materials/general disclosure disclosed in the following publications (incorporated herein by reference): U.S. Pat. Nos. 9,682,031, 7,629,394, 9,205,395, US 2015/0328615, US 2014/0186630. Controlled release microcapsules: IN01958CH2007, IN02080CH2007, U.S. Pat. Nos. 4,235,872, 4,670,250, EP 0248531, U.S. Pat. Nos. 4,970,031, 5,238,714, WO9321764, U.S. Pat. No. 5,575,987, WO9420075, US 2004/137031, US 2006/003014, US 2010/180464.

Pharmaceutical Composition Comprising E-BPO Microcapsules and E-ATRA Microcapsules In some embodiments, this invention provides a pharmaceutical composition comprising (i) microcapsules comprising tretinoin or a pharmaceutically acceptable salt thereof in an amount of about 0.1% by weight of said composition and (ii) microcapsules comprising benzoyl peroxide in an amount of about 3% by weight of said composition; and a pharmaceutically acceptable carrier or excipient, wherein the microcapsules comprising tretinoin or a pharmaceutically acceptable salt thereof comprise a core encapsulated by a shell, wherein said core comprises a dispersion, wherein said dispersion comprises:

an oil phase comprising tretinoin in a solid form at a concentration of above 14% w/w in said oil phase; and
optionally at least one phase changing material;
wherein said at least one phase changing material is added to said dispersion, wherein said at least one phase changing material is not liquid at room temperature.

In some embodiments, this invention provides a pharmaceutical composition comprising microcapsules comprising tretinoin or a pharmaceutically acceptable salt thereof in an amount of about 0.1% by weight of said composition and microcapsules comprising benzoyl peroxide in an amount of between 3% by weight of said composition; and a pharmaceutically acceptable carrier or excipient, wherein the microcapsules comprising tretinoin or a pharmaceutically acceptable salt thereof comprise a core encapsulated by a shell, wherein said core comprises a dispersion, wherein said dispersion comprises:

an oil phase comprising tretinoin in a solid form at a concentration of above 14% w/w in said oil phase; and optionally at least one phase changing material;

wherein said at least one phase changing material is added to said dispersion, wherein said at least one phase changing material is not liquid at room temperature; and wherein the microcapsules comprising benzoyl peroxide are prepared by a process comprising:

(a) contacting solid benzoyl peroxide particulate matter, with a first cationic additive being a cationic surfactant, to obtain a dispersion in an aqueous medium, said particulate matter having positive charges on its surface;

(b) adding an aqueous solution comprising metal oxide salt to said dispersion of said particulate matter, under conditions wherein said metal oxide salt precipitates onto the surface of the particulate matter, and acidifying to thereby form a solid, water-insoluble particulate matter that has a metal oxide layer coated thereon;

(c) contacting, in a medium consisting of an aqueous medium, the particulate matter coated with a metal oxide layer of the preceding step with a surface adhering additive being one or both of (i) a second cationic additive being a cationic polymer and (ii) a non-ionic additive, to obtain a dispersion of said coated particulate matter having an adhering additive on the surface thereof in said aqueous medium;

(d) bringing the dispersion obtained in step (c) into contact with an aqueous solution of a sodium silicate, under conditions wherein said metal oxide salt precipitates onto the surface of said coated particulate matter, and acidifying to thereby form a solid, water-insoluble particulate matter that has a further metal oxide layer coated thereon;

(e) repeating steps (c) and (d) between 3-50 times at a temperature of between 28° C. to 40° C.; and optionally, after completion of step (e), aging the dispersion to obtain encapsulated benzoyl peroxide (E-BPO).

In some embodiments, this invention provides a pharmaceutical composition comprising microcapsules comprising tretinoin or a pharmaceutically acceptable salt thereof in an amount of about 0.1% by weight of said composition and microcapsules comprising benzoyl peroxide in an amount of between 3% by weight of said composition; and a pharmaceutically acceptable carrier or excipient, wherein the microcapsules comprising tretinoin comprise a core encapsulated by a shell, wherein said core comprises tretinoin in a solid form; wherein the microencapsulation efficiency of the tretinoin is at least 90%; and wherein the microcapsules comprising benzoyl peroxide are prepared by a process comprising:

(a) contacting solid benzoyl peroxide particulate matter, with a first cationic additive being a cationic surfactant, to obtain a dispersion in an aqueous medium, said particulate matter having positive charges on its surface;

(b) adding an aqueous solution comprising metal oxide salt to said dispersion of said particulate matter, under conditions wherein said metal oxide salt precipitates onto the surface of the particulate matter, and acidifying to thereby form a solid, water-insoluble particulate matter that has a metal oxide layer coated thereon;

(c) contacting, in a medium consisting of an aqueous medium, the particulate matter coated with a metal oxide layer of the preceding step with a surface adhering additive being one or both of (i) a second cationic additive being a cationic polymer and (ii) a non-ionic additive, to obtain a dispersion of said coated particulate matter having an adhering additive on the surface thereof in said aqueous medium;

(d) bringing the dispersion obtained in step (c) into contact with an aqueous solution of a sodium silicate, under conditions wherein said metal oxide salt precipitates onto the surface of said coated particulate matter, and acidifying to thereby form a solid, water-insoluble particulate matter that has a further metal oxide layer coated thereon;

(e) repeating steps (c) and (d) between 3-50 times at a temperature of between 28° C. to 40° C.; and optionally, after completion of step (e), aging the dispersion to obtain encapsulated benzoyl peroxide.

In other embodiments, the tretinoin is in a solid form, in an oil phase at a concentration of above 14% w/w in said oil phase (or in said core). In another embodiments, the concentration of the tretinoin in said oil phase (or in said core) is between 15% to 25% by weight. In other embodiments, the concentration of the tretinoin in said oil phase (or in said core) is between 17% to 25% by weight. In other embodiments, the concentration of the tretinoin in said oil phase (or in said core) is between 18% to 25% by weight. In other embodiments, the concentration of the tretinoin in said oil phase (or in said core) is between 19% to 25% by weight. In other embodiments, the concentration of the tretinoin in said oil phase (or in said core) is between 20% to 25% by weight.

In other embodiments, the dissolution rate of tretinoin within the pharmaceutical composition comprising E-BPO microcapsules and E-ATRA microcapsules of this invention, is between 5% to 35% weight/h as measured in a medium of 30%:70% V/V mixture of water:isopropyl alcohol at 32° C. and the BPO dissolution rate is between 10% to 60% weight/h as measured in a medium of 55%:45% mixture of water:acetonitrile at ambient temperature.

In other embodiments, the microencapsulation efficiency of BPO within the pharmaceutical composition comprising E-BPO microcapsules and E-ATRA microcapsules of this invention is at least 75%, preferably at least 85%, more preferably at least 90%; and the microencapsulation efficiency of tretinoin within the composition is of at least 90%.

Surprisingly it was found that even with high entrapment efficiency of benzoyl peroxide being at least 75%, preferably at least 85%, more preferably at least 90%, the ATRA was not stable if not encapsulated with entrapment efficiency higher than 90%. Table 4 in Example 12 below demonstrates that with 86.2% entrapment efficiency of ATRA (in the presence of encapsulated BPO), there was 1.64% of 5,6 epoxy retinoic acid (=RRT 0.44) and 2.96% of total related compounds (including inter alia 5,6 epoxy retinoic acid) after 3 weeks at 40° C. compared to 98% entrapment efficiency demonstrating stability of the ATRA with 1.13% of 5,6 epoxy retinoic acid (=RRT 0.44) and 2.24% of total related compounds after 3 weeks at 40° C.

In some embodiments, after two weeks storage at 40° C. and 75% relative humidity of the composition comprising E-ARTA and E-BPO of this invention, a concentration of all-trans 5,6-epoxy retinoic acid is less than 1% by weight of the initial tretinoin amount prior to storage. In other embodiments, a concentration of all-trans 5,6-epoxy retinoic acid is less than 0.7%. In some embodiments the degradation of the tretinoin from the composition of this invention is less than 2.5% after two weeks storage at 40° C. and 75% relative humidity. In another embodiment, the degradation of said tretinoin is less than 2% after two weeks storage at 40° C. and 75% relative humidity.

In some embodiments, this invention provides a pharmaceutical composition comprising any of the microcapsules of this invention described herein and a pharmaceutically acceptable carrier or excipient.

In some embodiments, this invention provides a pharmaceutical composition comprising a suspension comprising any of the microcapsules of this invention described herein and a pharmaceutically acceptable carrier or excipient.

Methods of Use

In some embodiments, this invention provides a method for improving, preventing and/or treating a skin disease, disorder or condition in a subject in need thereof, said method comprising topically administering to said subject the pharmaceutical compositions of this invention.

In other embodiments, the skin disease, disorder or condition is selected from acne, psoriasis, seborrhea, contact dermatitis, rosacea, and any combination thereof. In other embodiments, the methods of this invention are directed to improving, preventing and/or treating acne. In other embodiments, the methods of this invention are directed to improving, preventing and/or treating rosacea.

In other embodiments, the compositions of this invention are used for improving, preventing and/or treating a skin condition, such as acne, psoriasis, seborrhea, contact dermatitis, rosacea, and any combination.

In other embodiments, the composition of this invention comprising E-BPO is used for improving, preventing and/or treating rosacea, which substantially reduces the duration of the treatment and which provides a greater reduction of the symptoms and adverse effects of rosacea. In other embodiment, composition comprises between 1% weight to about 10 weight % of BPO. In other embodiment, the composition comprises between 2.5% weight to about 5 weight % of BPO. In other embodiment, the composition comprises about 5 weight % of BPO. In some embodiments the BPO is the single pharmaceutical active agent in the composition.

In other embodiments, said composition of the invention demonstrates adverse events value of no more than about (less than about) 50% upon topical use in the treatment of rosacea. In some embodiments wherein said composition demonstrates adverse events values of no more than about (less than about) 40%, 30%, 20% upon topical use in the treatment of rosacea.

The term "adverse events values" refers to average percentage of subjects that experience any adverse events associated with the treatment of rosacea with a composition of the invention (usually on the skin of a subject treated with a composition of the invention). A non-limiting list of such adverse events includes: irritation, dryness, scaling, purities, burning and stinging.

In other embodiments, the composition of this invention comprising E-BPO is used for improving, preventing and/or treating rosacea, and demonstrated a high percentage of subjects having a 2-grade improvement in the IGA (Investigator General Assessment) and reached a clear or almost clear condition of the disease, relative to baseline, at week 12.

In some embodiments, this invention provides a method for treating rosacea in a subject in need thereof, said method comprising topically administering to said subject a pharmaceutical composition comprising benzoyl peroxide (BPO) microcapsules of this invention, wherein the microcapsules have microencapsulation efficiency of at least 75%, preferably at least 85%, more preferably at least 90%. In other embodiment, the BPO comprises between 1% weight to about 10 weight % of the composition. In other embodiment, the BPO comprises between 2.5% weight to about 5 weight % of the composition. In other embodiment, the BPO comprises is about 5 weight % of the composition. In some embodiments the BPO is the single pharmaceutical active agent in the composition.

In some embodiments, said rosacea is papulopustular rosacea (i.e. inflammatory rosacea, see Rapini, Ronald P. et al. (2007). Dermatology: 2-Volume Set. St. Louis: Mosby and James, William et al. (2005). Andrews' Diseases of the Skin: Clinical Dermatology. (10th ed.). Saunders p. 245).

In other embodiments, the composition comprising E-BPO microcapsules used in the methods of this invention have microencapsulation efficiency of at least 75%, preferably at least 85%, more preferably at least 90%. In other embodiments, the composition comprising E-ATRA used in the methods of this invention have microencapsulation efficiency of at least 90%. In other embodiment, the microencapsulation efficiency of the tretinoin is between 90% to 100%. In other embodiment, the microencapsulation efficiency of the tretinoin is between 90% to 99%. In other embodiment, the microencapsulation efficiency of the tretinoin is between 90% to 98%. In other embodiment, the microencapsulation efficiency of the tretinoin is between 95% to 100%. In other embodiment, the microencapsulation efficiency of the tretinoin is between 96% to 100%. In other embodiment, the microencapsulation efficiency of the tretinoin is between 97% to 100%. In other embodiment, the microencapsulation efficiency of the tretinoin is between 98% to 100%.

In yet another aspect, the present invention provides a method for treating a surface condition (e.g., a skin disease or disorder) in a subject in need thereof, comprising topically administering to the subject an effective amount of a composition as described herein. In certain embodiments, the surface is skin or mucosal membrane. In some embodiments, the surface condition is a skin disease, disorder or condition selected from acne, infection, inflammation, pruritus, psoriasis, seborrhea, contact dermatitis, rosacea, melasma, photoaging, photodamage, fine wrinkles, and a combination thereof, each represents another embodiment of this invention. In another embodiment, the method of this invention is directed for treating acne. In another embodiment, the method of this invention is directed for treating rosacea.

The term "treating" or "treatment" as used herein includes any treatment of a condition, disease or disorder associated with a patient's body surface such as the skin or mucosal membrane, and includes inhibiting the disease or disorder (i.e. arresting its development), relieving the disease or disorder (i.e. causing regression of the disease or disorder), or relieving the conditions caused by the disease (i.e. symptoms of the disease). The concentrations of the dermatological agents that can be used for treatment of a specific disease or disorder may be as described in The Merck index an encyclopedia of chemical drugs and biologicals, Rahway, N.J.; Merck & Co; 1989, incorporated herein by reference in its entirety.

Definitions

As used herein unless otherwise indicated the term "microcapsule" refers to a microparticle having a core shell structure, wherein said core comprises an active agent as defined herein (tretinoin or benzoyl peroxide), being coated by a shell forming the microcapsule entrapping the core. In some embodiments, the core includes a phase changing material (PCM), as described herein.

In the context of the present invention, the term "core" and/or "core material" used interchangeably herein, refers to the inside/internal part of the microcapsules comprising said active agent, and, in some embodiments also said at least one phase changing material. The core or core material is surrounded by said shell of said microcapsule. It should be noted that additional compounds may be present in said core including for example carriers, excipients, pharmaceutically acceptable polymers or salts etc., all in accordance with the intended use of produced microcapsules, which will be apparent to a skilled artisan preparing said microcapsules. In other embodiments of the invention said core may be solid at room temperature. In other embodiments, said core may be in a semi-solid phase at room temperature.

In some embodiments, the present invention a process for obtaining a thick and dense coating on said core/core material, using in some embodiments metal oxide nanoparticles in combination with a sol-gel precursor, wherein the addition of phase changing material incorporated into said core provides further stability parameters to the encapsulated active agents and to the pharmaceutical composition comprising them.

The size of the microcapsules as will be referred to herein refers to $D_{90}$ meaning that 90% of the particles have the stated dimension or less (measured by volume). In other embodiment, the size of the microcapsules is referred to $D_{60}$, $D_{70}$ or $D_{80}$. In other embodiment, the size of the microcapsules will be referred as the average diameter size. In other embodiment, the size of the microcapsules will be referred as the average diameter mean size. Thus, for examples, for spherical particles stated to have a diameter of less than about 50 µm ("microns"), this means that the particles have a $D_{90}$ of 50 microns. The $D_{90}$ (termed also d(0.9)) may be measured by laser diffraction. For particles having a shape other than spheres, the $D_{90}$ refers to the mean average of the diameter of a plurality of particles.

The composition according to the present invention, comprise a shell wherein the shell is inorganic polymeric shell. In some embodiments, the shell is a metal oxide or semi-metal oxide shell.

In some embodiments, the metal oxide or semi-metal oxide shell is formed by a sol-gel encapsulation/coating process.

In some embodiments, the metal oxide is selected from silica, titania, alumina, zirconia, ZnO, and mixtures thereof. In some other embodiments, the metal oxide is silica.

The width of the metal oxide layer may be determined for example by Scanning Electron Microscopy (SEM), cryo-SEM, or a Transmission Electron Microscope or Confocal Microscope such that in a circular cross-sectional area of the particle the smallest width is at least e.g. 0.1 µm (the width is determined as the smallest distance from the surface of the particle (i.e. metal oxide surface) to the core-metal oxide interface).

In the present invention the terms "layer", "coating" or "shell" and similar terms, refer to a layer of metal oxide or semi-metal oxide formed around a particle or particulate matter. The layer or coating may not always be complete or uniform and may not necessarily lead to complete coverage of the particulate matter or particle surface. It is appreciated that upon repetition of the coating steps as the coating process proceeds a more uniform coating and more complete coverage of the particulate matter is obtained.

According to certain embodiments of the present invention, the surface of the metal oxide layer of the coated particulate matter may be chemically modified by organic groups, in some embodiments, hydrophobic groups are attached to its surface. The hydrophobic groups may be for example alkyl groups (such alkyl groups may be further substituted with one or more fluoro atoms), aryl groups (such as benzyl or phenyl), and combinations thereof. The groups may be as described below with respect to the process.

According to an embodiment of the present invention the weight ratio of the metal oxide to the solid particulate matter is in the range of 1:99 to 50:50. The weight ratio of the metal oxide layer to the solid particulate matter may be also in the range of 3:97 to 50:50, 5:95 to 50:50, 10:90 to 50:50, 5:95 to 30:70, 10:90 to 30:70. Further, according to an embodiment of the present invention the rate ratio of the metal oxide to the solid particulate matter is in the range of 10:90 to 20:80.

It should be noted that the dissolution rate (release rate) defined herein relates to the measurement (either in vitro or in vivo) of the rate at which the active agents (tretinoin or benzoyl peroxide) is released from the topical medicament of the invention, to the extracting media or skin.

In some embodiments wherein said composition of the invention further comprises tretinoin and benzoyl peroxide, the concentration of all-trans 5,6-epoxy retinoic acid is lower than 1% after two weeks storage at 40° C.

When referring to all-trans 5,6-epoxy retinoic acid it should be understood to relate to the degradation product of tretinoin in the presence of BPO as shown in the HPLC chromatography of the composition of the invention after two weeks of storage at 40° C. all-trans 5,6-epoxy retinoic acid is represented by the following structure:

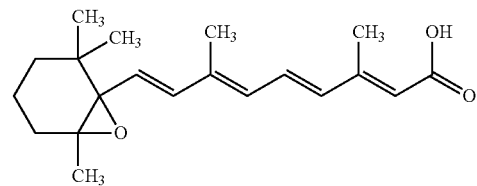 [SMILES: CC(/C=C/C12OC1(C)CCCC2(C)C)=C\C=C\C(C)=C\C(=O)O]

In some embodiments the degradation of said tretinoin (in the presence of BPO) is less than 2.5% after two weeks storage at 40° C. In other embodiments, the degradation of said tretinoin is less than 2%.

In some embodiments, wherein the composition of the invention further comprises BPO, the degradation of said tretinoin is not more than 5% after 18 or 24 months storage at 2° C.-8° C. In other embodiments, the degradation of said tretinoin is not more than 5% after 3 months storage at 25° C. and 60% RH.

In one embodiment, the term "about", refers to a deviance of between 0.0001-5% from the indicated number or range of numbers. In one embodiment, the term "about", refers to a deviance of between 1-10% from the indicated number or range of numbers.

The terms "tretinoin", "ATRA" and "all trans retinoic acid" are used herein interchangeable.

The terms "entrapment efficiency" (EE), "microencapsulation efficiency" and "encapsulation efficiency" are used interchangeable herein and refer to the percentage of the API (ATRA or benzoyl peroxide) being entrapped vs the initial API quantity. The EE is calculated as described in Example 11 for ATRA, and the same calculation is being used for calculating the EE of benzoyl peroxide.

In some embodiments, the composition of this invention is a pharmaceutical composition. The term "pharmaceutical composition" means a composition suitable for pharmaceutical use as defined herein. In another embodiment, the pharmaceutical composition comprises a suitable carrier or diluent. The pharmaceutical composition of this invention includes a therapeutically effective amount of the active ingredient, i.e. the amount which provides a therapeutic effect for a given condition and administration regimen.

The active component can be formulated into the composition as its hydrate, solvate, or as its pharmaceutically acceptable salt. Suitable pharmaceutically acceptable salts of the active component(s) (i.e. tretinoin) of this invention include inorganic salts such as: ammonium, alkali metals to include lithium, sodium, potassium, cesium; alkaline earth metals to include calcium, magnesium, aluminium; zinc, barium; or quaternary ammoniums; or organic salts such as arginine, organic amines to include aliphatic organic amines, aromatic amines, t-butylamines, (N-benzylphenethylamine), dicyclohexylamines, dimethylamines, diethanolamines, ethanolamines, ethylenediamines, imidazoles, lysines, methylamines, N-methyl-D-glucamines, N,N'-dibenzylethylenediamines, pyridines, picolinates, piperazines, tris(hydroxymethyl)methylamines, triethylamines, triethanolamines, trimethylamines, or ureas.

In some embodiment, a composition of the invention is a topical medicament. The term "topical medicament" as used herein should be understood to encompass any pharmaceutical formulation that enables the administration of the active agents to a skin tissue, mucous membranes and/or the integuments of a patient administered with said medicament. The composition or topical medicament of the present invention comprises a carrier. According to an embodiment of the present invention the carrier is in the form of an ointment, a cream, a lotion, an oil, a solution (in some embodiments an aqueous solution), an emulsion, a gel, a paste, a milk, an aerosol, a powder, or a foam, each represents another embodiment of this invention. In some embodiments, the carrier is an aqueous-based carrier (such as a gel, oil-in water emulsion or oil-in water cream, aqueous solution, foam, lotion, spray).

In some embodiments, the compositions of this invention comprise a carrier in a form of an ointment, a cream, a lotion, an oil, a solution, an emulsion, a gel, a paste, a milk, an aerosol, a powder or a foam.

Thus, the final form of the composition may be any of the above forms, mentioned with respect to the carrier, where the microcapsules are dispersed in the carrier. The final form of the composition may also be in the form of a wash or cleanser.

The following examples are presented in order to more fully illustrate the preferred embodiments of the invention. They should in no way, however, be construed as limiting the broad scope of the invention.

EXAMPLES

Example 1

Encapsulation of Benzoyl Peroxide (BPO)-15% E-BPO Suspension

Three solutions were prepared:
1. An acid solution of 7% w/w citric acid, 10% w/w lactic acid and 32% w/w hydrochloric acid;
2. A Polyquaternium-7 (Lubrizol) aqueous solution (3 wt. %); and
3. Sodium silicate solution—about 160 gr of silicon dioxide and 700 gr of sodium hydroxide were dissolved in 7 kg of water.

(a) BPO dispersing (Stage 1 in FIG. 1). A BPO dispersion was prepared by mixing 9 kg of hydrous BPO 75% (USP grade, Akzo Nobel) with 378 g CTAC (cetyltrimethylammonium chloride, Lonza) and 15.56 kg water under high shear.

(b) E-BPO encapsulation cycles (Stages 2 and 3 in FIG. 1).

Sodium silicate (solution 3-mentioned) was added to the BPO dispersion (of step a) under high shear, followed by adding the acid solution (solution 1-mentioned) to adjust the pH to be lower than 6.8, and followed by (c) adding the Polyquaternium-7 aqueous solution (solution 2-mentioned) to the mixture. (d) The cycle (steps b & c) was repeated 3-50 times at a temperature of between 28° C. to 40° C. After the final cycle, the pH of the mixture was adjusted to about 5.0 using the acid solution (solution 1—mentioned), and water was added to complete the total weight of the mixture to 45 kg.

Example 2

Encapsulation of Tretinoin (all Trans Retionic Acid-ATRA)-3.4% E-ATRA Suspension Preparation of sodium silicate solution: 13 gr of silicon dioxide and 4.5 gr of sodium hydroxide were dissolved in 26 g of water.

a) Aqueous phase (phase A): 7.5 g CTAC (surfactant) and 5,500 g of water was stirred and heated to 65° C. for about an hour to obtain a clear solution.

b) Oil Phase (phase B):120 g Squalane, 10.5 g BHT (butylated hydroxytoluene, antioxidant), 85.5 g TEOS (tetraethyl orthosilicate, a silica monomer) and 54 g tretinoin were added, and milled with a WAB Dynomill for 25 min, while cooling. Then the oil phase was heated to 60° C. and 18 g beeswax (Kahl) were added and mixed until dissolved (FIG. 2, stage 1).

Figure 2:
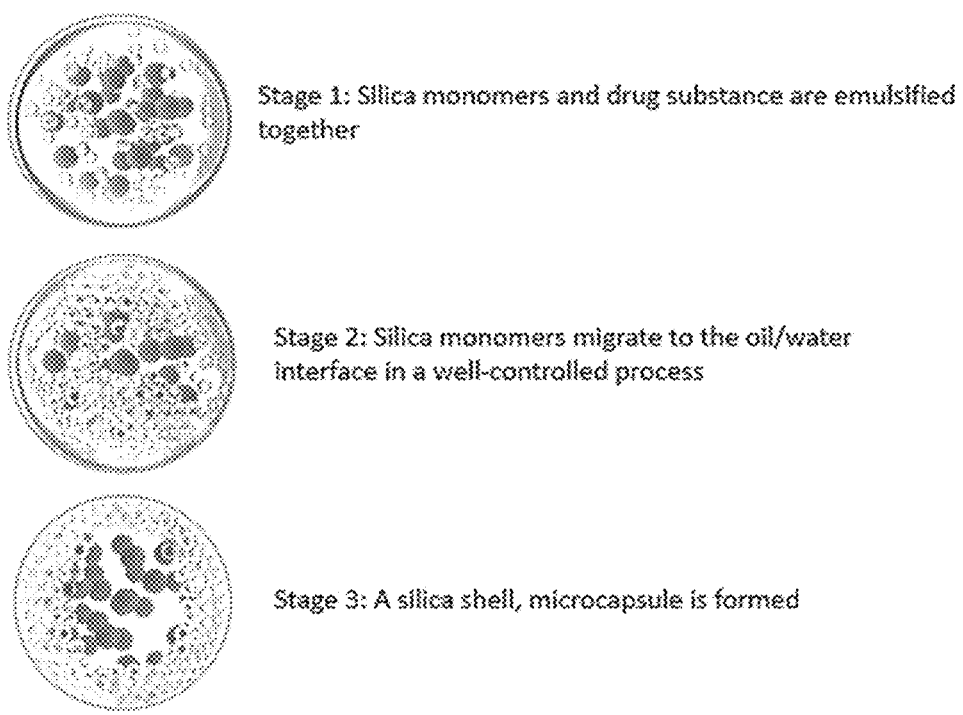
FIG. 2 Illustration of the Tretinoin microencapsulation process.

Phase A was added to phase B, and the suspension was homogenized with IKA UTS homogenizer (FIG. 2, stage 2). During homogenization about 41 g sodium silicate solution was added followed by addition of about 40 g HCl 10%. The pH was adjusted to pH of between 3.9 to 4.2. Homogenization was stopped and mixing with a mechanical motor stirrer was applied for at least 40 hours (FIG. 2, stage 3).

Example 3

Preparation of Formulation of Encapsulated ATRA (E-ATRA) (0.1%) and Encapsulated BPO (E-BPO) (3%)

Oil Phase: 720.0 of grams Cyclomethicone 5-N, 540.0 of grams Cetyl Alcohol, 540.0 grams of Glyceryl Monosterate and 72.0 grams of Carbopol 980 NF were mixed at 70° C.

Water phase: 18.0 grams of Ethylendiaminetetraacetate Disodium salt, 360.0 grams Polyoxyl 100 Stearate, 45.0 grams of Imidurea and 720.0 grams of glycerin (99.5%) were dissolved in 10 kg of water. The solution was heated to 70° C.

The oil phase was added to the water phase under high shear at 70° C., and the resulting emulsion was homogenized at 3300 rpm for 10 minutes. 72 grams of sodium hydroxide (20%) were then added followed by 36.0 grams of Citric Acid and 3576 grams of encapsulated BPO 15% water suspension made as described in Example 1. The emulsion was cooled to 55° C. and the pH of the emulsion was adjusted to about 4 using HCl 10% solution. After 530 grams of encapsulated ATRA 3.4% water suspension, made as described in Example 2, were added, the emulsion was stirred at 1400 rpm for 10 minutes. Water was added until the total weight of the emulsion reached 18 kilograms. The emulsion continued mixing for 90 minutes during cool down to about 30° C.

Example 4

Cryo-SEM Characterization of the E-ATRA and E-BPO
Sample Preparation for Cryo-SEM and Imaging Methods:

For cryogenic scanning electron microscopy (cryo-SEM) imaging we used a Zeiss Ultra Plus high-resolution SEM, equipped with a Schottky field-emission gun and with a BalTec VCT100 cold-stage maintained below −145° C. Specimens were imaged at low acceleration voltages of 1-1.2 kV, and working distances of 3-5 mm. At those acceleration voltages, the specimens remained electrically neutral without coating with a conductive layer. We used both the Everhart Thornley ("SE2") and the in-the-column ("InLens") secondary electron imaging detectors. The energy-selective backscattered ("ESB") detector was used for elemental contrast between silica particles and organic/aqueous phases. Low-dose imaging was applied to all specimens to minimize electron-beam radiation-damage. For the confirmation of the sample composition we used a Quantax energy dispersive x-ray spectrometer (EDS, Bruker) at an acceleration voltage of 5 kV. This higher acceleration voltage was need for sufficient x-ray emission from the specimens.

Cryo-specimens were prepared by the drop plunging method, as described by Koifman et al., which is incorporated herein by reference (Koifman, N.; Biran, I.; Aharon, A.; Brenner, B.; Talmon, Y. A Direct-Imaging Cryo-EM Study of Shedding Extracellular Vesicles from Leukemic Monocytes. *J. Struct. Biol.* 2017, 198 (3), 177-185) A 3 μL drop of solution is set on top of a special planchette, maintaining its hemispherical droplet shape, and is manually plunged into freezing liquid ethane, after which it is set on top of a dedicated "sample table" set in a liquid nitrogen reservoir and transferred by a high vacuum cryo-transfer shuttle (VCT100; Bal-Tec) to a freeze-fracture system (BAF060; Leica), at −170° C. In the BAF060, the frozen droplets are fractured by a rapid stroke from a cooled knife, exposing their inner part. They are then transferred into the pre-cooled HR-SEM as described above. Ideally, imaging is performed as close as possible to the drop outer surface, where the cooling-rates during thermal fixation should be the highest.

Results

Figure 3A:
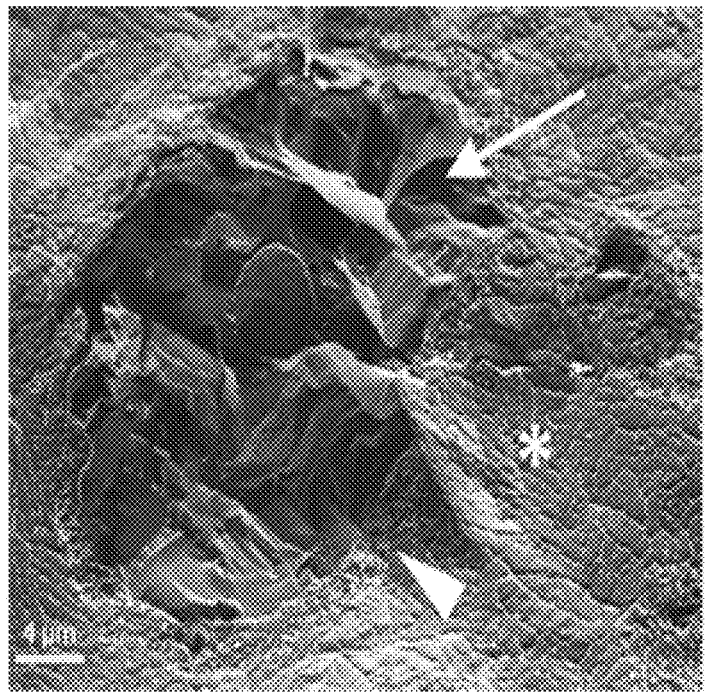
FIGS. 3A-3B show Cryo-SEM of a fractured E-ATRA capsule.
Figure 3B:
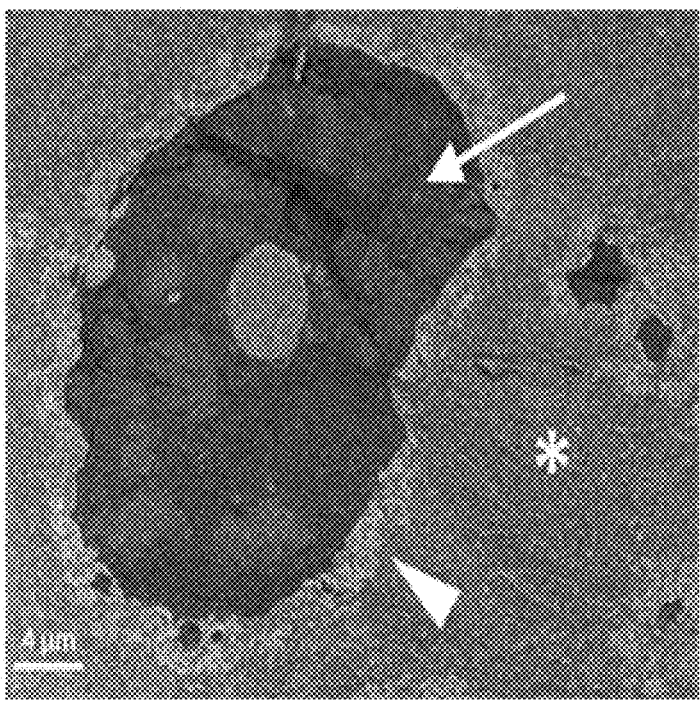

FIGS. 3A and 3B show two cryo-SEM micrographs of the same fractured E-ATRA capsule. To maximize the information obtained from the specimen, we used two electron detectors for each of the specimens we studied: An Everhart Thornley (ET; "SE2" in the Zeiss lingo) detector, located in the specimen chamber, close to the specimen, and an in-the-column, energy selective backscattered electron detector ("EsB" in the Zeiss lingo). The ET detector, which collects also some backscattered electrons, gives topographical information, while the EsB detector gives compositional contrast, because heavier atoms give more backscattered electrons than lighter ones, thus domains rich in the former appear lighter than those richer in the latter. In EsB micrographs the topographical information is lost. So, FIG. 3A shows the topography of the fracture plane, which is quite different for the aqueous matrix (asterisk) and the capsule (arrow). Close examination of the capsule reveals also the silica shell around it (arrowhead), with a thickness of approximately ~2 μm. The very rugged appearance of the capsule interior is a result of the probable crystallization of the oil phase during cryo-specimen preparation and the inherent crystalline properties of the ATRA crystals. FIG. 3B is an EsB micrograph, showing good contrast between domains rich in different atomic number elements. The darkest domains are oil-rich (arrow) and the lightest area are the silica shell (arrowhead). In between in intensity is the aqueous matrix (asterisk). In the capsule core we see lighter domains of different levels of intensity. Lighter domains seen on the organic phase of the capsule could be silica or ice debris. Two very small capsules are seen on the right-hand side of the field of view.

The specimen shown in FIGS. 3A-3B, like all others shown here, was imaged at low electron-beam acceleration voltage, between 1 and 1.4 kV. The specimens, although non-conductive, were not coated, as at the beam acceleration voltage we used, the number of electrons leaving the specimen is equal to the number of landing electrons, and thus, even non-conductive specimens do not charge up. In choosing the voltage was also opted for best micrograph contrast.

Figure 4A:
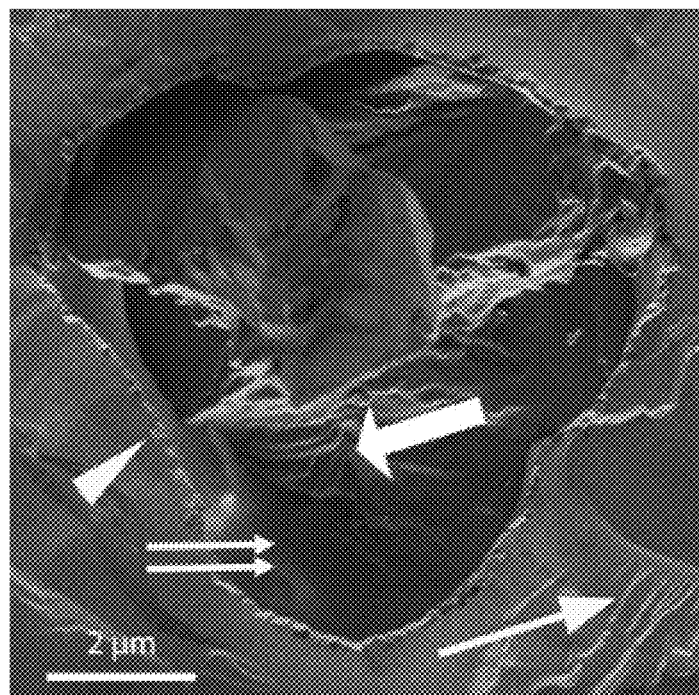
FIGS. 4A-4B show Cryo-SEM of a fractured E-BPO capsule.
Figure 4B:
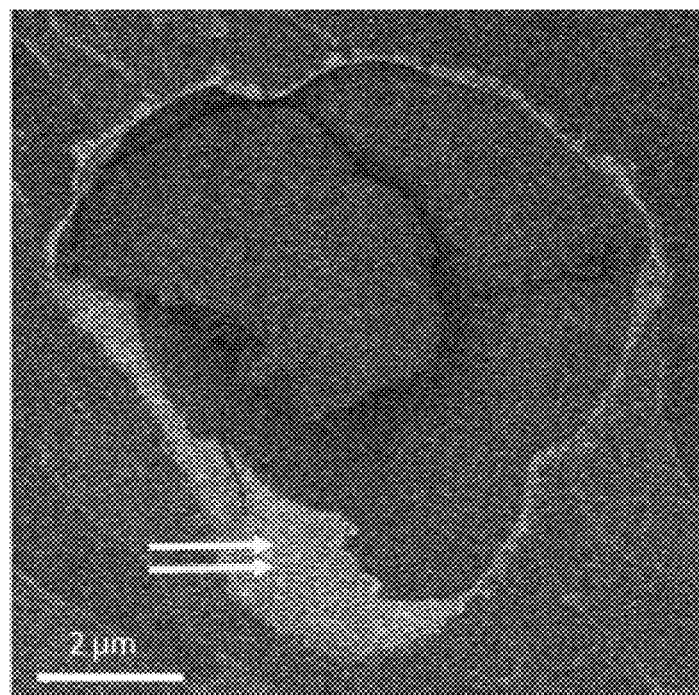

A fractured cryo-SEM specimen of an E-BPO capsule in the aqueous medium is shown in FIGS. 4A-4B. The secondary electron detector (ET) micrograph (FIG. 4A) shows the topography of the capsule. Note the granularity of the silica shell (arrowhead). The E-BPO capsule shell, shown in FIG. 5, has a thickness of approximately ~100 nm. Faceting in the E-BPO phase (thick arrow) and in the aqueous phase (thin arrow) indicates crystallinity. The water phase was crystallized during specimen preparation. It should be noted that because the organic phase and the aqueous phase are immiscible, we do not expect that crystallization leads to structural changes on the scale we are interested in. FIG. 4B shows the same field of view as imaged by backscattered electrons, using the EsB detector. As explained for FIGS. 3A-3B, the silica shell appears the brightest in the micrograph. The left-hand side of the shell (double-arrow) seems thicker than its right-hand side, while the same in FIGS. 4A-4B looks quite uniform in thickness. The reason is that fracturing of the capsule formed an almost vertical exposed section of the shell on the left hand side, which is only barely visible by the ET detector in FIG. 4A as a lighter grey area (double arrow), but is quite clearly visible by the EsB detector in FIG. 4B (double-arrow in the same area).

Figure 5A:
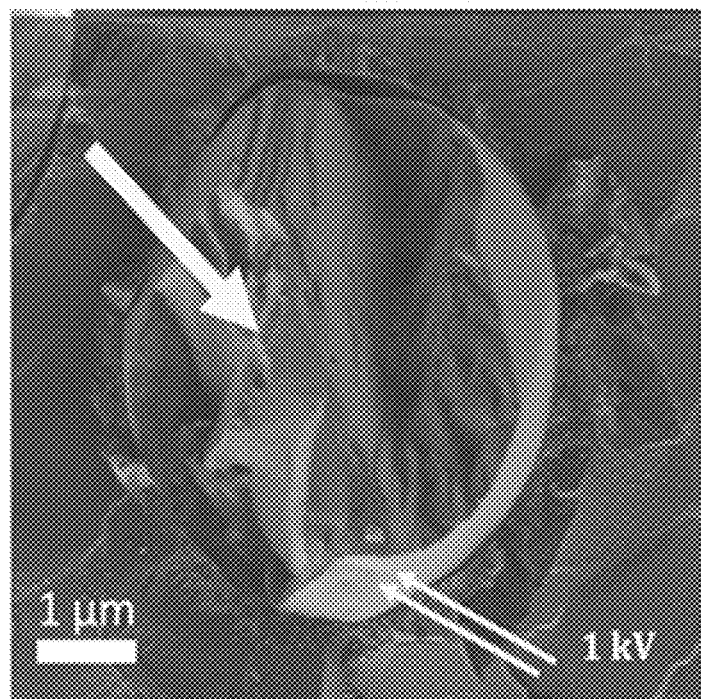
FIGS. 5A-5D show Cryo-SEM micrographs of an E-BPO capsule combined with x-ray microanalysis.
Figure 5B:
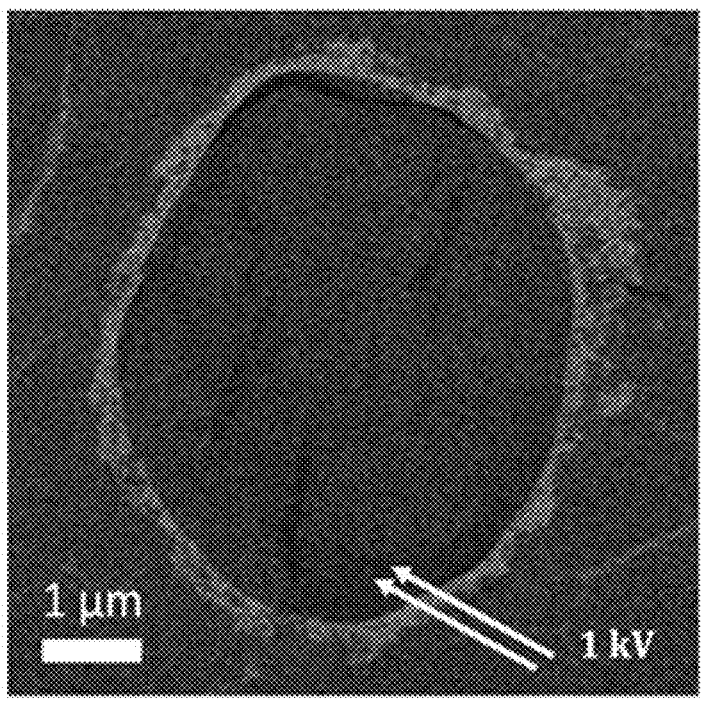
Figure 5C:
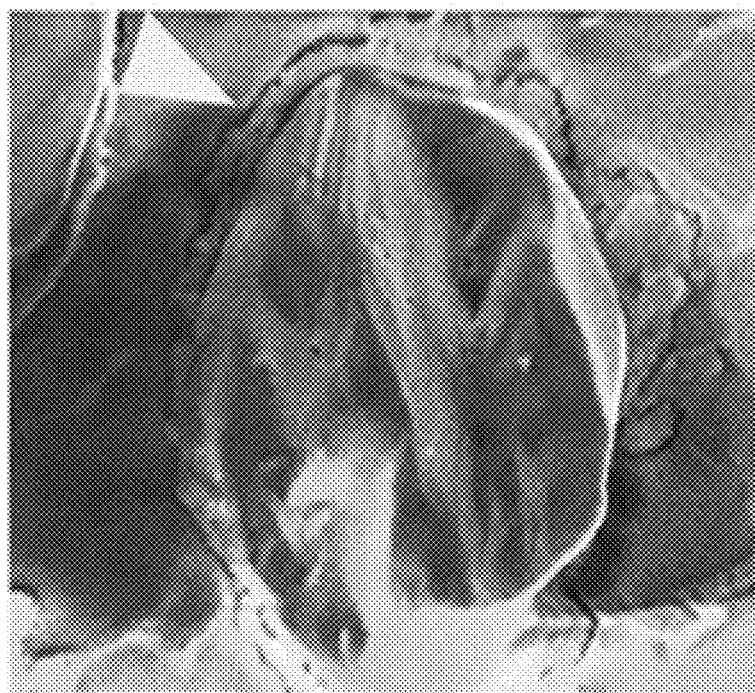
Figure 5D:
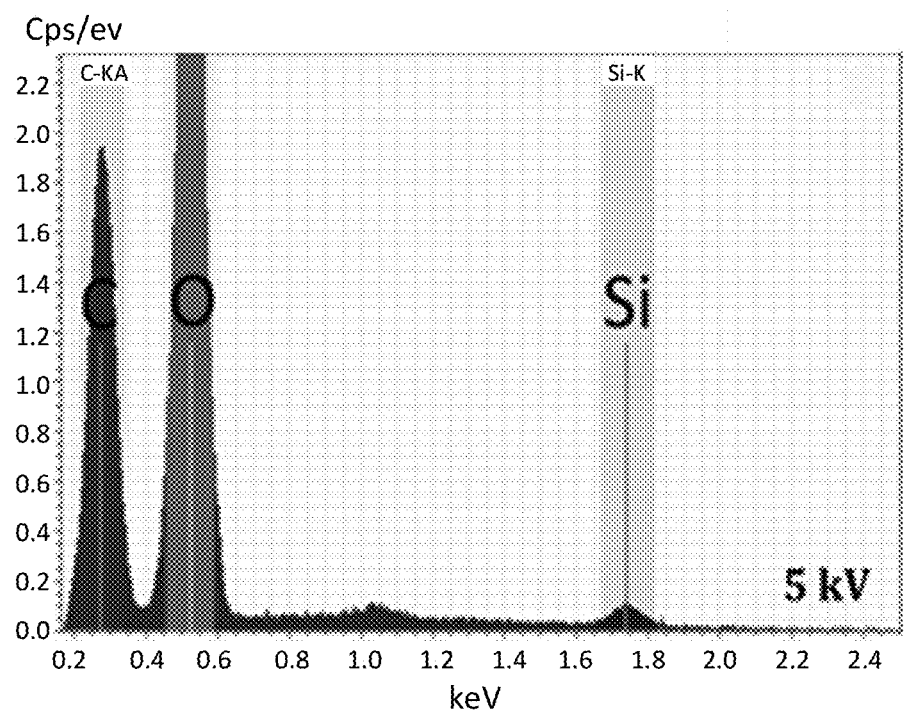

In FIGS. 5A-5D we add to the imaging (FIGS. 5A, 5B) compositional information (FIGS. 5C, 5D). Here we examine a cryo-SEM specimen of an E-BPO capsule suspended in the aqueous phase. The topography of the fractured capsule with its granular silica-rich shell is clearly visible, by the ET detector, including the fractured BPO crystal in its core (arrow; FIG. 5A). The micrograph recorded with the EsB detector (FIG. 5B) allows accurate measurement of the shell thickness due to the good atomic number contrast differences between the capsule core and its shell.

In FIG. 5A we observe that the right-hand side of the shell has been exposed in the direction approximately perpendicular to the fracture surface. That part of the shell appears light in the micrograph (double-arrows), because of electrons backscattered in the direction of the ET detector. Such electrons are most important in giving the three-dimensional-like appearance of ET SEM micrographs. Other backscattered electrons are collected by the EsB detector, giving in FIG. 5B the appearance of widening of the shell (double-arrow).

In FIG. 5C we give the energy spectrum of the element-specific x-rays emitted from the specimen when scanned by electron beam, collected by the energy dispersive spectroscopy (EDS) system, showing the peaks for carbon, oxygen and silicon. In FIG. 5D we see the elemental map of the specimen, superposed on an SE2 micrograph, with domains of different compositions, marked by the same colors used to label the peaks in the energy spectrum of FIG. 5C. As expected, the capsule core is rich in carbon (BPO), the shell in silicon dioxide (silica), and the aqueous phase in oxygen (water).

The combination of the two electron and the x-rays signals, suggest that in this case the shell is indeed not uniform. That is accentuated by electron beam radiation damage (Talmon, Y.; Adrian, M.; Dubochet, J. Electron Beam Radiation Damage to Organic Inclusions in Vitreous, Cubic, and Hexagonal Ice. *Sect. Title Chem. Synth. High Polym.* 1986, 141 (3), 375-384) that induced cracking around the silica shell around the capsule (arrowhead in FIG. 5D).

To obtain more information from the cryo-SEM specimen, one may etch it, either by exposing it to the electron beam for tens of seconds, or by briefly warming it in the SEM to an elevated temperature of –100° C., and then cool it down to the normal working temperature below –145° C. In the first case the electron beam splits the water molecules, forming free radicals. That could lead to a free-radical chain-reaction that causes loss of water and organic matter, if present in close proximity to the water. In the second case water is lost through sublimation. Temperatures above –120° C. may also cause ice crystal growth (Falls, A. H.; Wellinghoff, S. T.; Talmon, Y.; Thomas, E. L. A Transmission Electron Microscopy Study of Hexagonal Ice. *J. Mater. Sci.* 1983, 18 (9), 2752-2764), which may alter the nanostructure of the liquid phase.

Figure 6A:
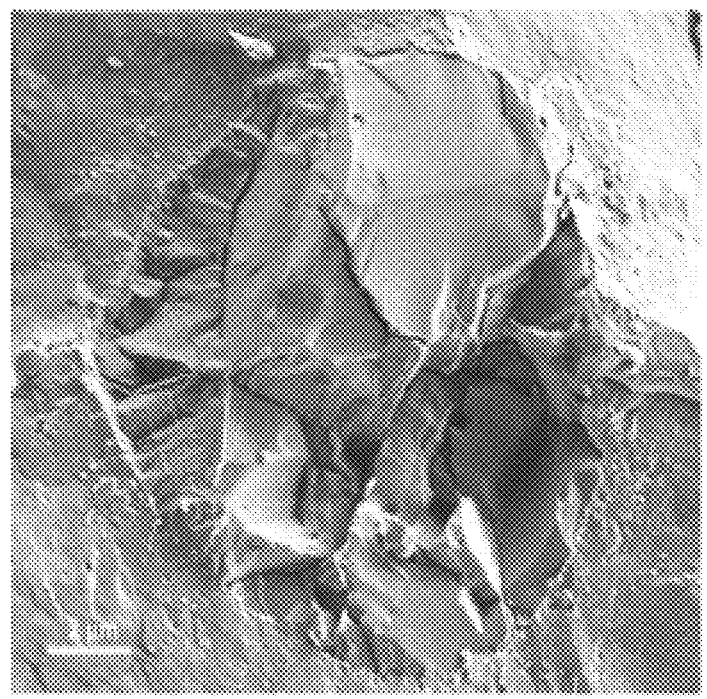
FIGS. 6A-6D show Cryo-SEM (ET detector—FIG. 6A, 6C; EsB detector—FIG. 6B, 6D) of an E-ATRA capsule without etching (6A and 6B) namely, gentle sublimation of the specimen under vacuum conditions, and a similar capsule after 1 minute etching at −100° C. (6C and 6D). Etching results in better exposure of both the capsule shell, as well as the different phases of the capsule core (amorphous vs. crystalline). The etching (6D) also indicates the presence of silica in the surrounding aqueous phase (arrow).
Figure 6B:
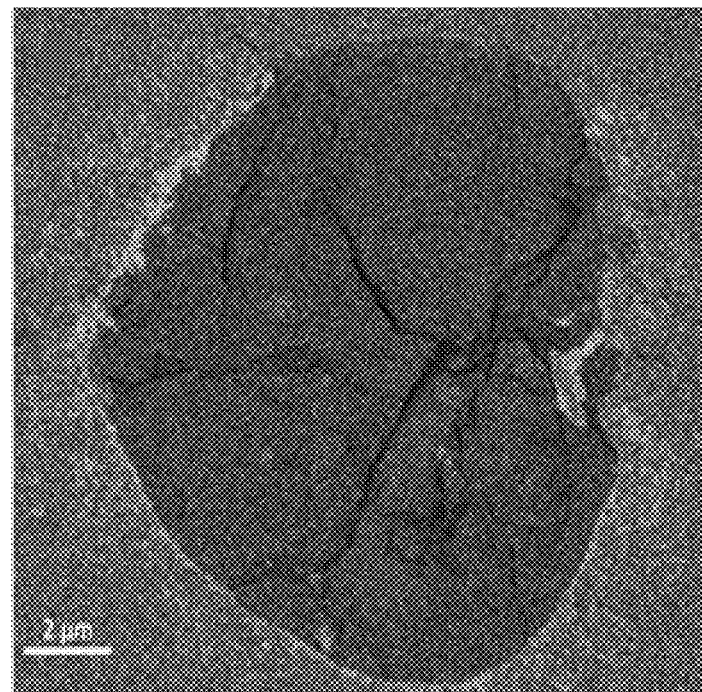
Figure 6C:
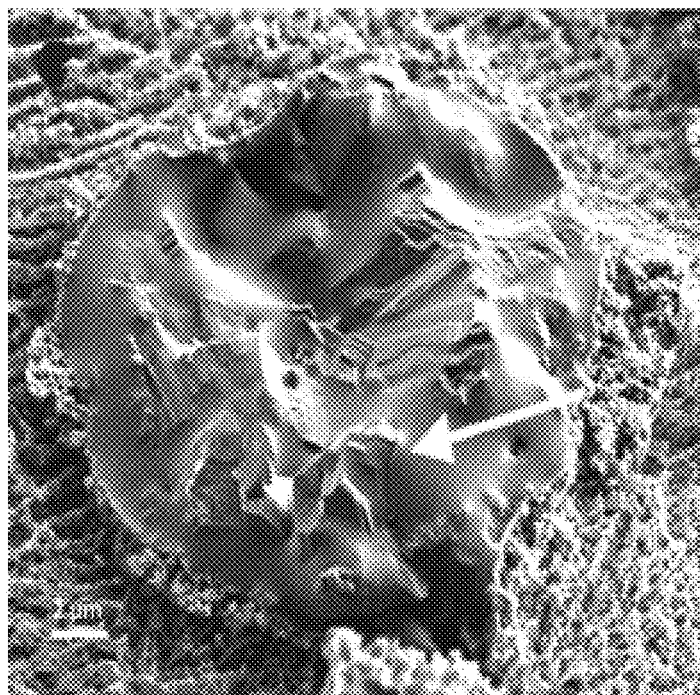
Figure 6D:
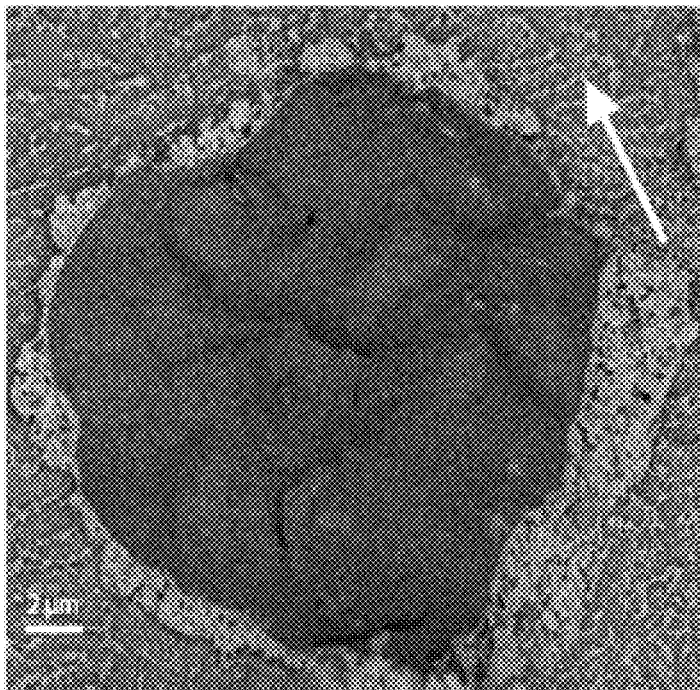
Figure 7A:
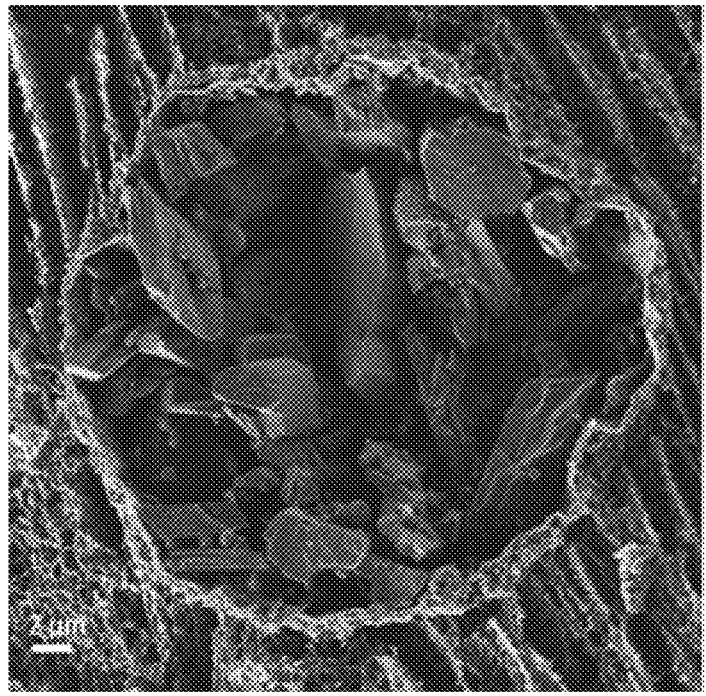
FIGS. 7A-7B show Cryo-SEM micrographs (FIG. 7A—SE2 detector.
Figure 7B:
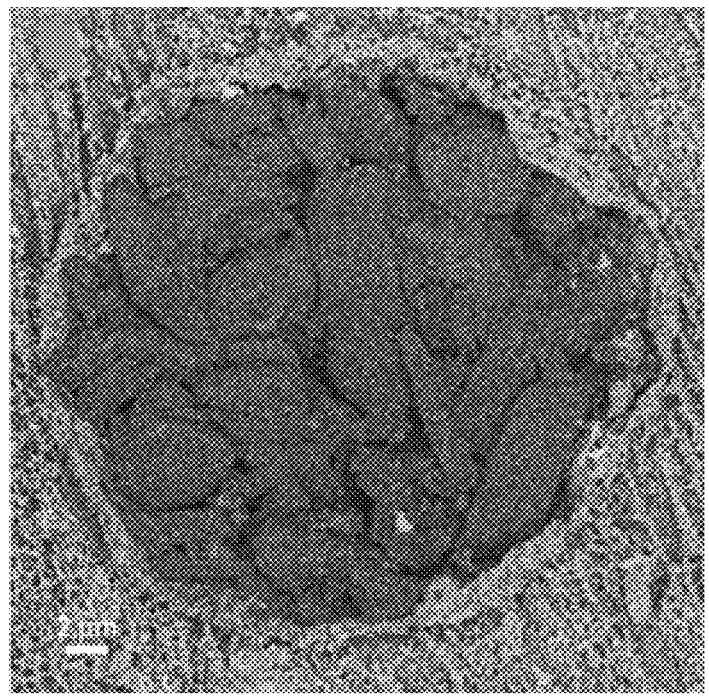

In FIGS. 6A-6D we present cryo-SEM images of E-ATRA capsules using the ET detector (FIGS. 6A and 6C) and the EsB detector (FIGS. 6B and 6D). FIGS. 6A and 6B show a capsule before etching, similarly to the micrographs in FIGS. 3A-3B. FIGS. 6C and 6D show a similar capsule after etching by sublimation of water in the SEM, by warming specimen holder to –100° C., and then cooling it back, after one minute at the higher temperature, to the working temperature of –145° C. Water sublimation also brought out better the details of the silica shell. The apparent larger shell thickness size is caused by exposing more silica by the receding ice level, and making more volume accessible to backscattered electron generation and escape from the specimen. The sublimation also exposed silica in the aqueous phase (arrow in FIG. 6D). Note that sublimation should be performed with care because if the water in the aqueous phase is completely sublimated, it is difficult to differentiate between free silica and the silica in the capsule shell, as shown in FIGS. 7A-7B.

Using state-of-the-art cryo-SEM, taking advantage of high-sensitivity detectors and the low electron acceleration voltage, bright beam afforded by the field-emission gun, we were able to give complete nanostructural and elemental analyses of both BPO and tretinoin microencapsulated in a silica shell prepared by the sol-gel process. The analysis shows that regardless of the encapsulation technique, a core shell structure is formed, satisfying the requirements of the specific drug formulation. In addition to showing the effectiveness of the encapsulation we demonstrated the power of a direct-imaging methodology that could be used for the structural analysis of a wide range of aqueous and non-aqueous suspensions of microparticles.

Example 5

SEM and Cryo-SEM Characterization of E-BPO

Figure 8A:
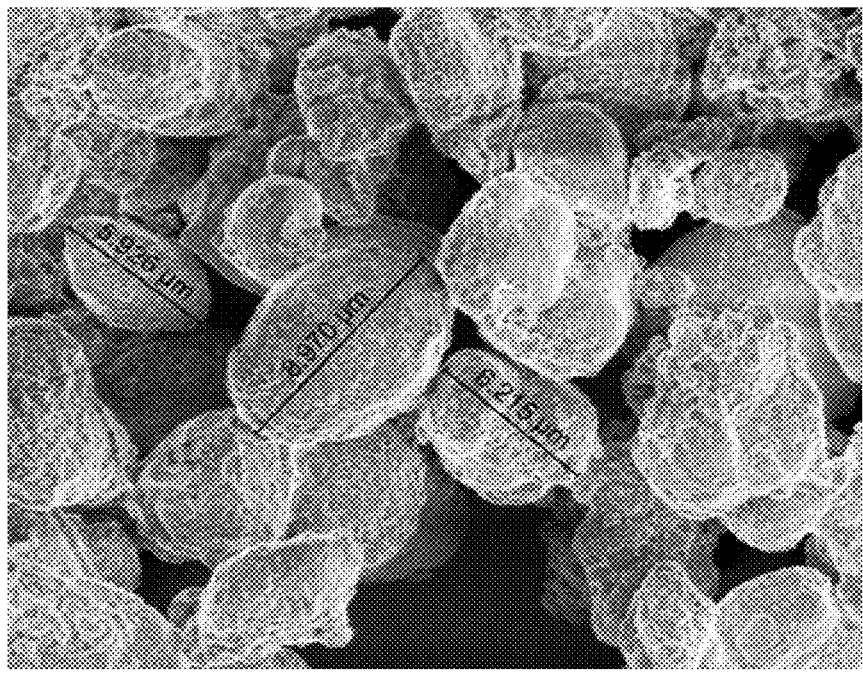
FIG. 8A-8C are SEM images of various E-BPO suspensions. The surface of the microcapsules is rough.
Figure 8B:
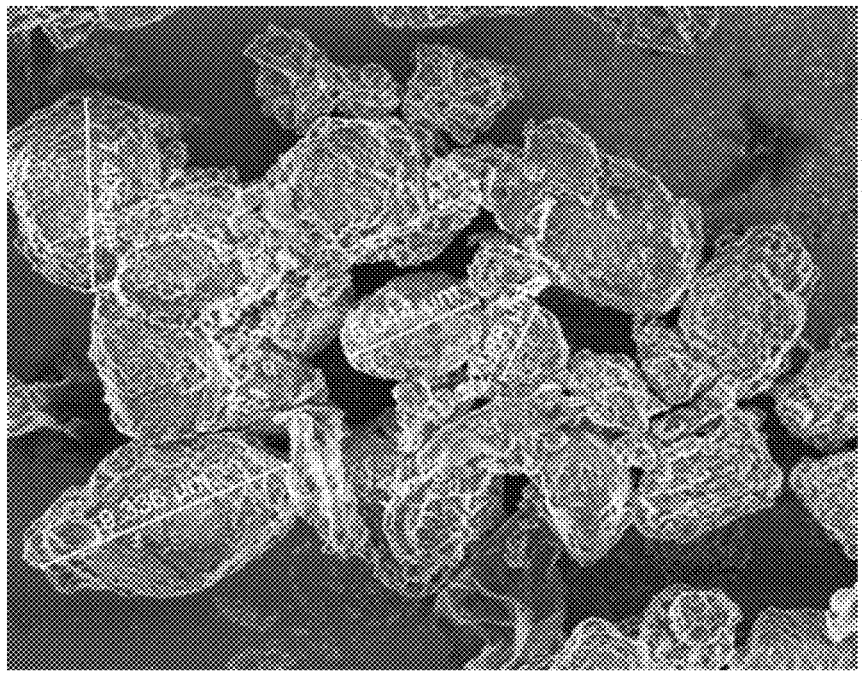
Figure 8C:
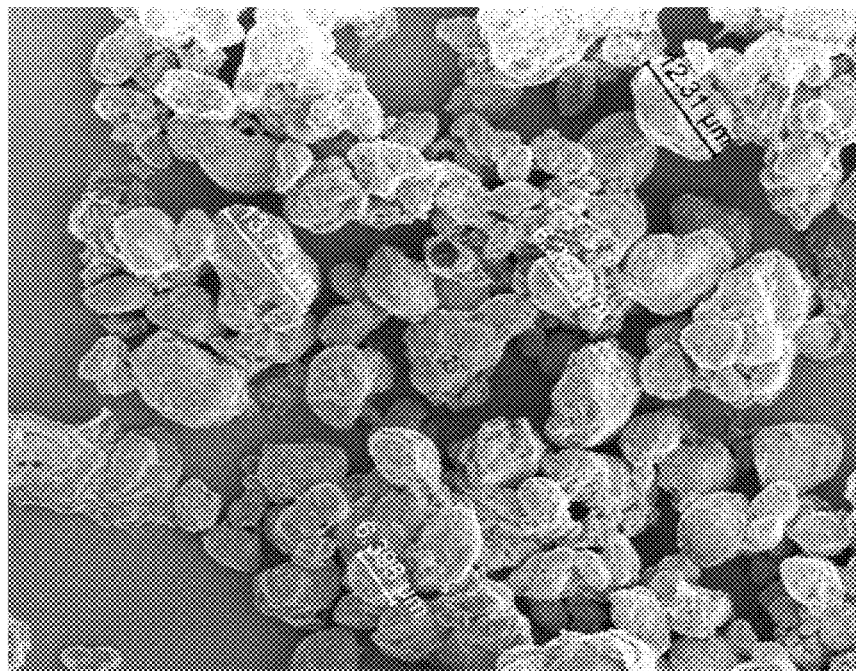

Various batches of E-BPO suspensions 15% (by weight) were characterized by cryo-SEM and SEM imaging.
Methods and Sample Preparation
Cryo-SEM
Samples for cryo-SEM were prepared as described in Example 4.
SEM
Sample preparation of E-BPO suspensions: The suspension was diluted with purified water until becoming visually clear. One drop of the sample was placed on a silicon wafer. The sample was dried under a hood for several hours.
SEM Images of E-BPO Microcapsules—Results and Discussion
Representative SEM images of E-BPO microcapsules from various batches are provided in FIG. 8A-8C. As seen in FIGS. 8A-8C, the microcapsules display microcapsules with a rough surface. The measured diameter of the microcapsules was below 25 µm, and most of the microcapsules were even smaller than 10 µm.
Cryo-SEM of E-BPO Microcapsules—Results and Discussion
Unlike the SEM, cryo-SEM allows us to view thermally-fixed specimens in a fully hydrated state, without adding a fixation agent and without drying, thus preserving very well the system original micro- and nanostructure. Fast-cooled cryo-SEM specimens can be fractured to reveal fine nanostructural details of the core-shell microcapsules interior. By imaging cross-sections of the microcapsules one can measure the thickness of the silica shell that surrounds the core that contains the active material crystals. The sample preparation for cryo-SEM and imaging details were performed as described in Example 4.

As explained in example 4, the EsB micrographs taken during the cryo-SEM imaging, permit good contrast between domains rich in different atomic number elements, allowing to differentiate between silicon and carbon which corresponds to the silica shell (lighter domains) and the organic core of the microcapsules (darker domains), respectively. This differentiation enabled the measurement of the silica shell thickness surrounding the organic core containing tretinoin crystals.

Figure 9A:
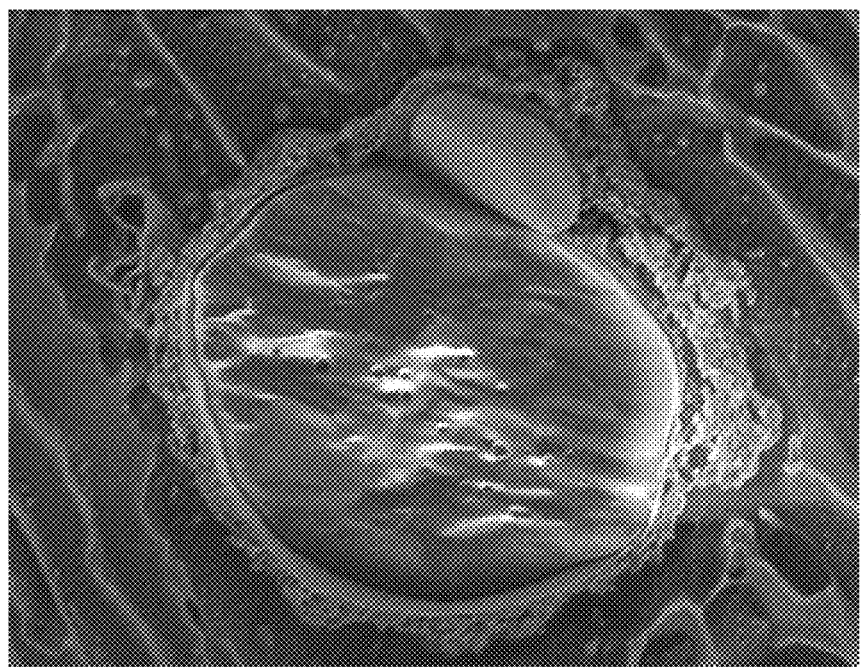
FIG. 9A-9B—cryo-SEM micrographs of an E-BPO microcapsule.
Figure 9B:
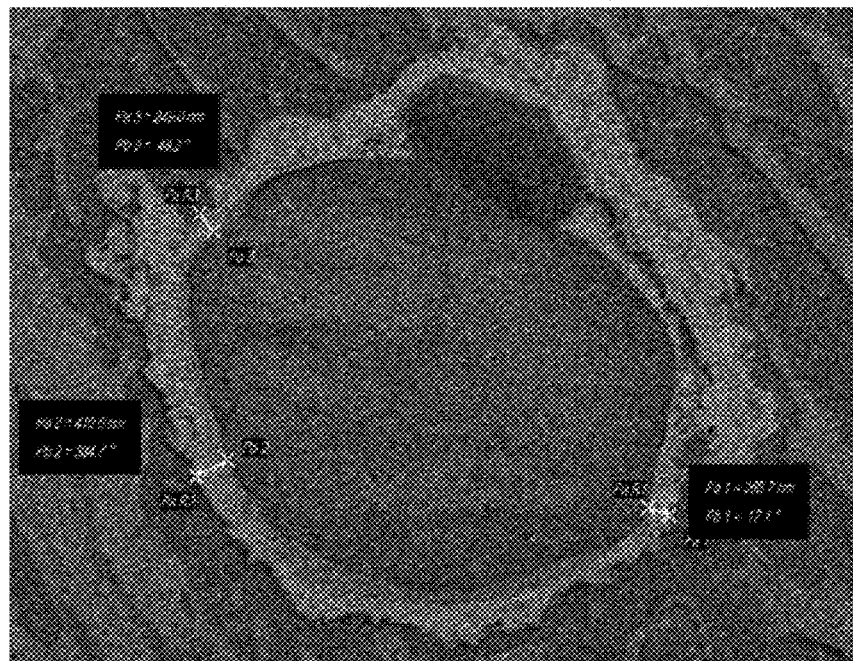
Figure 10A:
FIG. 10A-10B—cryo-SEM micrographs of two E-BPO microcapsules.
Figure 10B:
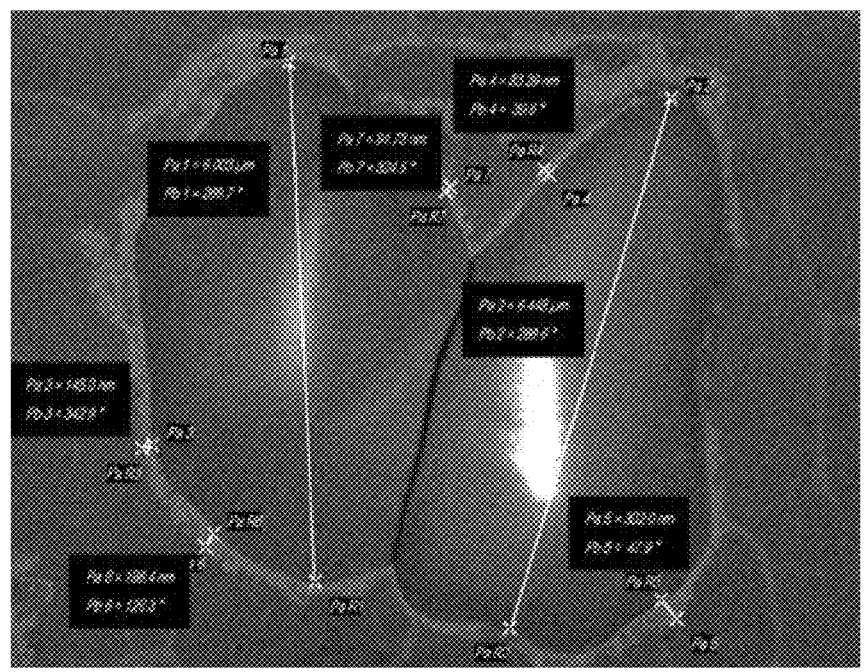
Figure 11A:
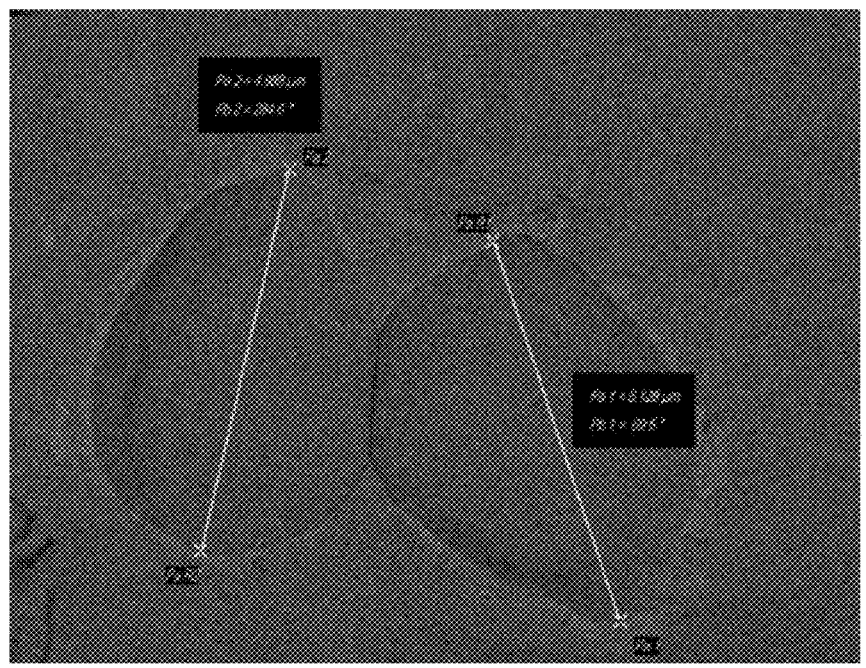
FIG. 11A-11B—cryo-SEM micrographs, produced by the EsB detector, of two E-BPO microcapsules.
Figure 11B:
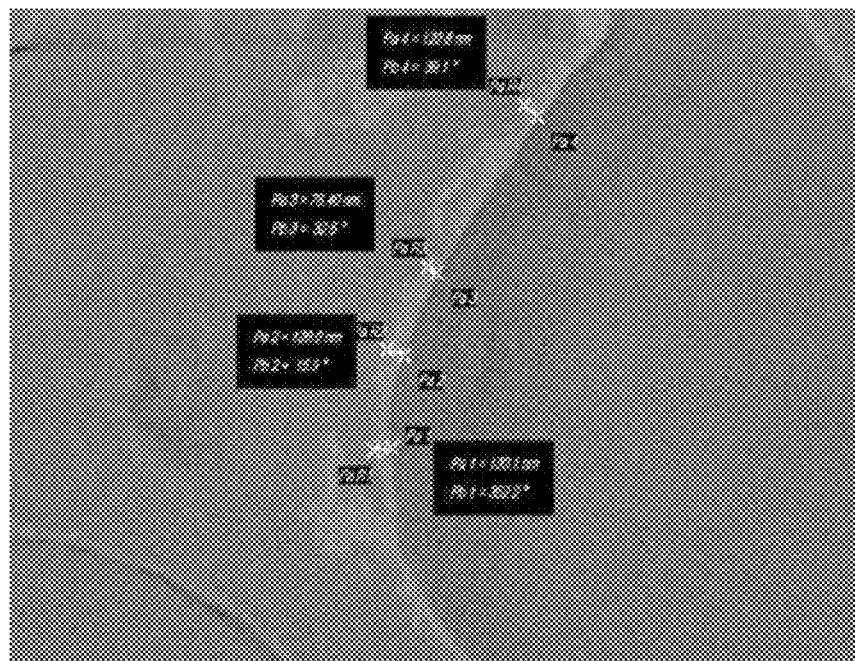
Figure 12A:
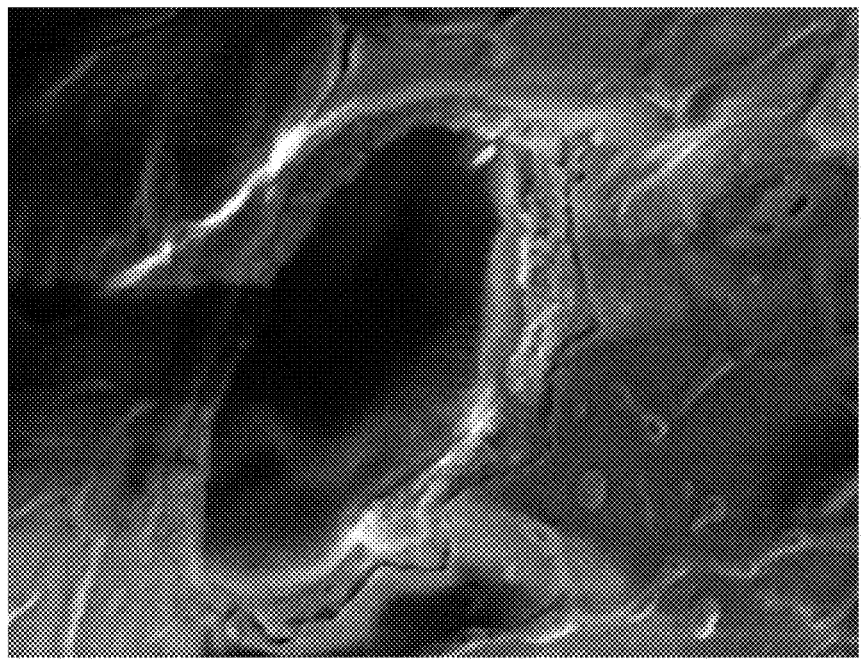
FIG. 12A-12F show representative EDS mapping of an E-BPO microcapsules.
Figure 12B:
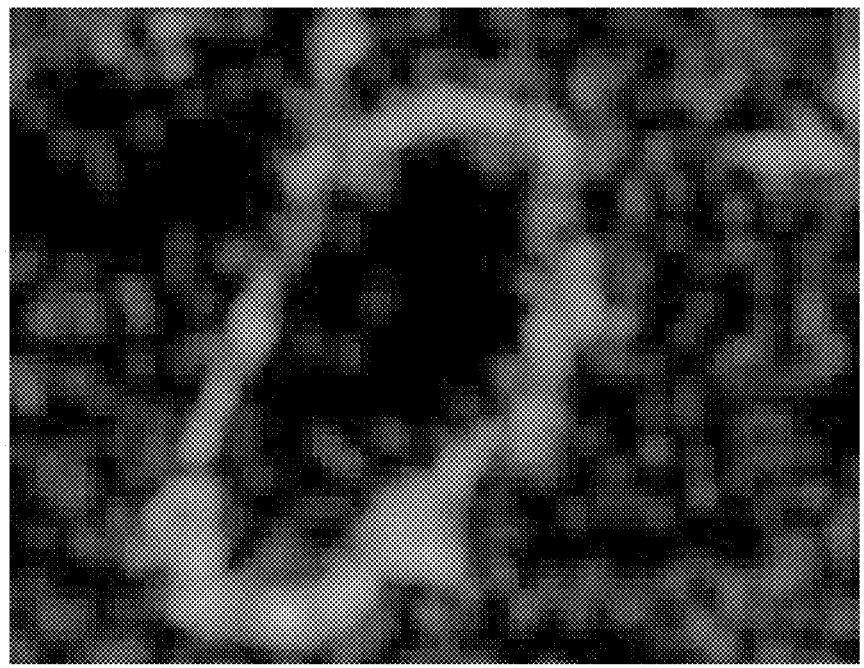
Figure 12C:
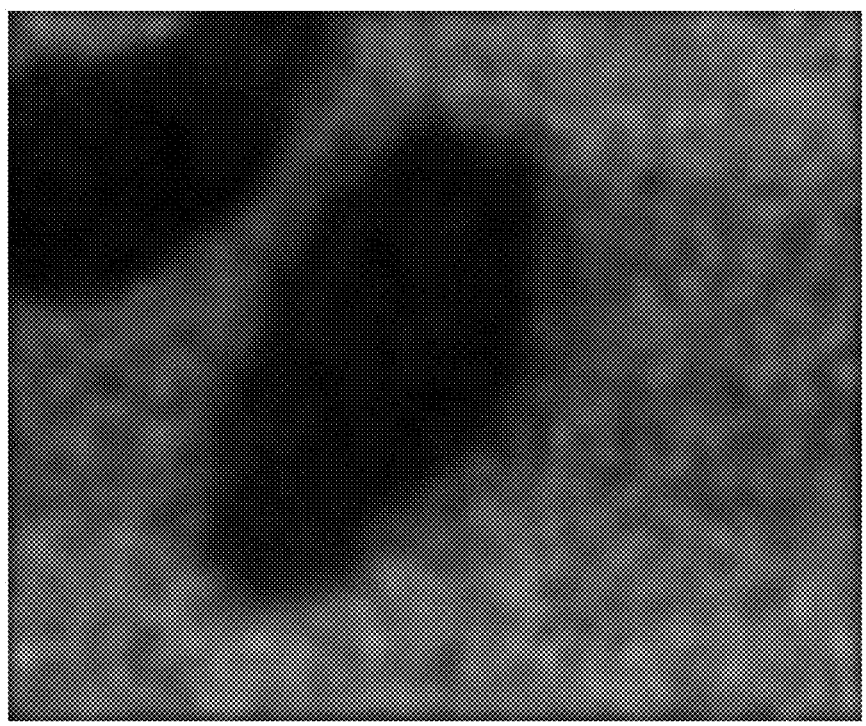
Figure 12D:
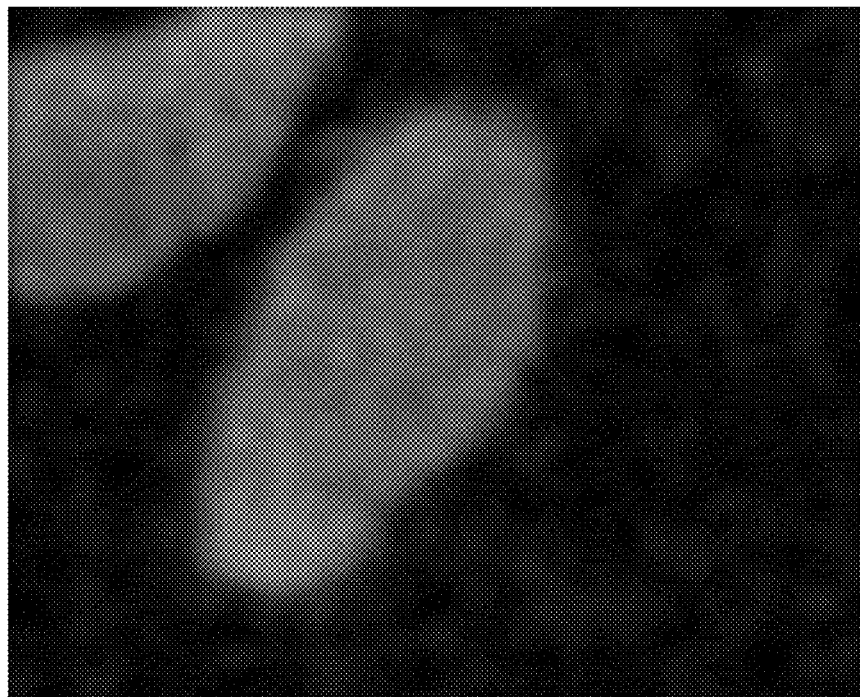
Figure 12E:
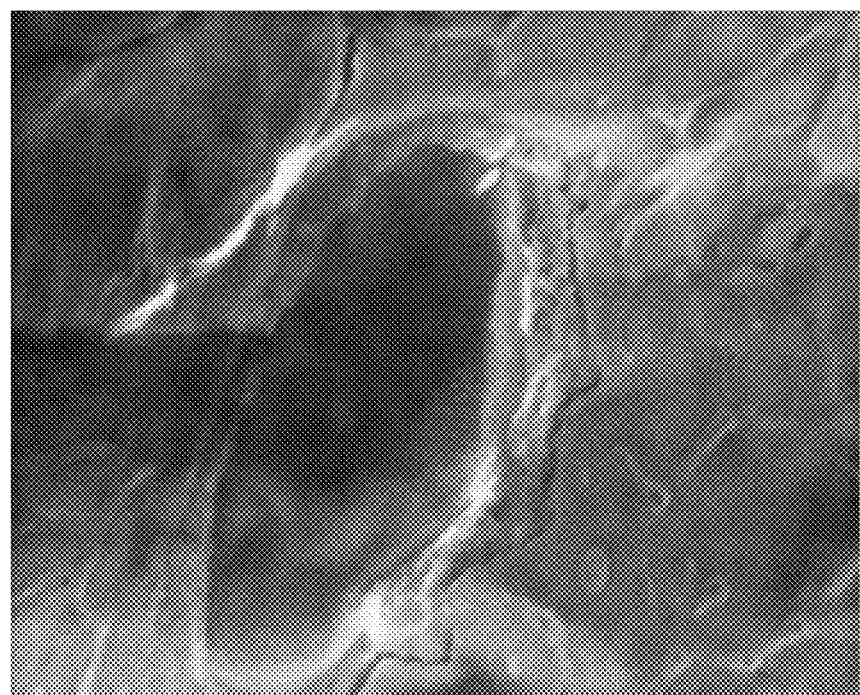
Figure 12F:
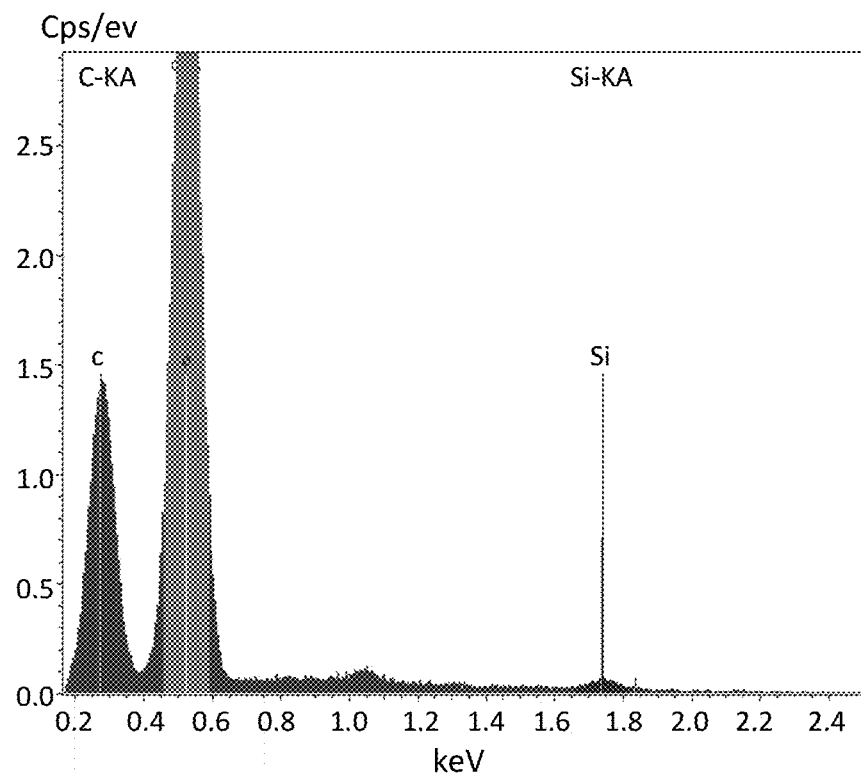

The measured thickness of many E-BPO microcapsules from various E-BPO suspensions revealed shell thickness from 30 nm up to 780 nm. Some representative examples are provided in FIGS. 9-11.

As part of the cryo-SEM analysis, Energy Dispersive Spectroscopy (EDS) analysis was also performed for various E-BPO suspensions. The EDS analysis provides compositional information by identifying the elements in the different specimen domains.

EDS analysis of E-BPO microcapsules revealed, as presented in FIG. 12A-12F, that the microcapsules are predominantly the composed of carbon which corresponds to the BPO (colored red in the EDS maps), the outer shell of the capsule is predominantly composed of silicon which corresponds to the silica shell (colored blue in the EDS maps) and the surrounding of the capsules is predominantly composed of oxygen which corresponds to water (colored green in the EDS maps).

Example 6

SEM and Cryo-SEM Characterization for E-ATRA Suspension 3.4% by Weight

Various batches of E-ATRA suspensions 3.4% (by weight) were characterized by cryo-SEM and SEM imaging.

Methods and Sample Preparation

Cryo-SEM

Samples for cryo-SEM were prepared as described in Example 4.

SEM

Samples for SEM were prepared as described in Example 5.

SEM Images of E-ATRA Microcapsules—Results and Discussion

Figure 13A:
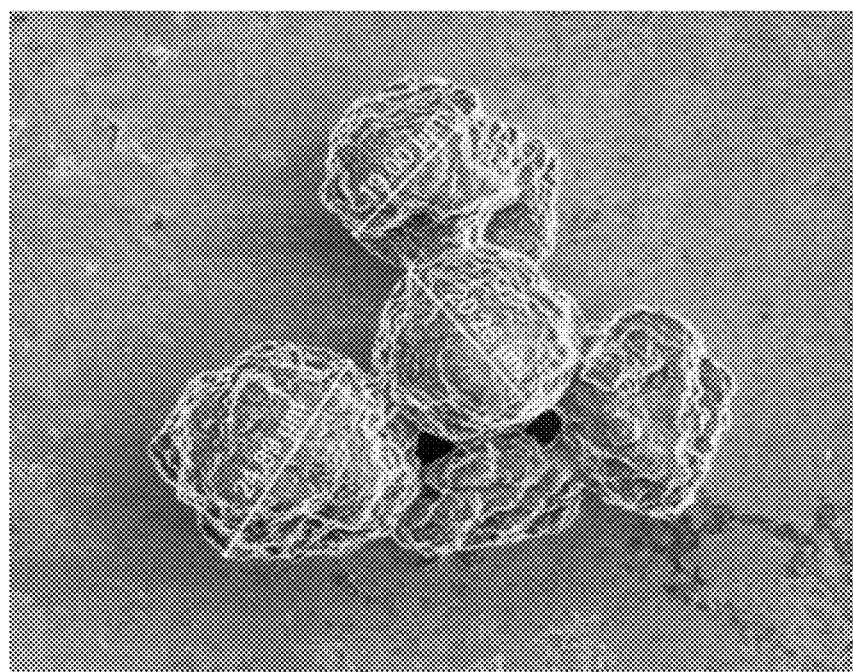
FIG. 13A-13C are representative SEM images of various E-ATRA suspensions. The microcapsules present a spherical structure and their surface is coarse.
Figure 13B:
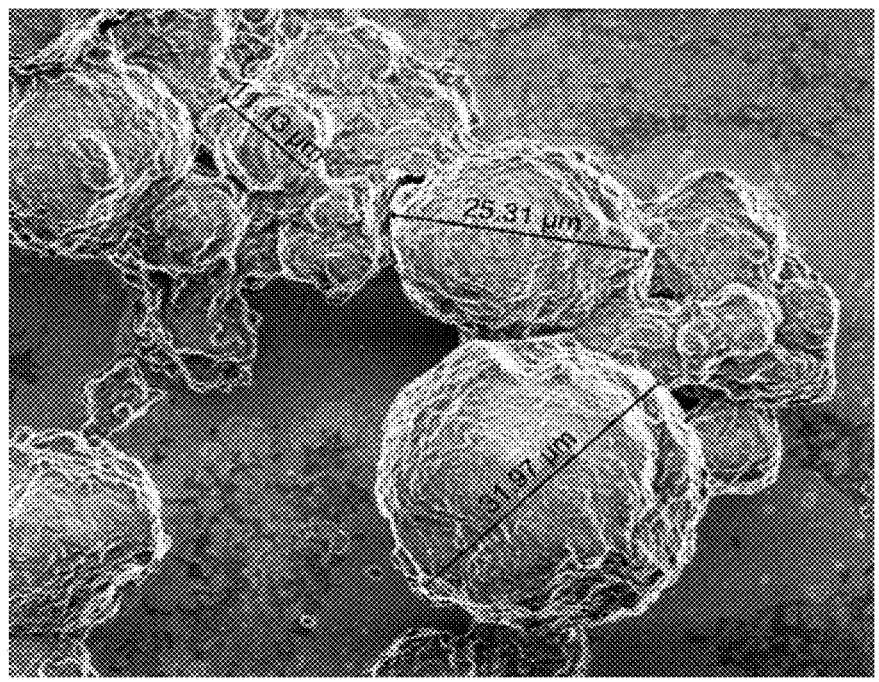
Figure 13C:
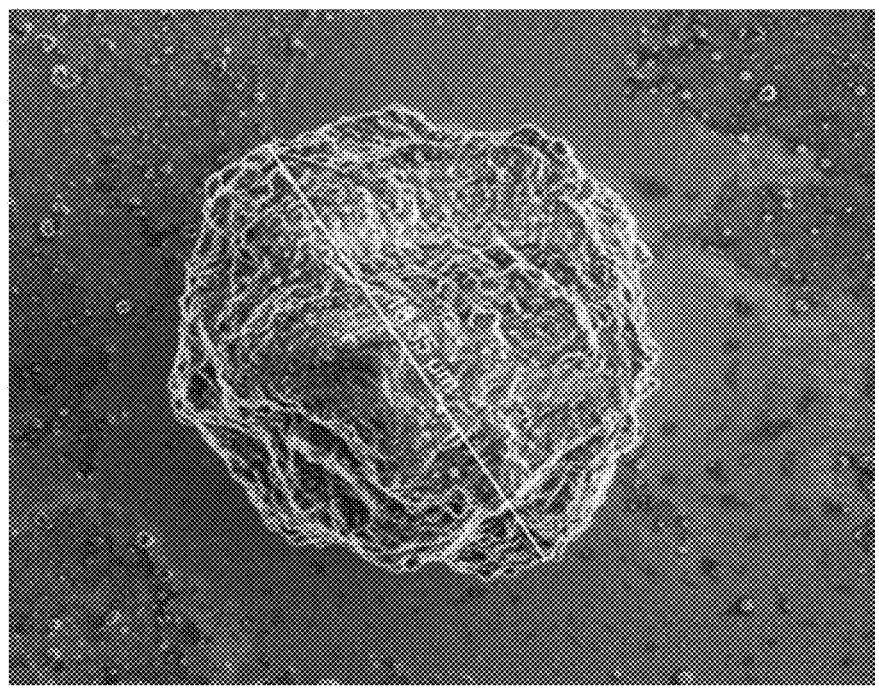

Representative SEM images of E-ATRA microcapsules from various batches are provided in FIG. 13A-13C. As seen in FIGS. 13A-13C, the microcapsules display a spherical structure and their surface is coarse. The size of the E-ATRA microcapsules observed corresponds to the particle size distribution of the suspension tested by Laser light diffraction of Dv(90) NMT 50 μm.

Figure 14:
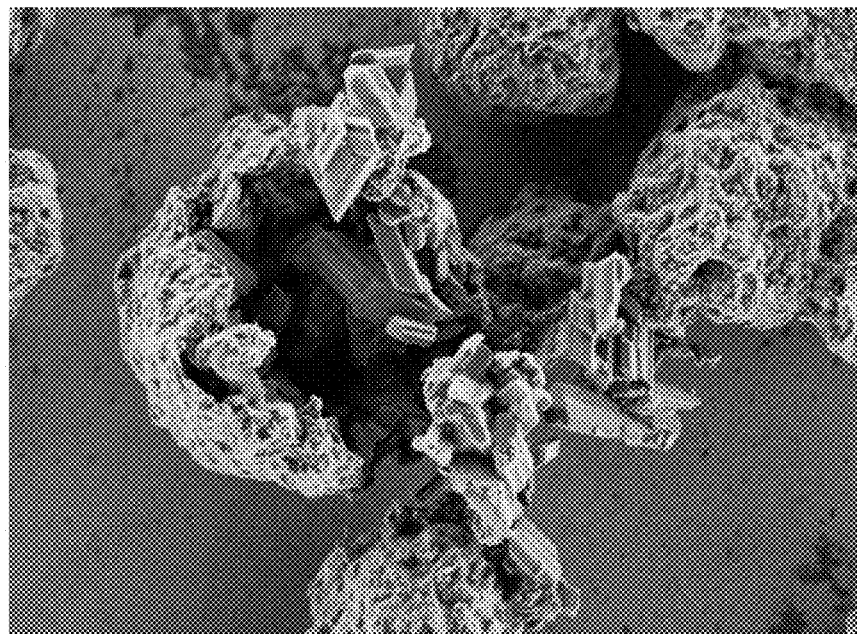
FIG. 14 is A SEM image of an open E-ATRA microcapsule which are rare finding revealed the inner core of the E-ATRA microcapsules. The structure of the tretinoin crystals that immerge out of the microcapsules is crystalline.

In addition to the morphology of the microcapsules, the SEM imaging demonstrated some fractured and opened microcapsules (that fractured during the drying process for the sample preparation) that are rare to find, revealing the structure of the microcapsule core, as shown in FIG. 14. The inner core of the microcapsules revealed the structure of the tretinoin crystals immerging out of the microcapsule. Demonstrating the difference in morphology of the crystalline core and the coarse silica shell.

Cryo-SEM of E-ATRA Microcapsules—Results and Discussion

Various batches of E-ATRA suspensions were also characterized by cryo-SEM.

Figure 15A:
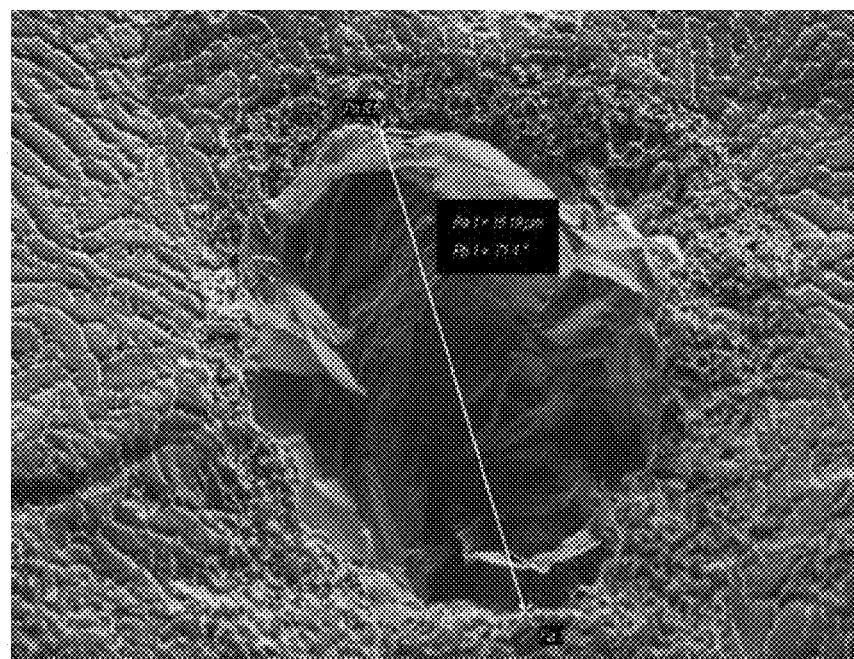
FIG. 15A-15B are cryo-SEM micrographs of an E-ATRA microcapsule.
Figure 15B:
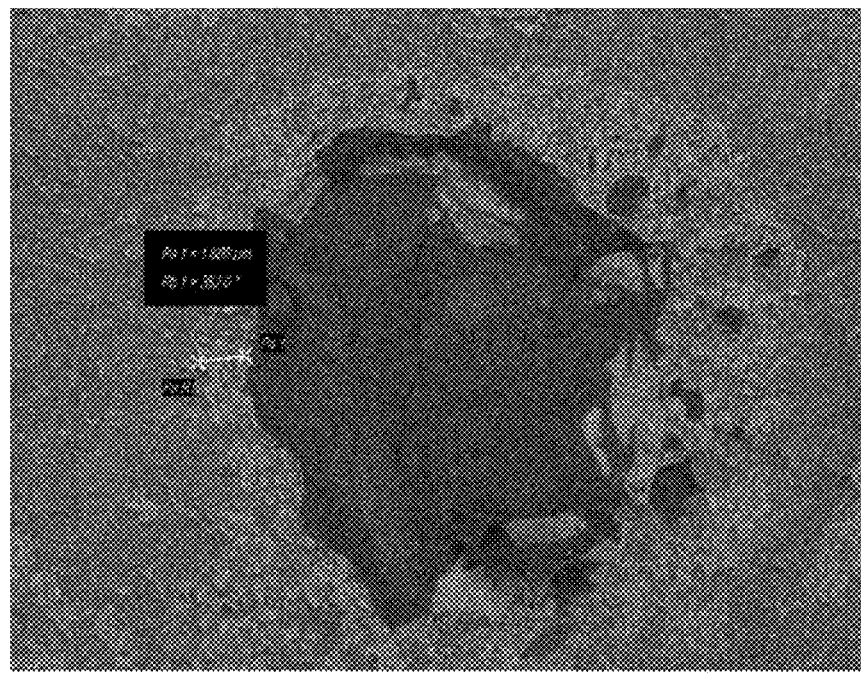
Figure 16A:
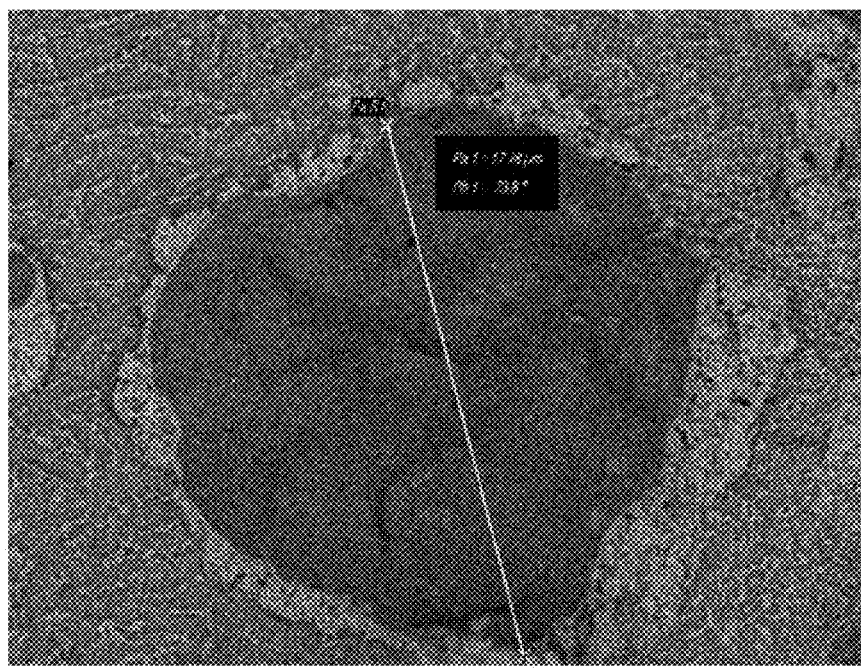
FIG. 16A-16B are cryo-SEM micrographs, produced by the EsB detector, of an E-ATRA microcapsule.
Figure 16B:
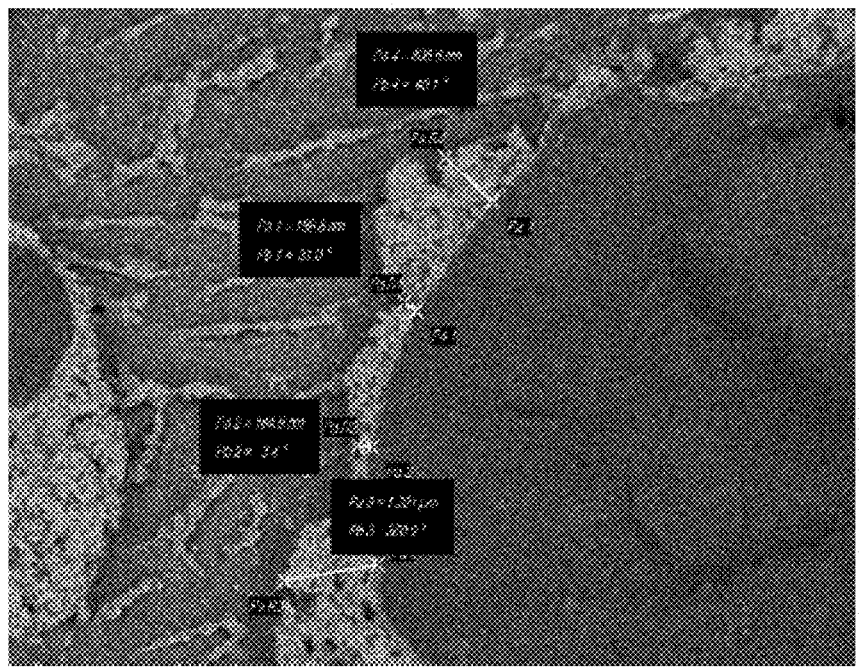
Figure 17A:
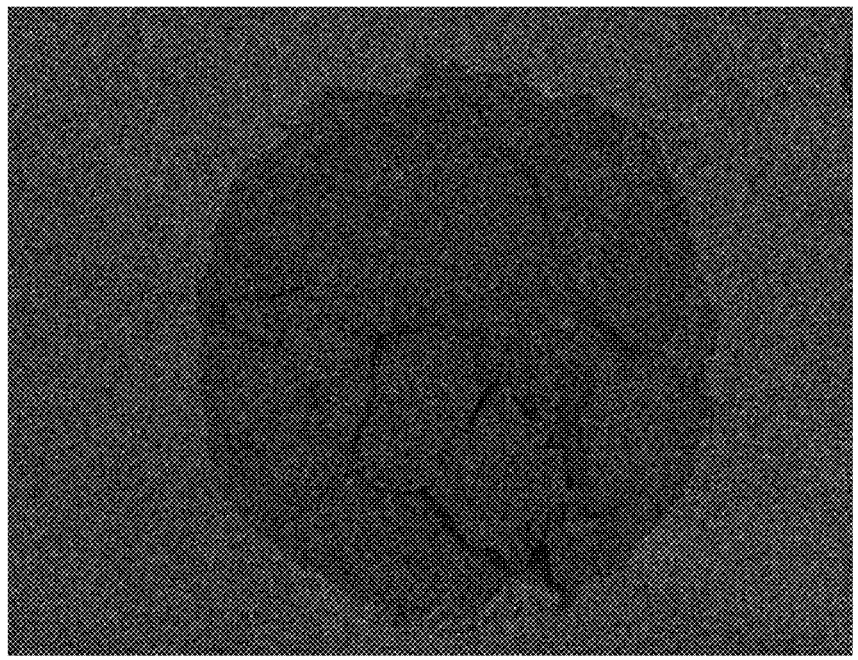
FIG. 17A-17B are cryo-SEM micrographs, produced by the EsB detector, of an E-ATRA microcapsule.
Figure 17B:
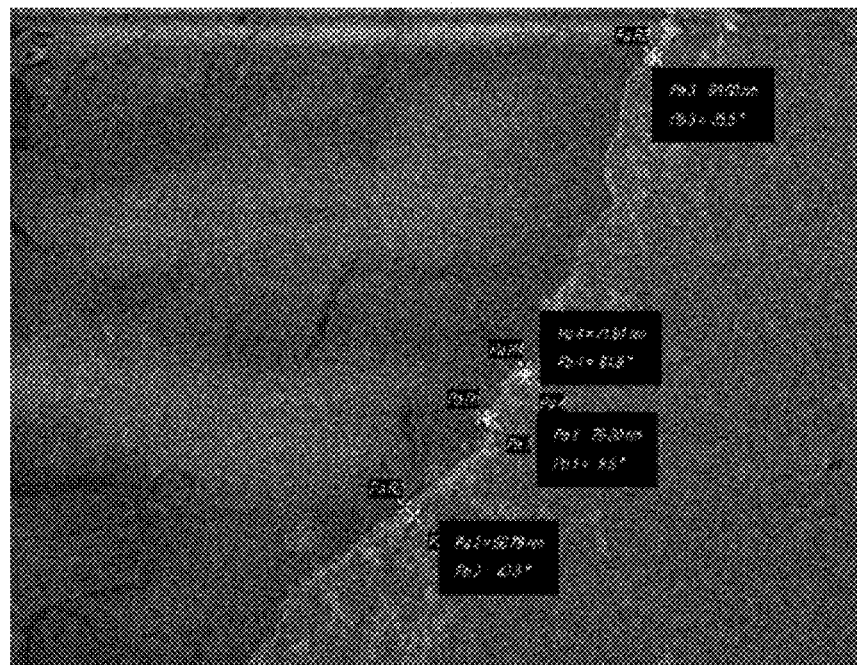
Figure 18A:
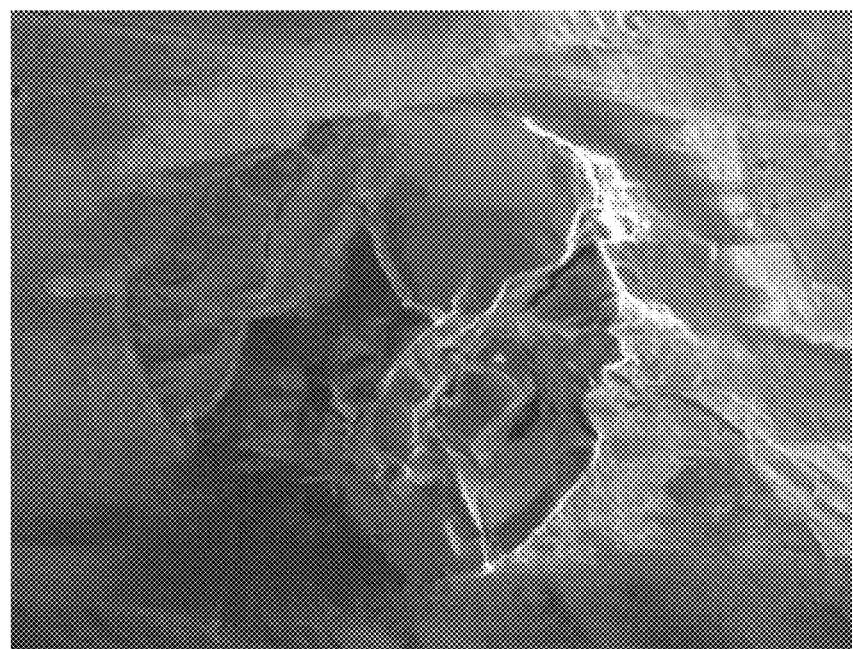
FIG. 18A-18F show a representative EDS mapping of an E-ATRA microcapsule.
Figure 18B:
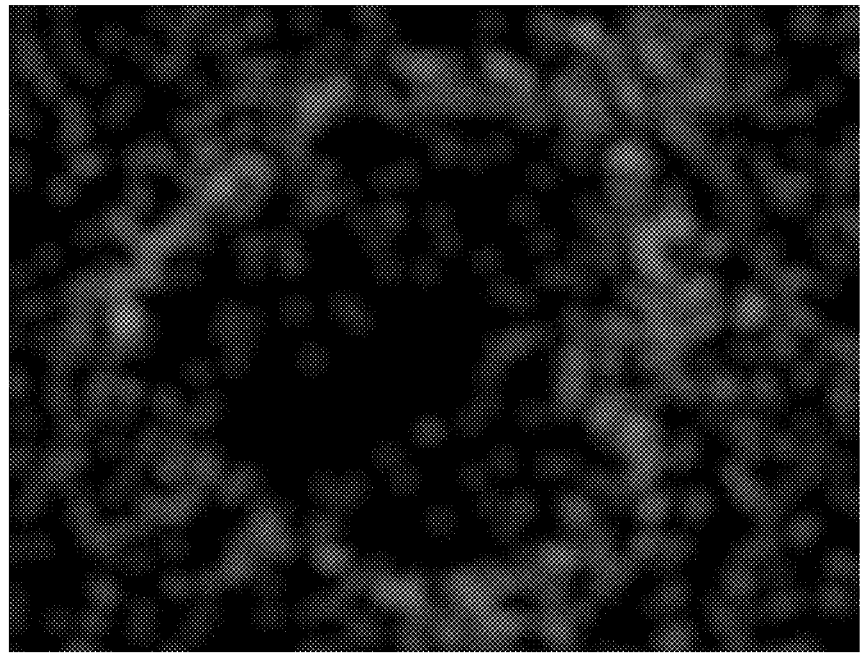
Figure 18C:
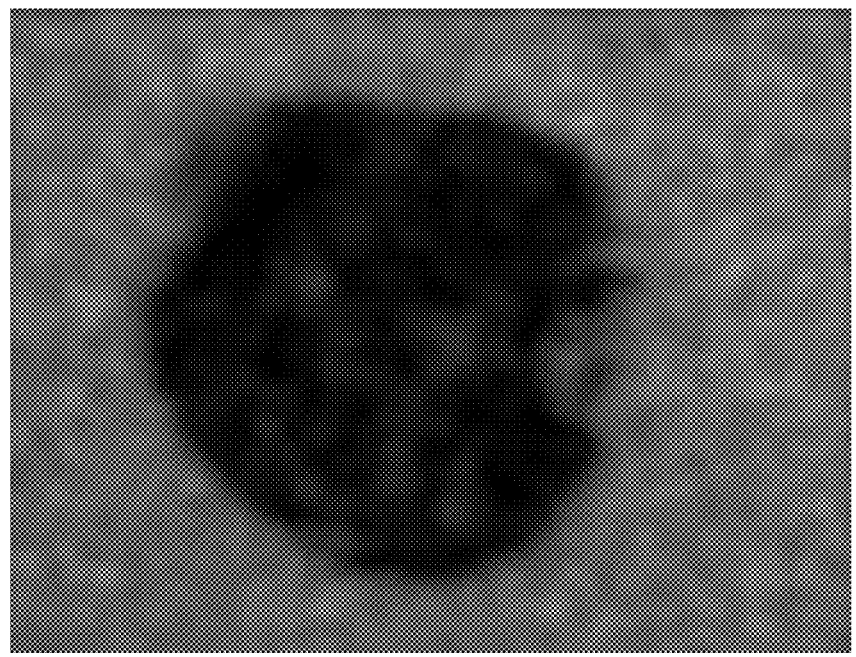
Figure 18D:
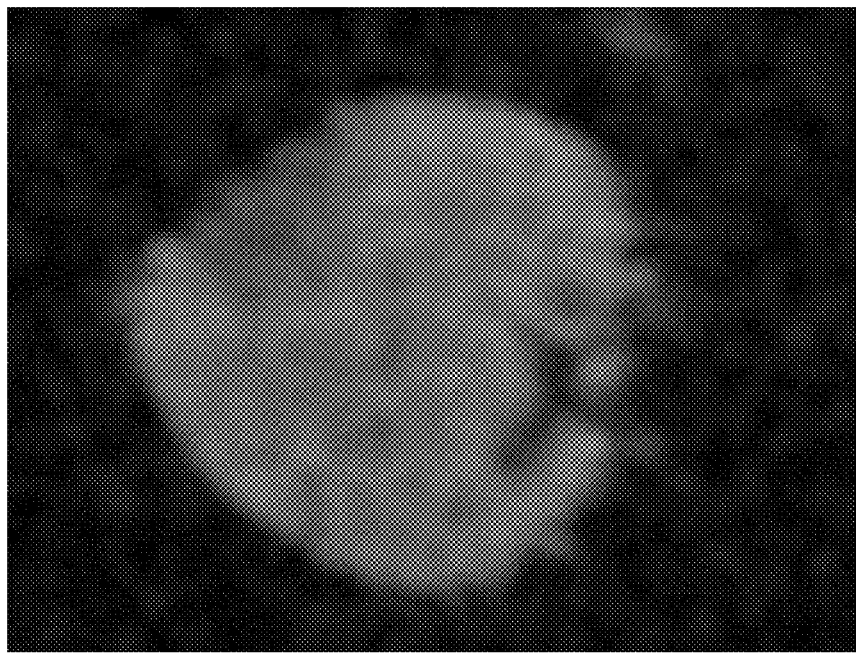
Figure 18E:
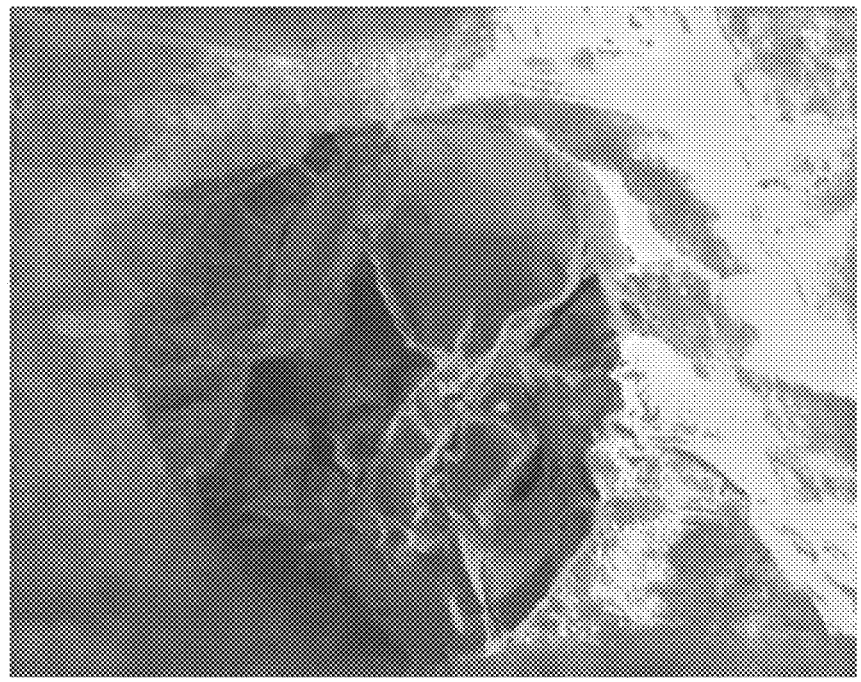
Figure 18F:
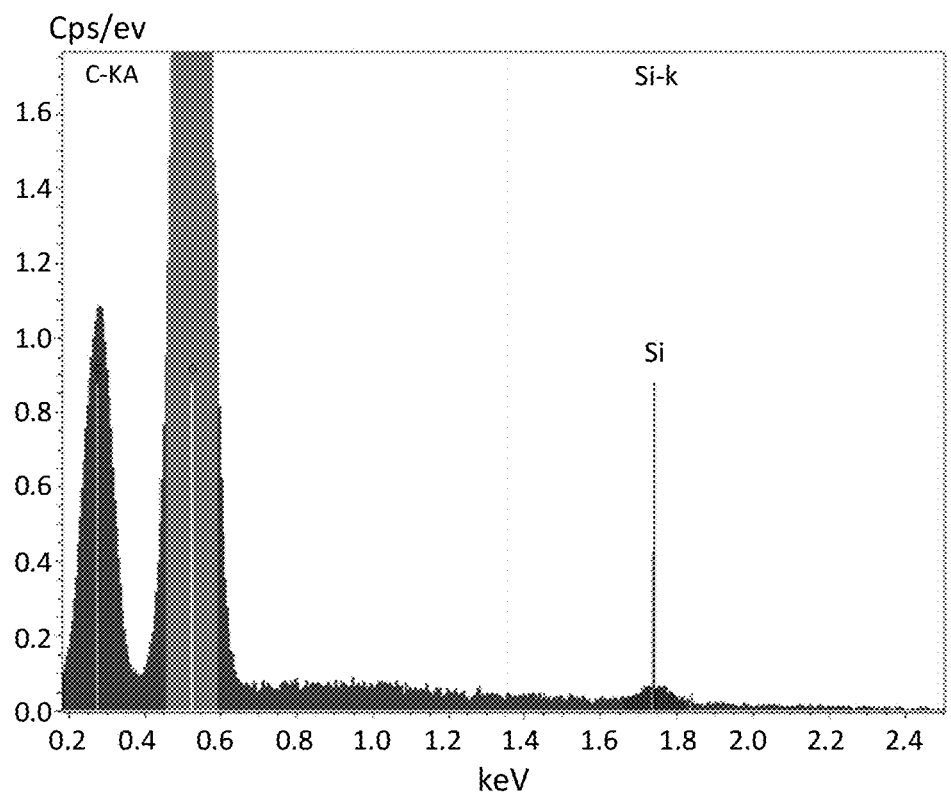

The measured thickness of many E-ATRA microcapsules from various E-ATRA suspensions revealed shell thickness from 50 nm up to 4000 nm. Some representative examples are provided in FIGS. 15-17.

As part of the cryo-SEM analysis, EDS analysis was also performed for various E-ATRA suspensions.

EDS analysis of E-ATRA microcapsules revealed, as presented in FIG. 18A-18F, that the microcapsules are predominantly composed of carbon (colored red in the EDS maps), corresponding to tretinoin, beeswax and squalane. The outer shell of the microcapsules is predominantly composed of silicon (colored blue in the EDS maps), corresponding to the silica shell, and the surrounding of the microcapsules is predominantly composed of oxygen (colored green in the EDS maps), corresponding to the aqueous suspension.

Example 7

Method of Determining the Release of ATRA

Determining the Release of ATRA from an E-ATRA Suspension 3.4% (See Example 2)

An analytical method for determining the release of ATRA (all-trans Retinoic acid) in E-ATRA suspension, 3.4%. The method was intended to release an E-ATRA suspension as an intermediate product. ATRA was released from suspension into a mixture of 1% BHT in Isopropyl Alcohol (510 g) and water (350 g). The amount of released ATRA was determined in comparison with an external standard by HPLC method.

Sample Preparation

Place 100 ml of medium into a dissolution vessel, equilibrate the medium to 32° C. and start mixing.

Tare the balance.

Before each weighing, shake manually the suspension bottle.

Fill a 1 ml syringe with about 0.5 ml of suspension and weigh the syringe.

Start the timer and add a sample from the syringe to the dissolution vessel. Keep 30 seconds between sample additions.

At the specified time intervals, withdraw 1.5 ml and filter through a 0.2 μm syringe filter into an HPLC vial. Wash the sampling cannula and the syringe with the sample solution twice, returning it to the vessel each time before withdrawing. All samples should be taken sequentially. Place samples in the auto-sampler at 4° C. as soon as they are collected.

Calculations

Calculate the amount of released ATRA at first time point $R_1$ (n=1) (%) using the formula:

$$R_1 = \frac{A_{sample} \times \text{inital volume} \times 100 \times 100}{R_f \times W_{sample} \times L.A.}$$

Where:

$A_{sample}$—ATRA peak area arising from Sample $R_f$—Averaged response factor (area/concentration) —average of five response factors of the first standard (WS-1) and one response factor of the second standard (WS-2)

$W_{sample}$—Weight of sample, mg

Initial volume—Volume of medium (100 ml)

L.A. —Content of ATRA in suspension (3.4%)

Calculate the amount of released ATRA for the $n^{th}$ time point, $R_n$(n>1) (%) using the formula:

$$R_n = \left[\frac{\left(A_n \times n^{th} \text{ volume} + \left(1.5 \times \sum_{1}^{n-1} An\right)\right) \times 100}{R_f \times W_{sample} \times L.A.}\right] \times 100$$

where:
  $A_n$—ATRA peak area arising from Sample Preparation at the $n^{th}$ time point
  $R_f$—Averaged response factor (area/concentration) —average of 5 response factors of the first standard (WS-1) and one response factor of the second standard (WS-2)
  $W_{sample}$—Weight of sample, mg
  $n^{th}$ volume—Volume of medium at the $n^{th}$ time point, ml
  1.5—Sampling volume, ml
  $\Sigma_1^{n-1} An$—Sum of ATRA peak areas at all previous time points
  L.A. —Labeled amount of ATRA in suspension (3.4%)

Example 8

Determining the Release of ATRA from a Cream Comprising 0.1% w/w E-ATRA and 3% w/w E-BPO A cream is dissolved in a mixture of two parts of 2% Tween® 80 in pH-6.2 phosphate buffer and 1 part of 4% BHT in isopropyl alcohol. The amount of dissolved ATRA was determined by comparison with an external standard using HPLC analysis.
Sample Preparation
  Place 500 ml of medium into a dissolution vessel, equilibrate the medium to 32° C. to and start mixing.
  Tare the balance. Fill a syringe with ~2 ml of cream and weigh the syringe.
  Start timer and add a sample from the syringe to the dissolution vessel. Keep 30 seconds between sample additions. Weigh the empty syringe. Weight of the sample may vary from 1800 to 2500 mg.
Calculation of the Dissolved ATRA:
  Calculate the amount of dissolved ATRA at the first time point R1 (n=1) (%) using the formula:

$$R_1 = \frac{A_1 \times \text{inital volume} \times 100 \times 100}{R_f \times W_{sample} \times L.A.}$$

Where:
  $A_{sample}$—ATRA peak area arising from Sample Preparation at first time point;
  $R_f$—Averaged response factor (area/concentration) —average of 5 response factors of the first standard (WS-1) and one response factor of the second standard (WS-2);
  $W_{sample}$—Weight of sample in mg;
  Initial volume—Initial volume of medium at first time point, ml;
  L.A. —Labeled amount of ATRA in drug product (0.1%)
Calculate the amount of dissolved ATRA for the $n^{th}$ time point, $R_n$ (n>1) (%) using the formula:

$$R_n = \left[ \frac{\left( A_n \times n^{th} \text{ volume} + \left( 3 \times \sum_1^{n-1} An \right) \right) \times 100}{R_f \times W_{sample} \times L.A.} \right] \times 100$$

Where:
  $A_n$—ATRA peak area arising from Sample Preparation at the $n^{th}$ time point
  $R_f$—Averaged response factor (area/concentration) —average of 5 response factors of the first standard (WS-1) and one response factor of the second standard (WS-2);
  $W_{sample}$—Weight of sample in mg
  $n^{th}$ volume—Volume of medium at the $n^{th}$ time point, mL
  3—Sampling volume, mL;
  $\Sigma_1^{n-1} An$—Sum of ATRA peak areas at all previous time points
  L.A. —Labeled amount of ATRA in drug product (0.1%)

Example 9

The Effect of pH (in the Encapsulation Process of Tretinoin) on the Release Rate of Tretinoin from the Microcapsule A suspension of encapsulated tretinoin (3.4% by weight) was prepared as described in Example 2, where the pH was adjusted to pH between to 3.8 to 4.2 and the effect of different pH was studied. The release rate of tretinoin was determined as described in Example 7.

Figure 19:
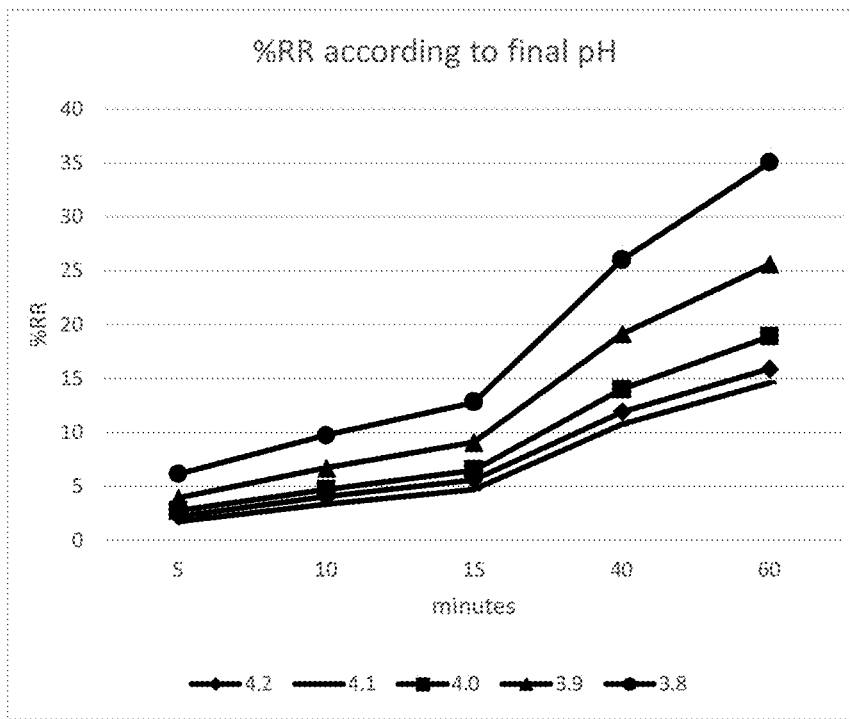
FIG. 19 shows the effect of pH in the preparation of Encapsulated-ATRA (E-ETRA) microcapsules on its release rate. When the pH for the preparation of the tretinoin microcapsules was 4.1, the release rate was the lowest—14.6%.

The release rates of tretinoin at the different pH are presented in Table 1 and FIG. 19.

TABLE 1

Release rates of tretinoin from a suspension of encapsulated tretinoin (3.4%)

| | % RR | | | | |
|---|---|---|---|---|---|
| pH | 5 min | 10 min | 15 min | 40 min | 60 min |
| 4.2 | 2.2 | 4.0 | 5.6 | 11.9 | 15.9 |
| 4.1 | 1.7 | 3.3 | 4.7 | 10.7 | 14.6 |
| 4.0 | 2.7 | 4.7 | 6.5 | 14.0 | 18.9 |
| 3.9 | 3.9 | 6.7 | 9.1 | 19.1 | 25.6 |
| 3.8 | 6.1 | 9.7 | 12.8 | 26.0 | 35.0 |

In the process of preparing encapsulated tretinoin, the acidifying step has an important role in the shell formation. As can be seen, a large difference in % RR is obtained when the acidifying step occurred at pH of 3.8 compared to pH of 3.9 having a lower % RR. Surprisingly an improved, and more stable microcapsule was obtained at pH of between 3.9 and 4.2 (lower % RR) compared to pH 3.8. The acidifying step at pH 4.1 resulted with the lowest release rate after 60 min, thus providing the most stable microcapsules.

Example 10

The Effect of Tretinoin Loading on Release Rate of Tretinoin from Encapsulated Tretinoin A cream Formulation of 0.1% w/w tretinoin and 3% benzoyl peroxide, wherein both tretinoin and benzoyl peroxide are encapsulated was prepared, as described in Example 3 with different loading concentrations of tretinoin. The release rate of tretinoin was measured as determined in Example 8 and summarized in Table 2.

TABLE 2

Loading Percentage of tretinoin in the formulation in relation to the % of tretinoin release and the % impurities

| | T = 0 | | | | | | | After 2 weeks at 40° C. Assay and related compounds of ATRA | | |
|---|---|---|---|---|---|---|---|---|---|---|
| | Assay and related compounds of ATRA | | % ATRA released | | | | | | | |
| % of E-ATRA | Assay, % | RRT0.46*, % | 30 min | 1 h | 2 h | 4 h | 6 h | Assay, % | 5,6-epoxy RA, % | Total RC**, % |
| Tretinoin loading 11% | 0.0995 | <0.1 | 69.3 | 81.4 | 88 | 87.5 | 83.5 | 0.0883 | 1.5 | 4.3 |
| Tretinoin loading 14% | 0.1031 | <0.1 | 24.4 | 39.7 | 58.2 | 72.5 | 75.9 | 0.0988 | 0.61 | 1.76 |
| Tretinoin loading 17% | 0.0982 | | 17.4 | 28.2 | 42.1 | 60.1 | 70.3 | 0.0948 | 0.5 | 1.49 |
| Tretinoin loading 20% | 0.0968 | | 19.7 | 32.5 | 46.9 | 60.8 | 67.9 | 0.0948 | 0.36 | 0.96 |
| Tretinoin prepared according to US 2013/0095185-Example 1 | 0.0984 | <0.1 | 16.7 | 30.5 | 54.8 | 72.7 | 79.9 | 0.0951 | 0.53 | 1.25 |

*RRT0.46 refers to the relative retention time at 0.46 in the assay- referring to the concentration of 5,6 epoxy retinoic acid.
**Total RC refers to the concentration of decomposition compounds of tretinoin ("related compounds"), including 5,6 epoxy retinoic acid.

Figure 20:
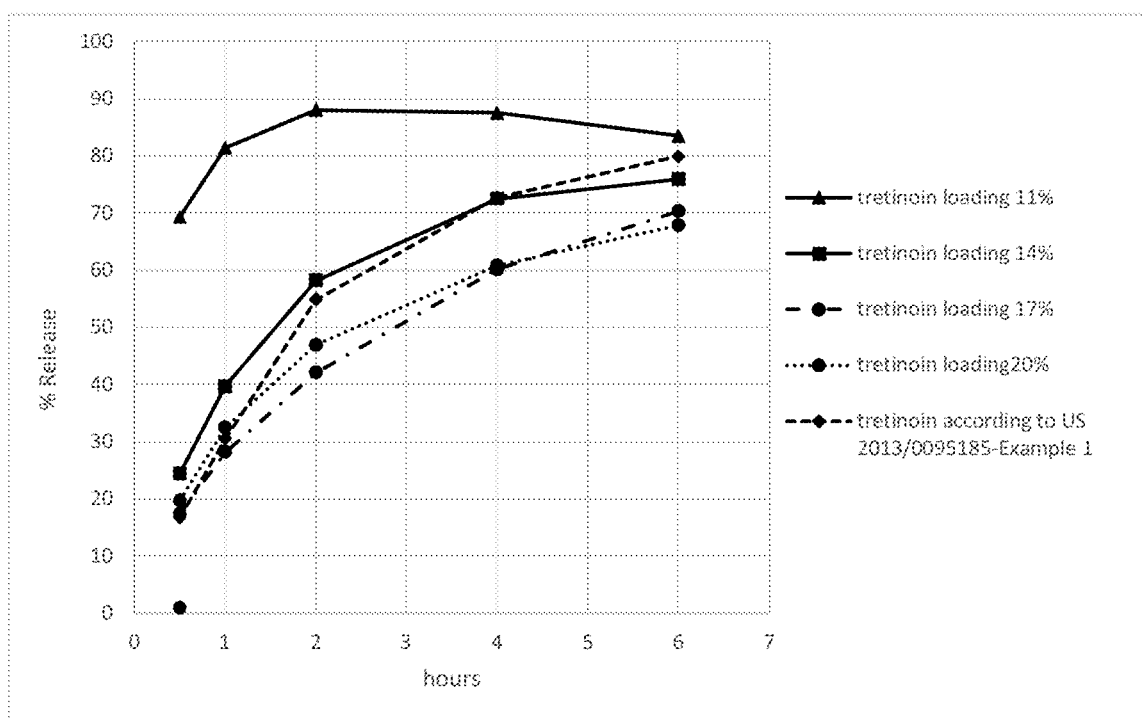
FIG. 20 shows the effect tretinoin loading in the oily phase in the preparation of E-ATRA microcapsules on its release rate.

As shown also in Table 2 and FIG. 20, the higher the percentage of the tretinoin in the formulation, the lower was the percentage of the release. i.e. when having 20% tretinoin in the suspension, after 2 h the % of the release was 46.9%, whereas in 11% tretinoin, the release was 88%.

As to the impurities, the higher the percentage of the tretinoin in the formulation, the lower the percentage of the impurities, i.e. after 2 weeks at 40° C., the formulation that had 20% tretinoin, resulted 0.96% of total impurities, whereas the formulation that had 11% tretinoin 4.3% of total impurities. Furthermore, the higher the loading of tretinoin, the lower the percentage of 5,6-epoxyretinoic acid. i.e. the formulation that had 20% tretinoin in the formulation, resulted 0.36% of 5,6-epoxyretinoic acid, whereas the formulation that had 11% tretinoin in the formulation gave 1.5% of 5,6-epoxyretinoic acid.

Example 11

Microencapsulation Efficiency of ATRA

In this Example the correlation between the entrapment efficiency (EE) (=microencapsulation efficiency) of E-ATRA and the stability of the microcapsules was studied.
Analytical Method of Determining the Microencapsulation Efficiency of ATRA
Analytical Method of Determining the Microencapsulation Efficiency of Tretinoin in E-ATRA Suspension An analytical method for determining the microencapsulation efficiency of ATRA (All-Trans Retinoic acid) in an E-ATRA, suspension 3.4% w/w. The method is intended for release of the suspension as an intermediate product.

The E-ATRA suspension was dispersed in a mixture of 1% w/v BHT in Isopropyl Alcohol-water (50:50 v/v). After 5 minutes, the sample was withdrawn and filtered.

The amount of free, non-encapsulated ATRA dissolved in the medium is determined by comparison with an external standard by HPLC analysis. The microencapsulation efficiency of ATRA was determined by the mass balance with respect to the labeled ATRA content of the suspension.

The free, non-encapsulated ATRA concentration (% w/w) was calculated using the following equation:

$$\text{Free} = \frac{A_{sample} \times V \times 100}{R_f \times W_{sample}}$$

where:

$A_{sample}$ ATRA peak area arising from Sample Preparation;

$R_f$ Averaged response factor (area/concentration) —average of 5 response factors of the first standard (WS-1) and one response factor of the second standard (WS-2);

$W_{sample}$ Weight of sample, mg;

V Volume of medium, ml (200);

The microencapsulation efficiency (%), was calculated using the following equation:

$$\text{Microencapsulation Efficiency} = \frac{3.4 - Av.Free}{3.4} \times 100$$

where:

Av. Free Averaged result of the free, non-encapsulated BPO concentration, as calculated above;

3.4 The labeled content of ATRA in suspension in % w/w.

Analytical Method of Determining the Microencapsulation Efficiency of Tretinoin in E-BPO 3% w/w/E-ATRA 0.1% w/w Cream An analytical method for determining the microencapsulation efficiency of ATRA (All-Trans Retinoic acid) in E-BPO/E-ATRA cream, 3%/0.1%. The method is intended for release and stability study.

The cream was dispersed in water (100 ml) by magnetic stirring for 30-40 min and then 100 ml of an organic solvent (1% BHT in IPA) was added. After 5 minutes, a sample was withdrawn and filtered. The amount of free, non-encapsulated ATRA was determined by comparison with an external standard by HPLC analysis. The microencapsulation efficiency of ATRA was determined by the mass balance with respect to the labeled ATRA content of the cream.

The free, non-encapsulated ATRA concentration (% w/w) was calculated using the following equation:

$$\text{Free} = \frac{A_{sample} \times V \times 100}{R_f \times W_{sample}}$$

where:
$A_{sample}$ ATRA peak area arising from Sample Preparation;
$R_f$ Averaged response factor (area/concentration) —average of 5 response factors of the first standard (WS-1) and one response factor of the second standard (WS-2);
$W_{sample}$ Weight of sample in mg;
V Volume of medium, mL (200).

The microencapsulation efficiency (%) was calculated using the following equation:

$$\text{Microencapsulation Efficiency} = \frac{0.1 - Av.Free}{0.1} \times 100$$

where:
Av. Free Averaged result of the free, non-encapsulated ATRA concentration, as calculated above.
0.1 The labeled content of ATRA in cream in % w/w.

Example 12

Production of E-ATRA with Different EE (Entrapment Efficiency/Microencapsulation Efficiency)

E-ATRA 3.4% suspension was prepared as described in Example 2. In beaker 3 L was added about 1 L suspension and start high-shear of 4500 rpm (4.5 m/s homogenizes, 45-10) after 30 sec, 1 min, 2 min, 4 min, 6 min, 10 min of homogenization was done sampling were taken to the EE test as described in example 11. The rational is that by introducing the suspension to high shear, the encapsulation and entrapment of tretinoin is reduced.

TABLE 3

Calculation of entrapment efficiency (EE) (=microencapsulation efficiency) of E-ATRA suspensions after high shear and its effect on the percentage of release of tretinoin.

| high shear duration | % release (by dissolution) | | | | | EE |
|---|---|---|---|---|---|---|
| | 5 min | 10 min | 15 min | 40 min | 60 min | |
| 0 sec | 2.1 | 4.2 | 6.2 | 14.5 | 20.4 | 99.9 |
| 30 sec | 14.4 | 25.2 | 34.7 | 65.0 | 75.1 | 95.6 |
| 1 min | 18.4 | 32.1 | 44.1 | 76.4 | 83.7 | 94.1 |
| 2 min | 31.8 | 54.1 | 70.1 | 91.8 | 93.6 | 86.2 |
| 4 min | 49.4 | 75.9 | 86.9 | 91.9 | 92.4 | 66.7 |

As shown, the longer the time that the E-ATRA suspension was homogenized, the greater the % of the release was and lower entrapment efficiency (EE) (=microencapsulation efficiency).

Four E-ATRA suspensions with different EEs were formulated into E-BPO/E-ATRA 3%/0.1% creams, and tested up to 3 w at 40 C, as shown in Table 4:

TABLE 4

Stability of a formulation of E-BPO/E-ATRA 3%/0.1% creams with different E-ATRA microencapsulation efficiency.

| E-ATRA suspension | T = 0 | | | 1 w 40° C. | | | 2 w 40° C. | | | 3 w 40° C. | | |
|---|---|---|---|---|---|---|---|---|---|---|---|---|
| | Assay, % | RRT0.44*, % | Total of RC | Assay, % | RRT0.44, % | Total of RC | Assay, % | RRT0.44*, % | Total of RC | Assay, % | RRT0.44*, % | Total of RC**, % |
| 98% EE | 0.0949 | 0.15 | 0.15 | 0.0935 | 0.54 | 0.89 | 0.0932 | 0.76 | 1.32 | 0.0903* | 1.13 | 2.24 |
| | 0.0896 | 0.12 | 0.12 | 0.0886 | 0.5 | 0.86 | 0.087 | 0.76 | 1.55 | 0.0859 | 1.03 | 2.04 |
| 95.6% EE | 0.0902 | <0.1 | <0.1 | 0.0897 | 0.59 | 1.1 | 0.0869 | 0.98 | 1.8 | 0.0860 | 1.35 | 2.46 |
| 94.1% EE | 0.0908 | 0.11 | 0.11 | 0.0904 | 0.59 | 1.08 | 0.0878 | 1.01 | 1.86 | 0.0865 | 1.41 | 2.70 |
| 86.2% EE | 0.0913 | 0.14 | 0.14 | 0.0902 | 0.62 | 1.24 | 0.0865 | 1.19 | 2.17 | 0.0855 | 1.64 | 2.96 |

*RRT0.44 refers to the relative retention time at 0.44 in the assay- referring to the concentration of 5,6 epoxy retinoic acid.
**Total RC refers to the concentration of decomposition compounds ("related compounds") of tretinoin, including 5,6 epoxy retinoic acid.

Conclusion: E-ATRA with lower EE are less stable when formulated.

As shown in Table 4, the higher the EE %, the lower % of impurities. i.e. after 3 w in 40° C. the formulation that had E-ATRA 98% EE had total impurities of 2.24/2.04% whereas in the formulation that had E-ATRA 86.2% EE had total impurities of 2.96%.

Furthermore, the higher the EE %, the lower the percentage of 5,6-epoxyretinoic acid. i.e. after 3 w in 40° C. the formulation that had E-ATRA 98% EE had 1.13/1.03% of 5,6-epoxyretinoic acid. whereas in the formulation that had E-ATRA 86.2% EE had 1.64% of 5,6-epoxyretinoic acid.

Example 13

Release Rate of E-BPO as Change in Temperature

15% E-BPO water suspension, as described in Example 1, wherein different temperature during encapsulation was studied.

Results

In this work two E-BPO 15% suspensions were used with different BPO RR profile at Time Zero (TZ).

Table 5 shows release rates after 60 min of fresh E-BPO suspensions that are influenced by encapsulation temperature, when the temperature during encapsulation was higher, the lower was the percentage of the rate release. i.e. at 28° C. the release rate was 48%, whereas at 40° C. the release rate was 12%.

BPO is released into a mixture of acetonitrile-water (45:55) at ambient temperature. The amount of release BPO is determined in comparison with an external standard by HPLC method.

TABLE 5

Release rate of BPO as a function of the encapsulation temperature

| Encapsulation Temperature | BPO Release Rate after 60 min |
|---|---|
| 25° C. | 68% |
| 28° C. | 48% |
| 32° C. | 26% |
| 38° C. | 17% |
| 40° C. | 12% |

Example 14

Microencapsulation Efficiency (ME) of BPO
Analytical Method of Determining the Microencapsulation Efficiency of Tretinoin in E-BPO Suspension Analytical method for determining the microencapsulation efficiency of Benzoyl Peroxide in an EBPO suspension, 15%. The method was intended for release of the suspension as an intermediate product.

The E-BPO suspension was dispersed in a mixture of ACN-water (45:55 v/v). After 5 minutes of mixing, the sample was withdrawn and filtered. The amount of free, non-encapsulated BPO dissolved in the medium was determined by comparison with an external standard by HPLC analysis. The microencapsulation efficiency of BPO was determined by the mass balance with respect to the labeled BPO content of the suspension.

The free, non-encapsulated BPO concentration (% w/w) was calculated using the following equation:

$$\text{Free} = \frac{A_{sample} \times V \times 100}{R_f \times W_{sample}}$$

where:
A sample BPO peak area arising from Sample Preparation;
$R_f$ Averaged response factor (area/concentration) —average of 5 response factors of the first standard (WS-1) and one response factor of the second standard (WS-2);
$W_{sample}$ Weight of sample in mg;
V Volume of medium, mL (200).

The microencapsulation efficiency value (%), was calculated using the following equation:

$$\text{Microencapsulation Efficiency} = \frac{15 - Av.Free}{15} \times 100$$

where:
Av. Free Averaged result of the free, non-encapsulated BPO concentration, as calculated above.
15 The labeled content of BPO in suspension in % w/w Analytical Method of Determining the Microencapsulation Efficiency of BPO in E-BPO 3% w/w/E-ATRA 0.1% w/w Cream An analytical method for determining the microencapsulation efficiency of Benzoyl Peroxide in E-BPO/E-ATRA cream, 3%/0.1%. The method was intended for release and stability study.

The cream was dispersed in water (100 ml) by magnetic stirring for 25-30 min and then an organic solvent (90% IPA) was added. After 5 minutes, a sample was withdrawn and filtered. The amount of free, non-encapsulated BPO is determined by comparison with an external standard by HPLC analysis. The microencapsulation efficiency of BPO was determined by the mass balance with respect to the labeled BPO content of the cream.

The free, non-encapsulated BPO concentration (% w/w) was calculated using the following equation:

$$\text{Free } BPO = \frac{A_{sample} \times V \times 100}{R_f \times W_{sample}}$$

where:
$A_{sample}$ BPO peak area from Sample injection;
$R_f$ Averaged response factor (area/concentration) —average of 5 response factors of the first standard (WS 1) and one response factor of the second standard (WS 2);
$W_{sample}$ Net weight of the sample, mg;
V Total medium volume, mL (200);

The microencapsulation efficiency value (%), was calculated using the following equation:

$$ME, \% = \frac{3 - \text{Free } BPO_{avg}}{3} \times 100$$

Where:
Free $BPO_{avg}$ Averaged result of the free BPO, non-encapsulated BPO content, as calculated above;
ME Microencapsulation efficiency, %
3 The labeled content of BPO in DP, % w/w.

What is claimed:

1. A microcapsule comprising a core encapsulated by a silica based shell, wherein said core comprises solid benzoyl peroxide (BPO), wherein said benzoyl peroxide is released at a dissolution rate of between 12%-60% weight/h as measured in a medium of 55%:45% mixture of water and acetonitrile at ambient temperature, and wherein said microcapsule is prepared by a process comprising:
   a) contacting solid benzoyl peroxide particulate matter, with a first cationic additive being a cationic surfactant, to obtain a dispersion in an aqueous medium, said particulate matter having positive charges on its surface;
   b) adding an aqueous solution comprising silicate salt to said dispersion of said particulate matter, under conditions wherein said silicate salt precipitates onto the surface of the particulate matter, and acidifying to thereby form a solid, water-insoluble particulate matter that has a metal oxide layer coated thereon;
   c) contacting, in a medium consisting of an aqueous medium, the particulate matter coated with a silica based layer of the preceding step with a surface adhering additive being one or both of (i) a second cationic additive being a cationic polymer and (ii) a non-ionic additive, to obtain a dispersion of said coated particulate matter having an adhering additive on the surface thereof in said aqueous medium;
- d) bringing the dispersion obtained in step (c) into contact with an aqueous solution of a sodium silicate, under conditions wherein said sodium silicate precipitates onto the surface of said coated particulate matter, and acidifying to thereby form a solid, water-insoluble particulate matter that has a further silica based layer coated thereon;
- e) repeating steps (c) and (d) between 3-50 times at a temperature of between 28° C. to 40° C.; and
- f) optionally, after completion of step (e), aging the dispersion to obtain said encapsulated benzoyl peroxide.

2. The microcapsule according to claim 1, wherein said cationic surfactant is cetyltrimethyl ammonium chloride (CTAC) or wherein said cationic polymer is poly(dimethyldiallylammonium chloride) (PDAC), or a combination thereof.

3. The microcapsule according to claim 1, wherein said step (e) is between 5-7 times (i.e. steps (c) and (d) are repeated between 5-7 times).

4. The microcapsule according to claim 1, wherein said acidifying step, in step (b), comprises addition of an acidic solution comprising at least one weak acid and said metal oxide salt is a silicate salt.

5. The microcapsule according to claim 4, wherein said weak acid comprises citric acid, lactic acid or a mixture thereof.

6. The microcapsule according to claim 1, wherein the average diameter of said microcapsule is less than 50 micrometers.

7. The microcapsule according to claim 1, wherein the thickness of the silica based shell ranges between 25 nm and 3000 nm.

8. The microcapsule according to claim 1, wherein said microcapsule is stable for a period of between about 2 weeks to about 3 years at room temperature.

9. A suspension comprising the microcapsule according to claim 1.

10. A pharmaceutical composition comprising the microcapsule according to claim 1, and a pharmaceutically acceptable carrier or excipient.

11. A pharmaceutical composition comprising the suspension of claim 9, and a pharmaceutically acceptable carrier or excipient.

12. The pharmaceutical composition according to claim 10, wherein the carrier is in a form of an ointment, a cream, a lotion, an oil, a solution, an emulsion, a gel, a paste, a milk, an aerosol, a powder or a foam.

13. The pharmaceutical composition according to claim 11, wherein the carrier is in a form of an ointment, a cream, a lotion, an oil, a solution, an emulsion, a gel, a paste, a milk, an aerosol, a powder or a foam.

14. The pharmaceutical composition according to claim 10, wherein the microcapsules have microencapsulation efficiency of at least 75%.

15. The pharmaceutical composition according to claim 11, wherein the microcapsules have microencapsulation efficiency of at least 75%.

16. A pharmaceutical composition comprising the microcapsules according to claim 1, wherein the benzoyl peroxide is in an amount of about 3% by weight of said composition and the composition further comprises microcapsules comprising tretinoin or a pharmaceutically acceptable salt thereof in an amount of about 0.1% by weight of said composition; and a pharmaceutically acceptable carrier or excipient.

17. A pharmaceutical composition comprising microcapsules comprising benzoyl peroxide according to claim 1, wherein the benzoyl peroxide is in an amount of about 3% by weight of said composition; and the composition further comprises microcapsules comprising tretinoin or a pharmaceutically acceptable salt thereof in an amount of about 0.1% by weight of said composition and; and a pharmaceutically acceptable carrier or excipient, wherein the microcapsules comprising tretinoin comprise a core encapsulated by a shell, wherein said core comprises tretinoin in a solid form; wherein the microencapsulation efficiency of the tretinoin is at least 90%.

18. The pharmaceutical composition according to claim 17, wherein said tretinoin is at a concentration of above 14% w/w within the core.

19. The pharmaceutical composition according to claim 16, wherein the tretinoin dissolution rate is between 5% to 35% weight/h as measured in a medium of 30%:70% V/V mixture of water: isopropyl alcohol at 32° C. and wherein the BPO dissolution rate is between 12% to 60% weight/h as measured in a medium of 55%:45% mixture of water: acetonitrile at ambient temperature.

20. The pharmaceutical composition according to claim 17, wherein the tretinoin dissolution rate is between 5% to 35% weight/h as measured in a medium of 30%:70% V/V mixture of water: isopropyl alcohol at 32° C. and wherein the BPO dissolution rate is between 12% to 60% weight/h as measured in a medium of 55%:45% mixture of water: acetonitrile at ambient temperature.

21. The pharmaceutical composition according to claim 16, wherein the microcapsules of the benzoyl peroxide have microencapsulation efficiency of at least 75% and the microcapsules of the tretinoin have microencapsulation efficiency of at least 90%.

22. The pharmaceutical composition according to claim 17, wherein after two weeks storage at 40° C. and 75% relative humidity a concentration of all-trans 5,6-epoxy retinoic acid is less than 1% by weight of the initial tretinoin amount prior to storage.

23. The pharmaceutical composition according to claim 17, wherein the microcapsules of the benzoyl peroxide have microencapsulation efficiency of at least 75%, and the microcapsules of the tretinoin have microencapsulation efficiency of at least 90%.

24. The pharmaceutical composition according to claim 16, wherein after two weeks storage at 40° C. and 75% relative humidity a concentration of all-trans 5,6-epoxy retinoic acid is less than 1% by weight of the initial tretinoin amount prior to storage.

25. A method for treating a skin disease, disorder or condition in a subject in need thereof, said method comprising topically administering to said subject a pharmaceutical composition according to claim 10, wherein said skin disease, disorder or condition is selected from the group consisting of: acne, psoriasis, seborrhea, contact dermatitis, rosacea, and any combination thereof.

26. A method for treating a skin disease, disorder or condition in a subject in need thereof, said method comprising topically administering to said subject a pharmaceutical composition according to claim 11, wherein said skin disease, disorder or condition is selected from the group consisting of: acne, psoriasis, seborrhea, contact dermatitis, rosacea, and any combination thereof.

27. A method for treating a skin disease, disorder or condition in a subject in need thereof, said method comprising topically administering to said subject a composition according to claim 16, wherein said skin disease, disorder or condition is selected from the group consisting of: acne, psoriasis, seborrhea, contact dermatitis, rosacea, and any combination thereof.

28. The method according to claim 27, wherein the microcapsules of the benzoyl peroxide have microencapsulation efficiency of at least 75%; and the microcapsules of the tretinoin have microencapsulation efficiency of at least 90%.

29. A method for treating a skin disease, disorder or condition in a subject in need thereof, said method comprising topically administering to said subject a composition according to claim 17, wherein said skin disease, disorder or condition is selected from the group consisting of: acne, psoriasis, seborrhea, contact dermatitis, rosacea, and any combination thereof.

30. The method according to claim 29, wherein the microcapsules of the benzoyl peroxide have microencapsulation efficiency of at least 75%, and the microcapsules of the tretinoin have microencapsulation efficiency of at least 90%.

31. A method for treating rosacea in a subject in need thereof, said method comprising topically administering to said subject a pharmaceutical composition according to claim 10, wherein the microcapsules have microencapsulation efficiency of at least 75%.

32. A method for treating rosacea in a subject in need thereof, said method comprising topically administering to said subject a pharmaceutical composition according to claim 11, wherein the microcapsules have microencapsulation efficiency of at least 75%.

\* \* \* \* \*